(12) United States Patent
Hanson et al.

(10) Patent No.: US 8,153,619 B2
(45) Date of Patent: Apr. 10, 2012

(54) DIAZONAMIDE ANALOGS

(75) Inventors: Gunnar James Hanson, Chapel Hill, NC (US); Ming Zhou, Coppell, TX (US); Qi Wei, Dallas, TX (US); Charles Caldwell, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 354 days.

(21) Appl. No.: 12/471,246

(22) Filed: May 22, 2009

(65) Prior Publication Data

US 2010/0022607 A1 Jan. 28, 2010

Related U.S. Application Data

(60) Provisional application No. 61/055,400, filed on May 22, 2008, provisional application No. 61/084,152, filed on Jul. 28, 2008, provisional application No. 61/112,069, filed on Nov. 6, 2008, provisional application No. 61/114,376, filed on Nov. 13, 2008.

(51) Int. Cl.
*A61K 31/33* (2006.01)
*C07D 513/00* (2006.01)

(52) U.S. Cl. ........................................ 514/183; 540/455
(58) Field of Classification Search .................. None
See application file for complete search history.

(56) References Cited

U.S. PATENT DOCUMENTS

| | | | |
|---|---|---|---|
| 4,261,989 A | 4/1981 | Sasaki et al. | |
| 5,387,584 A | 2/1995 | Schnur | |
| 5,624,677 A | 4/1997 | El-Rashidy et al. | |
| 5,932,566 A | 8/1999 | Schnur et al. | |
| 6,872,721 B2 | 3/2005 | Orme et al. | |
| 7,022,720 B2 | 4/2006 | Harran et al. | |
| 7,538,129 B2 * | 5/2009 | Harran et al. | 514/366 |
| 7,581,620 B2 * | 9/2009 | Woods et al. | 181/264 |
| 7,960,420 B2 * | 6/2011 | Hanson et al. | 514/375 |
| 2006/0089397 A1 | 4/2006 | Harran et al. | |
| 2007/0149583 A1 | 6/2007 | Harran et al. | |
| 2009/0005572 A1 | 1/2009 | Hanson et al. | |
| 2009/0163446 A1 * | 6/2009 | Hanson et al. | 514/92 |
| 2011/0021784 A1 * | 1/2011 | Hanson et al. | 548/218 |

FOREIGN PATENT DOCUMENTS

| WO | WO-02/36075 | 5/2002 |
|---|---|---|
| WO | WO-2005/028434 | 3/2005 |

OTHER PUBLICATIONS

Fernandez. Tetrahedron Letters, 2008, 49, available online Feb. 8, 2008.*
Nicolaou. Journal of the American Chemical Society, 2004, 126, 12888-12896.*
Burgitt. Angewandte Chemie International Edition, 2003, 47, 4961-4966.*
Cheung et al., Bioorg. Med. Chem. Lett. (2005) 15:3338-3343.
Chiosis et al., ACS Chem. Biol. (2006) 1(5):279-284.
Hendrickson et al., J. Org. Chem. (1987) 52:4137-4139.
International Search Report for PCT/US09/45074, mailed on Jul. 9, 2009, 2 pages.
Konda-Yamada et al., Tetrahedron (2002) 58:7851.
Liang and Feng, Tetrahedron Letters (1996) 37:6627-6630.
Moulin et al., J. Amer. Chem. Soc. (2005) 127:6999-7004.
Schollkopf et al., Liebigs Ann. Chem. (1983) 1133-1151.
Soga et al., Curr. Cancer Drug Targets (2003) 3:359-369.
Written Opinion of the International Searching Authority for PCT/US09/45074, mailed on Jul. 9, 2009, 5 pages.
Yamamoto et al., Angew. Chem. (2003) 42:1280-1284.
Yokoyama et al., Eur. J. Org. Chem. (2004) 1244.
Yokoyama et al., Tetrahedron Letters (1999) 40:7803.

* cited by examiner

*Primary Examiner* — Noble Jarrell
(74) *Attorney, Agent, or Firm* — Richard Aron Osman

(57) ABSTRACT

Novel diazonamide analogs having anti-mitotic activity, useful for the treatment of cancer and other proliferative disorders are provided.

24 Claims, 10 Drawing Sheets

Figure 10. *In Vivo* Single Agent Activity Summary for Example 24
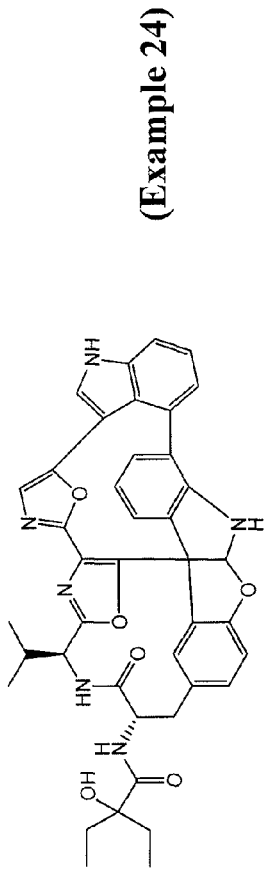
(Example 24)
| Tumor Models | | Ex. 24 vs. Control |
|---|---|---|
| MDA-MB231N1 | Breast | √ |
| MDA-MB435 | Breast | √ |
| Colo205 | Colon | √ |
| HT-29 | Colon | √ |
| A2058 | Melanoma | √ |
| Miapaca | Pancreas | √ |
| HPAC | Pancreas | √ |
√ : $p < 0.05$, p values are calculated based on the days tumors needed to reach the size of 500 mg.
x : no statistic significance

DIAZONAMIDE ANALOGS

RELATED APPLICATIONS

This application claims benefit of priority to U.S. Provisional Application Ser. No. 61/055,400, filed 22 May 2008; and U.S. Provisional Application Ser. No. 61/084,152, filed 28 Jul. 2008; U.S. Provisional Application Ser. No. 61/112,069, filed 6 Nov. 2008; and U.S. Provisional Application Ser. No. 61/114,376, filed 13 Nov. 2008. The contents of these documents are incorporated herein by reference in their entirety.

TECHNICAL FIELD

The invention relates to diazonamide analogs having antimitotic activity, and to salts, pharmaceutical compositions, and conjugates thereof, which are useful as anti-proliferative agents.

BACKGROUND ART

Diazonamide A is a mitotic spindle-disrupting agent first isolated from the marine organism *Diazona angulata*, having the structure:

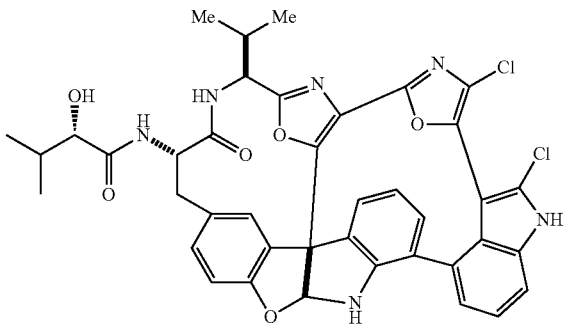

The preparation of diazonamide analogs via macrocyclic indoline intermediates bearing a carbobenzyloxy (Cbz) or o-nitrophenylsulfonyl protected amino group has been previously described. U.S. Pat. No. 7,022,720 correctly discloses the structure of diazonamide A and describes the synthesis of some of its analogs. U.S. application Ser. No. 11/264,502, a continuation-in-part of U.S. application Ser. No. 10/227,509 (now U.S. Pat. No. 7,022,720) was filed 31 Oct. 2005, and is published as US 2006/0089397. U.S. Ser. No. 11/591,016, a continuation-in-part of U.S. application Ser. No. 11/264,502, was filed 31 Oct. 2006, and is published as US 2007/0149583. U.S. application Ser. No. 12/134,984, filed 6 Jun. 2008, and published as US 2009/0005572, describes synthetic methods for the preparation of diazonamide analogs via indoline intermediates.

DISCLOSURE OF THE INVENTION

The present invention is directed towards compounds of formula (I)

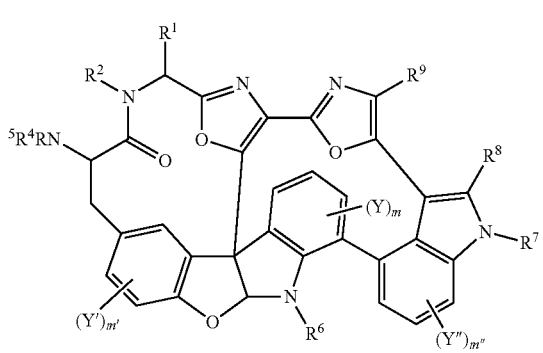

and the pharmaceutically acceptable salts and conjugates thereof. The invention is also directed towards pharmaceutical compositions comprising a compound of formula (I) and/or a salt thereof, to modified forms of such compounds conjugated to stabilizing or targeting agents, and to methods of treating proliferative diseases, in particular cancers, using these compounds and formulations.

In one aspect, the invention provides a compound of formula (I):

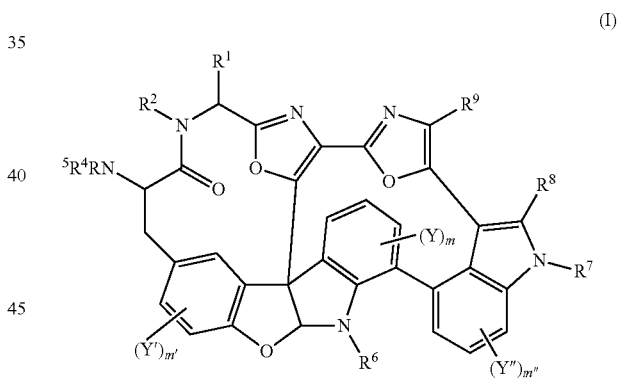

or a pharmaceutically acceptable salt or conjugate thereof;
wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, each of which may be optionally substituted; or $R^1$ and $R^2$ may be taken together with the atoms to which they are attached to form an optionally substituted 5- to 7-membered azacyclic ring, optionally containing an additional heteroatom selected from N, O, and S as a ring member;

$R^4$ is H, or C1-C4 alkyl;

$R^5$ is H, or C1-C8 alkyl, C2-C12 alkenyl, C3-C8 cycloalkyl, C4-C12 cycloalkylalkyl, C2-C12 alkynyl, C6-C12 aryl, C6-C14 arylalkyl, alkylsulfonyl, or arylsulfonyl, or a heteroform of one of these, each of which may be optionally substituted; or is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted; or is —C(=O)OR$^{12}$ or —C(=S)OR$^{12}$, where R$^{12}$ is C1-C8 alkyl, C2-C8 alkenyl, or C2-C8 alkynyl; or R$^4$ and R$^5$ may be taken together with nitrogen to form an optionally substituted 3- to 8-membered azacyclic ring, optionally containing an additional heteroatom selected from N, O, and S as a ring member;

R$^6$ and R$^7$ are independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, or arylsulfonyl, each of which may be optionally substituted;

R$^8$ and R$^9$ are independently H, halo, or C1-C6 alkyl, C2-C6 alkenyl, C2-C6 alkynyl, C6-C12 aryl, C5-C12 heteroaryl, each of which may be optionally substituted, or COOR$^{11}$ or CONR$^{11}_2$, where each R$^{11}$ is independently H or C1-C4 alkyl;

m, m' and m" are independently 0-3; and each Y, Y' and Y" is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted.

In another aspect, the invention provides a compound of formula (I-A):

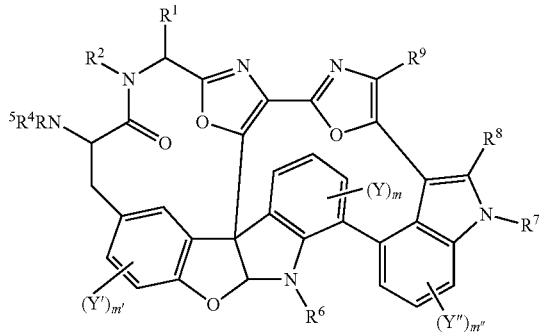

(I-A)

or a pharmaceutically acceptable salt or conjugate thereof;

wherein R$^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

R$^2$ is H, or C1-C8 alkyl, C1-C8 heteroalkyl, C6-C14 arylalkyl, C6-C14 heteroarylalkyl, each of which may be optionally substituted; or R$^1$ and R$^2$ may be taken together with the atoms to which they are attached to form an optionally substituted 5- to 7-membered azacyclic ring, optionally containing an additional heteroatom selected from N, O, and S as a ring member;

R$^4$ is H, or C1-C4 alkyl;

R$^5$ is H, or C1-C8 alkyl, C2-C12 alkenyl, C3-C8 cycloalkyl, C4-C12 cycloalkylalkyl, C2-C12 alkynyl, C6-C12 aryl, C6-C14 arylalkyl, alkylsulfonyl, or arylsulfonyl, or a heteroform of one of these, each of which may be optionally substituted; or is —C(=O)R$^3$ where R$^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted; or R$^4$ and R$^5$ may be taken together with nitrogen to form an optionally substituted 3- to 8-membered azacyclic ring, optionally containing an additional heteroatom selected from N, O, and S as a ring member;

R$^6$ and R$^7$ are independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, or arylsulfonyl, each of which may be optionally substituted;

R$^8$ and R$^9$ are independently H, halo, or C1-C6 alkyl, C2-C6 alkenyl, C2-C6 alkynyl, C6-C12 aryl, or C5-C12 heteroaryl, each of which may be optionally substituted;

m, m' and m" are independently 0-3; and each Y, Y' and Y" is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted.

In another aspect, the invention provides a compound of formula (II):

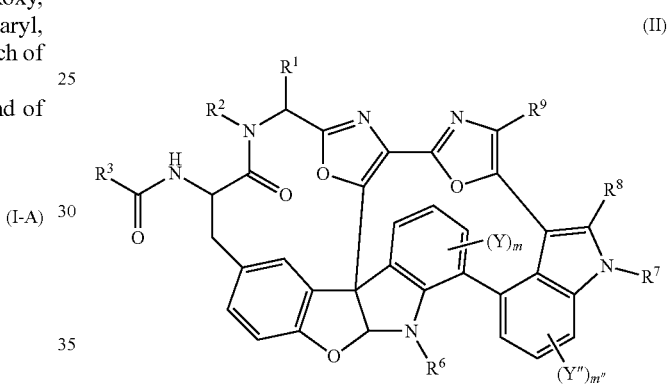

(II)

or a pharmaceutically acceptable salt or conjugate thereof, wherein R$^1$, R$^2$, R$^3$, R$^6$, R$^7$, R$^8$, R$^9$, Y, Y", m and m" are defined as for formula (I).

In further aspect, the invention provides a compound of formula (III):

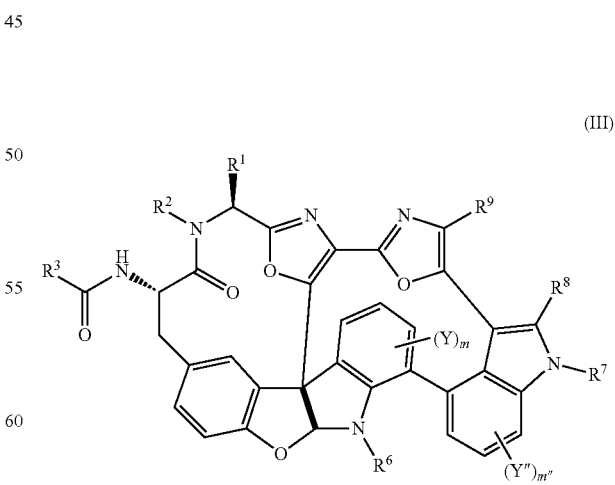

(III)

or a pharmaceutically acceptable salt or conjugate thereof, wherein R$^1$, R$^2$, R$^3$, R$^6$, R$^7$, R$^8$, R$^9$, Y, Y", m and m" are defined as for formula (I).

In another aspect, the invention provides a compound of formula (IV):

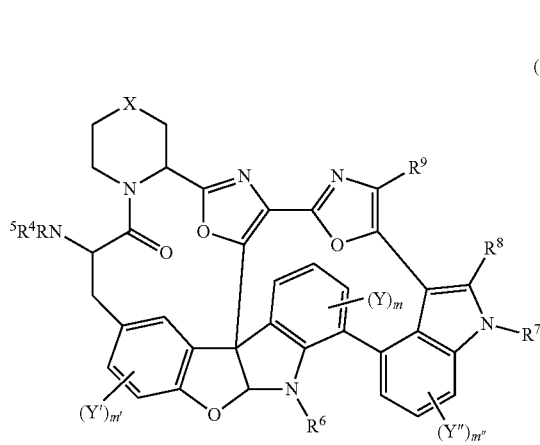

(IV)

or a pharmaceutically acceptable salt or conjugate thereof;

wherein X is O, S, NR" or $(CH_2)_n$, where n is 0-2, and R" is H, C1-C8 alkyl, C5-C8 aryl, C6-C12 arylalkyl, C1-C6 acyl, C6-C12 aroyl, alkylsulfonyl, or arylsulfonyl; and $R^4$, $R^5$, $R^6$, $R^7$, $R^8$, $R^9$, Y, Y', Y", m, m' and m" are defined as for formula (I).

In another aspect, the invention provides a compound of formula (V):

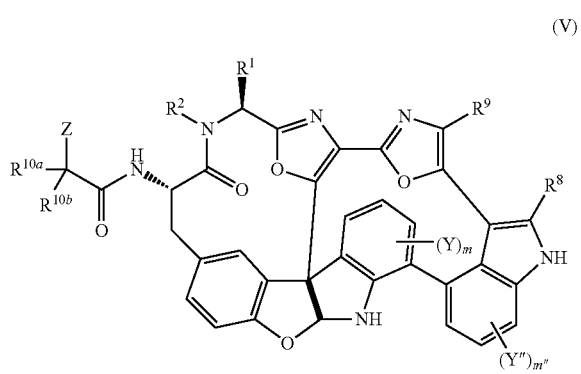

(V)

or a pharmaceutically acceptable salt or conjugate thereof;

wherein $R^1$, $R^2$, $R^8$, $R^9$, Y, Y", m and m" are defined as for formula (I);

Z is OH, OR, $CH_2OR$, SR, or $NR_2$, where each R is independently H, optionally fluorinated C1-C4 alkyl, or optionally fluorinated C1-C4 acyl; and each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted.

In a further aspect, In another aspect, the invention provides a compound of formula (VI):

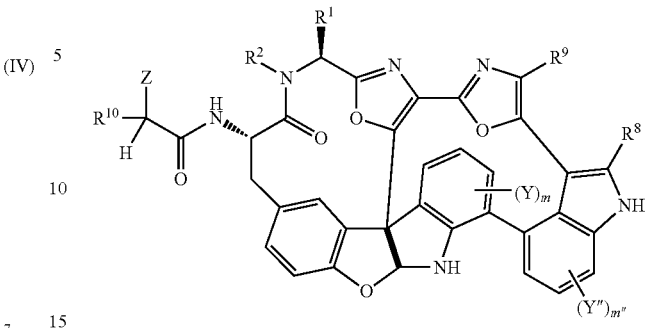

(VI)

or a pharmaceutically acceptable salt or conjugate thereof;
wherein $R^1$, $R^2$, $R^8$, $R^9$, Y, Y", m and m" are defined as for formula (I);

Z is OH, OR, $CH_2OR$, SR, or $NR_2$, where each R is independently H, optionally fluorinated C1-C4 alkyl, or optionally fluorinated C1-C4 acyl; and $R^{10}$ is C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted.

The invention also provides a pharmaceutical composition comprising at least one compound of any of the formulae or any of the embodiments shown herein, and a pharmaceutically acceptable excipient. Pharmaceutical compositions may also comprise pharmaceutically acceptable salts or conjugated forms of the compounds of the invention described herein.

In another aspect, the invention provides a method for treating or ameliorating a cell proliferative disorder, comprising administering to a subject in need thereof a therapeutically effective amount of at least one compound of formulae (I), (II), (III), (IV), (V) or (VI) or a salt, conjugate, or pharmaceutical composition thereof. In some embodiments, the amount administered is sufficient to inhibit cell proliferation. In other embodiments, the amount is sufficient to slow tumor growth or reduce tumor size. In some embodiments, the compound of formulae (I)-(VI) is used in combination with another chemotherapeutic agent or approach.

Provided also are methods for inhibiting cell proliferation, comprising contacting cells with a compound as described herein, or a salt, or conjugate thereof, in an amount effective to inhibit cell proliferation. In some embodiments, the cells are in a cell line, such as a cancer cell line (e.g., a cell line derived from breast, prostate, colon, rectal, melanoma, pancreatic, lung, or hematopoietic cancers, etc.). The cells sometimes are in a tissue, and sometimes are in a tumor in a subject. In other embodiments, the cells are in a tumor, and sometimes are in a tumor in a subject. In certain embodiments, the method further comprises inducing cell apoptosis.

Provided also are methods for treating cancer in a subject in need of such treatment, comprising: administering to the subject a therapeutically effective amount of a compound of any one of formulae (I)-(VI) or a salt or conjugate thereof, as further described herein, in an amount that is effective to treat or ameliorate said cancer.

In some embodiments, the compound of formula (I)-(VI) is a compound in one of the Tables provided herein, or a pharmaceutically acceptable salt or conjugate of one of these compounds.

The invention further provides methods for treating or ameliorating a condition related to aberrant cell proliferation.

For example, provided are methods of treating or ameliorating a cell proliferative disorder in a subject, comprising administering a compound of any one of formulae (I)-(VI) or a salt or conjugate thereof, as described herein, to a subject in need thereof in an amount effective to treat or ameliorate the condition.

In the methods described herein, the subject may be a research animal (e.g., rodent, dog, cat, monkey), optionally containing a tumor such as a xenograft tumor (e.g., human tumor), for example, or may be a human.

These and other embodiments of the invention are described in the description that follows.

BRIEF DESCRIPTION OF THE DRAWINGS

FIG. 10 summarizes the in vivo data for the compound of Example 24.

MODES OF CARRYING OUT THE INVENTION

Figure 1:
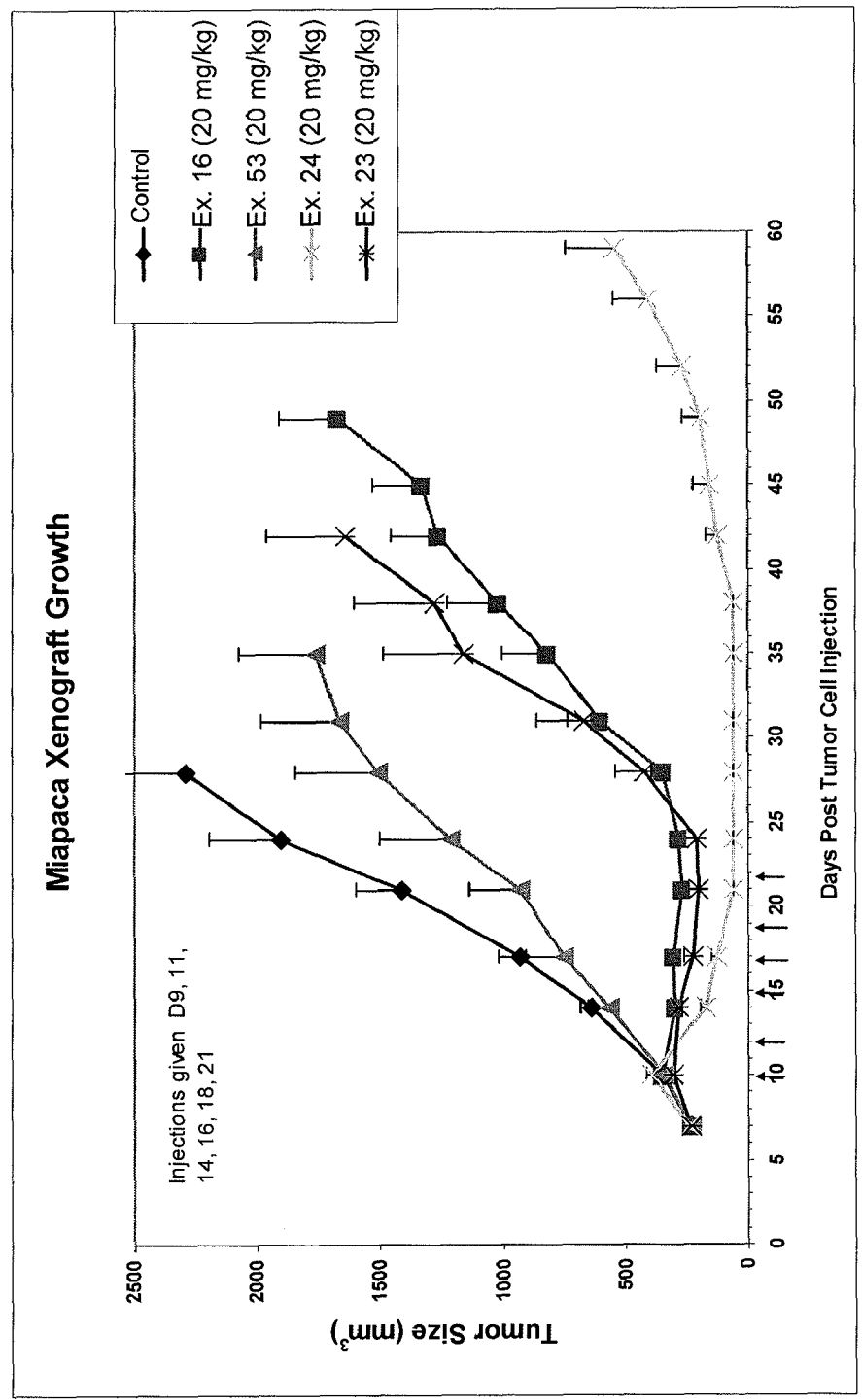
FIG. 1 shows the inhibition of tumor growth in a mouse MiaPaca (pancreatic cancer) xenograft model for animals treated with Compound J (Ex. 16), and the compounds of Example 24, Example 23 and Example 53 at 20 mg/kg.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular forms "a", "an", and "the" include plural references unless indicated otherwise.

As used herein, the term "subject" refers to a human or animal subject. In preferred embodiments, the subject is human.

The terms "treat", "treating" or "treatment" in reference to a particular disease or disorder include prevention of the disease or disorder, and/or lessening, improving, ameliorating, alleviating or removing the symptoms and/or pathology of the disease or disorder.

The term "therapeutically effective amount" or "effective amount" is intended to mean that amount of a drug or pharmaceutical agent that will elicit a biological or medical response of a cell, tissue, system, animal or human that is being sought by a researcher, veterinarian, medical doctor or other clinician. The terms also can refer to reducing or stopping a cell proliferation rate (e.g., slowing or halting tumor growth) or reducing the number of proliferating cancer cells (e.g., removing part or all of a tumor). Sometimes, the rate or cell proliferation is reduced by 10%, 20%, 30%, 40%, 50%, 60%, or 70% or more. Sometimes, the number of proliferating cells is reduced by 10%, 20%, 30%, 40%, 50%, 60%, or 70% or more.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isopropyl, isobutyl, tert-butyl, cyclohexyl, cyclopentylethyl, 2-propenyl, 3-butynyl, and the like. The total number of carbon atoms in each such group is sometimes described herein, e.g., when the group can contain up to twelve carbon atoms it may be described as 1-12C or as C1-C12 or as C1-12 or as $C_{1-12}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-12C (alkyl) or 2-12C (alkenyl or alkynyl). Preferably they contain 1-8C (alkyl) or 2-10C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present. Exemplary heteroalkyls include alkoxyls such as O-alkyl, alkyl ethers, secondary and tertiary alkyl amines, alkyl sulfides, and the like.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than three contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a saturated or partially saturated, monocyclic or fused or spiro polycyclic, carbocycle that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or cycloalkylalkyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl. Also included within the definition of heteroacyl groups are thioacyl substituents, e.g., —C(=S)R, and imine groups, e.g., —C(=NH)R.

Acyl and heteroacyl groups are bonded to any group or molecule to which they are attached through the open valence of the carbonyl carbon atom. Typically, they are C1-C8 acyl groups, which include formyl, acetyl, trifluoroacetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. Preferably the monocyclic aryl and heteroaryl groups contain 5-6 ring members, and the bicyclic aryl and heteroaryl groups contain 8-10 ring members. Aryl groups sometimes contain 6-12 ring members and may be referred to as C6-C12 aryl; heteroaryl groups sometimes contain 5-12 ring members and may be referred to as C5-C12 heteroaryl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof, preferably a C1-C4 alkyl. These linkers may also include a carbonyl group, thus making them able to provide substituents as an acyl or heteroacyl moieties. Sometimes, arylalkyl groups contain 7-20 carbon atoms, preferably 7-14 carbon atoms, including the aryl and alkyl portions; sometimes heteroarylalkyl groups contain 6-20 atoms, preferably 6-14 atoms, including carbon atoms and heteroatoms in the alkyl and heteroaryl portions.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. Preferably, an arylalkyl group includes one or two optionally substituted phenyl rings and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated. Examples of arylalkyl groups include optionally substituted benzyl, phenylethyl, diphenylmethyl, and triphenylmethyl groups. Optional substituents when present on the aryl ring of an arylalkyl group are the same as those described herein for an aryl ring.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, cycloalkyl, alkynyl, acyl, aryl, and arylalkyl are heteroalkyl, heteroalkenyl, heterocyclyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

Unless otherwise indicated, the term "oxo" refers to =O.

"Halo", as used herein, includes fluoro, chloro, bromo and iodo. Fluoro, chloro, and bromo are often preferred.

"Amino" as used herein refers to NH$_2$, but where an amino is described as "substituted" or "optionally substituted", the term includes NR$_2$ wherein each R is independently H, or is an alkyl, alkenyl, alkynyl, acyl, aryl, or arylalkyl group or a heteroform of one of these groups, each of which may be optionally substituted with the substituents described herein as suitable for the corresponding type of group. The term also includes forms wherein the two R groups on one nitrogen atom are linked together to form a 3-8 membered monocyclic azacyclic ring or an 8-12 membered bicyclic fused azacyclic ring system, each of which may be saturated, unsaturated or aromatic and which may contain 1-3 heteroatoms independently selected from N, O and S as ring members, and which may be optionally substituted with the substituents described as suitable for alkyl groups or, if NR$_2$ comprises an aromatic group, it may be optionally substituted with the substituents described as typical for heteroaryl groups.

Amino groups may optionally be in a protected or unprotected form. One of skill in the art would appreciate that appropriate amine protecting groups may vary depending on the functionality present in the particular molecule and the nature of the amino group. Suitably protected amines may include, for example, amines protected as carbamates (e.g., tert-butoxycarbonyl (Boc), benzyloxycarbonyl (Cbz), fluorenylmethyloxy-carbonyl (Fmoc), allyloxycarbonyl (Alloc) or (trialkylsilyl)ethoxycarbonyl), carboxamides (e.g., formyl, acyl or trifluoroacetyl, benzoyl), sulfonamides, phthalimides, succinimides, Schiff's base derivatives, and the like. Also included are alkyl or allyl amines, as well as trialkylsilyl protected amines.

Where an amine is present in protected form, it is sometimes desirable to remove the protecting group. Thus, the methods of the present invention also optionally include a step of removing any protecting groups on an amine or aminoalkyl group.

The terms "alkylsulfonyl" and "arylsulfonyl" as used herein refer to moieties of the form —SO$_2$alkyl or —SO$_2$aryl, where alkyl and aryl are defined as above. Optionally fluorinated C$_{1-4}$alkyl, and optionally substituted phenyl groups are preferred for sulfonyl moieties. The phenyl groups of an arylsulfonyl moiety may be optionally substituted with one or more substituents suitable for an aryl ring; for example, they may be substituted by halo, methyl, nitro, alkoxy, amino, or the like. Such sulfonyl moieties, when present on oxygen form sulfonates. Such sulfonyl moieties form sulfonamides when present on nitrogen, and sulfones when present on carbon. Representative sulfonates include, e.g., —OSO$_2$Me (mesylate), —OSO$_2$CF$_3$ (triflate), —OSO$_2$tolyl (tosylate), and the like.

The term "alkoxycarbonyl" as used herein refers to a moiety of the form —COOR', where R' is C1-C8 alkyl, C2-C8 alkenyl, C5-C6 aryl, or C6-C14 arylalkyl, trialkylsilyl, or the like, each of which may be optionally substituted. When present on nitrogen, such alkoxycarbonyl moieties form carbamates, which are frequently used as nitrogen protecting groups. In some such embodiments, R' may be optionally halogenated C1-C4 alkyl (e.g., tert-butyl, methyl, ethyl, 2,2,2-trichloroethyl, 1,1-dimethyl-2,2,2-trichloroethyl), allyl, optionally substituted benzyl, fluorenylmethyl, or trialkylsilyl (e.g., triisopropylsilyl, triethylsilyl, tert-butyldimethylsilyl). When present on carbon, such moieties may also be referred to as carboxylate esters, carboalkoxy groups, or the like.

The term "substituted" means that the specified group or moiety bears one or more non-hydrogen substituents. The term "unsubstituted" means that the specified group bears no such substituents.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Alkyl, alkenyl and alkynyl groups are often substituted to the extent that such substitution makes sense chemically. Typical substituents include, but are not limited to, halo, OH, =O, =N—CN, =N—OR, =NR, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted with one or more groups selected from halo, OH, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C7-C20 arylalkyl, or C6-C20 heteroarylalkyl. Alkyl, alkenyl and alkynyl groups can also be substituted by C1-C8 acyl, C2-C8 heteroacyl, C6-C12 aryl or C5-C12 heteroaryl, each of which can be substituted by the substituents that are appropriate for the particular group. Preferred substituents when present on an alkyl, alkenyl or alkynyl group, or a heteroform of one of these, include halo, OH, =O, OR, SR, and NR$_2$, where R is defined as above; preferably, each R is independently H, optionally fluorinated C1-C4 alkyl, or optionally fluorinated C1-C4 acyl. Particularly preferred substituents include OH, =O, C1-C4 alkoxy, OAc, NHAc, NH$_2$, and NHMe. Sometimes, optional substituents present on an alkyl, alkenyl or alkynyl group, or a heteroform of one of these, include NRSO$_2$R, NRCONR$_2$, COOR, or CONR$_2$, where R is defined as above; preferably, each R is independently H, optionally fluorinated C1-C4 alkyl, or is C6-C12 aryl, C5-C12 heteroaryl, C6-C20 arylalkyl, or C6-C20 heteroarylalkyl, each of which may be optionally substituted.

Aryl and heteroaryl moieties may be substituted with a variety of substituents including optionally fluorinated C1-C8 alkyl, C2-C8 alkenyl, C2-C8 alkynyl, C6-C12 aryl, C1-C8 acyl, C5-20 arylalkyl, and heteroforms of these, each of which can itself be further substituted; other substituents for aryl and heteroaryl moieties include halo, OH, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C6-C20 arylalkyl, or C6-C20 heteroarylalkyl, and each R is optionally substituted as described above for alkyl groups. The substituent groups on an aryl or heteroaryl group may of course be further substituted with the groups described herein as suitable for each type of group that comprises the substituent. Preferred substituents when present on an aryl or heteroaryl group include halo, OH, OR, SR, NR$_2$, CN, COOR, CONR$_2$, and NO$_2$, where R is defined as above.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

In one aspect, the invention provides a compound of formula (I):

(I)

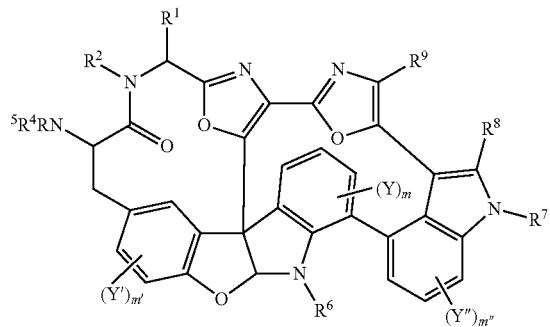

or a pharmaceutically acceptable salt or conjugate thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, each of which may be optionally substituted; or $R^1$ and $R^2$ may be taken together with the atoms to which they are attached to form an optionally substituted 5- to 7-membered azacyclic ring, optionally containing an additional heteroatom selected from N, O, and S as a ring member;

$R^4$ is H, or C1-C4 alkyl;

$R^5$ is H, or C1-C8 alkyl, C2-C12 alkenyl, C3-C8 cycloalkyl, C4-C12 cycloalkylalkyl, C2-C12 alkynyl, C6-C12 aryl, C6-C14 arylalkyl, alkylsulfonyl, or arylsulfonyl, or a heteroform of one of these, each of which may be optionally substituted; or is —C(=O)R$^3$ where R$^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted; or is —C(=O)OR$^{12}$ or —C(=S)OR$^{12}$, where R$^{12}$ is C1-C8 alkyl, C2-C8 alkenyl, or C2-C8 alkynyl; or $R^4$ and $R^5$ may be taken together with nitrogen to form an optionally substituted 3- to 8-membered azacyclic ring, optionally containing an additional heteroatom selected from N, O, and S as a ring member;

$R^6$ and $R^7$ are independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, or arylsulfonyl, each of which may be optionally substituted;

$R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or COOR$^{11}$ or CONR$^{11}$$_2$, where each R$^{11}$ is independently H or C1-C4 alkyl;

m, m' and m" are independently 0-3; and each Y, Y' and Y" is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted.

In another aspect, the invention provides a compound of formula (I-A):

(I-A)

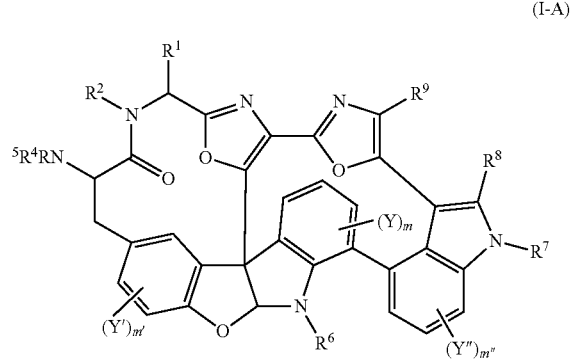

or a pharmaceutically acceptable salt or conjugate thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, each of which may be optionally substituted; or $R^1$ and $R^2$ may be taken together with the atoms to which they are attached to form an optionally substituted 5- to 7-membered azacyclic ring, optionally containing an additional heteroatom selected from N, O, and S as a ring member;

$R^4$ is H, or C1-C4 alkyl;

$R^5$ is H, or C1-C8 alkyl, C2-C12 alkenyl, C3-C8 cycloalkyl, C4-C12 cycloalkylalkyl, C2-C12 alkynyl, C6-C12 aryl, C6-C14 arylalkyl, alkylsulfonyl, or arylsulfonyl, or a heteroform of one of these, each of which may be optionally substituted; or is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted; or $R^4$ and $R^5$ may be taken together with nitrogen to form an optionally substituted 3- to 8-membered azacyclic ring, optionally containing an additional heteroatom selected from N, O, and S as a ring member;

$R^6$ and $R^7$ are independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, or arylsulfonyl, each of which may be optionally substituted;

$R^8$ and $R^9$ are independently H, halo, or C1-C6 alkyl, C2-C6 alkenyl, C2-C6 alkynyl, C6-C12 aryl, or C5-C12 heteroaryl, each of which may be optionally substituted;

m, m' and m" are independently 0-3; and each Y, Y' and Y" is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted.

In compounds of formula (I) and (I-A), $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted. In certain preferred embodiments, $R^1$ is optionally substituted C1-C4 alkyl, C2-C4 alkenyl or C2-C4 alkynyl; in some such embodiments, $R^1$ is isopropyl.

In compounds of formula (I) and (I-A), $R^2$ is H, or C1-C8 alkyl, C1-C8 heteroalkyl, C6-C14 arylalkyl, C6-C14 heteroarylalkyl, each of which may be optionally substituted. In specific embodiments, $R^2$ is H or methyl. In certain preferred embodiments, $R^2$ is H.

In other embodiments, $R^1$ and $R^2$ are taken together with the atoms to which they are attached to form an optionally substituted 5- to 7-membered azacyclic ring, optionally containing an additional heteroatom selected from N, O, and S as a ring member. In specific embodiments, $R^1$ and $R^2$ are taken together to form an optionally substituted 5- to 7-membered azacyclic ring containing no additional heteroatoms, i.e., an optionally substituted pyrrolidine, piperidine or homopiperidine ring. In other embodiments, $R^1$ and $R^2$ are taken together to form an optionally substituted 5- to 7-membered azacyclic ring containing an additional heteroatom selected from N, O and S. In some such embodiments, $R^1$ and $R^2$ are taken together to form an optionally substituted morpholine, thiomorpholine, piperazine, or homopiperazine ring.

In compounds of formula (I) and (I-A), $R^4$ is H, or C1-C4 alkyl. In preferred embodiments, $R^4$ is H.

In certain embodiments of formula (I) and (I-A), $R^5$ is H, or C1-C8 alkyl, C2-C12 alkenyl, C3-C8 cycloalkyl, C4-C12 cycloalkylalkyl, C2-C12 alkynyl, C6-C12 aryl, C6-C14 arylalkyl, alkylsulfonyl, or arylsulfonyl, or a heteroform of one of these, each of which may be optionally substituted.

In other embodiments of formula (I) and (I-A), $R^5$ is —C(=O)O$R^{12}$ or —C(=S)O$R^{12}$, where $R^{12}$ is C1-C8 alkyl, C2-C8 alkenyl, or C2-C8 alkynyl.

In further embodiments of formula (I) and (I-A), $R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted.

In certain embodiments, $R^5$ is C(=O)$R^3$, where $R^3$ is C1-C8 alkyl, C2-C10 alkenyl, C3-C6 cycloalkyl, C4-C8 cycloalkylalkyl, or C6-C8 arylalkyl, each of which may be optionally substituted. In preferred embodiments, the alkyl group comprising part of $R^3$ is substituted with at least one substituent selected from the group consisting of OH, OMe, OAc, $NH_2$, NHMe, $CH_2OH$ and NHAc.

In certain embodiments of formula (I) and (I-A), $R^5$ is C(=O)$R^3$, where $R^3$ is a group of the form —C(Z)$R^{10a}R^{10b}$, where Z is OH, OR, $CH_2OR$, SR, or $NR_2$, where each R is independently H, optionally fluorinated C1-C4 alkyl, or optionally fluorinated C1-C4 acyl, and each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted. In some such embodiments, Z is OH, OMe, OAc, $CH_2OH$, SH, SMe, SAc, $NH_2$, NHMe, $NMe_2$, or NHAc. Sometimes, Z is OH, OMe, OAc, $NH_2$, NHMe, or NHAc. In certain preferred embodiments, Z is OH. In some such embodiments, each of $R^{10a}$ and $R^{10b}$ is independently C1-C4 alkyl, C3-C6 cycloalkyl, or optionally substituted phenyl. In other embodiments, the two $R^{10}$ groups may be taken together with the carbon atom to which they are attached to form a C3-C8 cycloalkyl or a C3-C8 heterocyclyl group, each of which may be optionally substituted.

In other embodiments of formula (I) and (I-A), $R^5$ is C(=O)$R^3$, where $R^3$ is a group of the formula —CH(Z)$R^{10}$, where Z is OH, OR, $CH_2OR$, SR, or $NR_2$, where each R is independently H, optionally fluorinated C1-C4 alkyl, or optionally fluorinated C1-C4 acyl, and $R^{10}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted. In some such embodiments, Z is OH, OMe, OAc, $CH_2OH$, SH, SMe, SAc, $NH_2$, NHMe, $NMe_2$, or NHAc. Sometimes, Z is OH, OMe, OAc, $NH_2$, NHMe, or NHAc. In certain preferred embodiments, Z is OH.

In other embodiments of formula (I) and (I-A), $R^4$ and $R^5$ may be taken together with nitrogen to form an optionally substituted 3- to 8-membered azacyclic ring, optionally containing an additional heteroatom selected from N, O, and S as a ring member.

In compounds of formula (I) and (I-A), $R^6$ and $R^7$ are independently H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, or arylsulfonyl, each of which may be optionally substituted. In some embodiments, each of $R^6$ and $R^7$ is independently H or Me. In preferred embodiments of formula (I) and (I-A), each of $R^6$ and $R^7$ is H. In some embodiments, a substituent at $R^6$ and/or $R^7$ may function as a protecting group. It will be understood that the methods described herein include an optional deprotection step to remove any protecting groups present on the molecule.

In compounds of formula (I), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or $COOR^{11}$ or $CONR^{11}_2$, where each $R^{11}$ is independently H or C1-C4 alkyl. In compounds of formula (I-A), $R^8$ and $R^9$ are independently H, halo, or C1-C6 alkyl, C2-C6 alkenyl, C2-C6 alkynyl, C6-C12 aryl, or C5-C12 heteroaryl, each of which may be optionally substituted. In certain preferred embodiments of formula (I) and (I-A), at least one of $R^8$ and $R^9$ is halo. In other preferred embodiments, $R^8$ and $R^9$ are both chloro. In other preferred embodiments, $R^8$ and $R^9$ are both H. In some embodiments of formula (I), at least one of $R^8$ and $R^9$ is $COOR^{11}$ or $CONR^{11}_2$, where each $R^{11}$ is independently H or C1-C4 alkyl. In some such embodiments, $R^8$ is $COOR^{11}$, and $R^{11}$ is H or methyl.

In compounds of formula (I) and (I-A), each of m, m' and m" is an integer from 0-3. In certain embodiments, m is 0 or 1, and m' and m" are 0. In other embodiments, m is 0 or 1, m' is 0, and m" is 1.

In compounds of formula (I) and (I-A), each Y, Y' and Y" is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain preferred embodiments, m is 1; in some such embodiments, Y is halo. In other preferred embodiments, m" is 1; in some such embodiments, Y" is OH or OMe.

In specific embodiments of formula (I) and (I-A), when $R^5$ is —C(O)$R^3$, $R^3$ is a C1-C8 straight chain, branched, or cycloalkyl group, each of which is substituted on the carbon atom adjacent to the carbonyl group that is part of $R^5$ with OH, OMe, OAc, $NH_2$, NHMe, $CH_2OH$ and NHAc.

The same groups described herein as useful for compounds of certain embodiments formula (I) and (I-A), are also suitable for compounds of certain embodiments of formulae (II), (II-A), (III), (III-A), (IV), (V), (V-A) and (VI).

In another aspect, the invention provides a compound of formula (II):

(II)

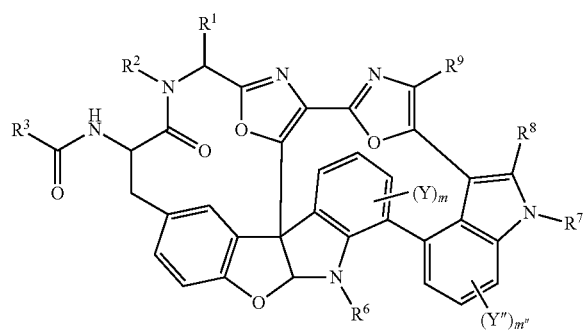

or a pharmaceutically acceptable salt or conjugate thereof, wherein $R^1$, $R^2$, $R^3$, $R^6$, $R^7$, $R^8$, $R^9$, Y, Y", m and m" are defined as for formula (I).

In some embodiments, the compound of formula (II) has the structure of formula (II-A) or (II-B):

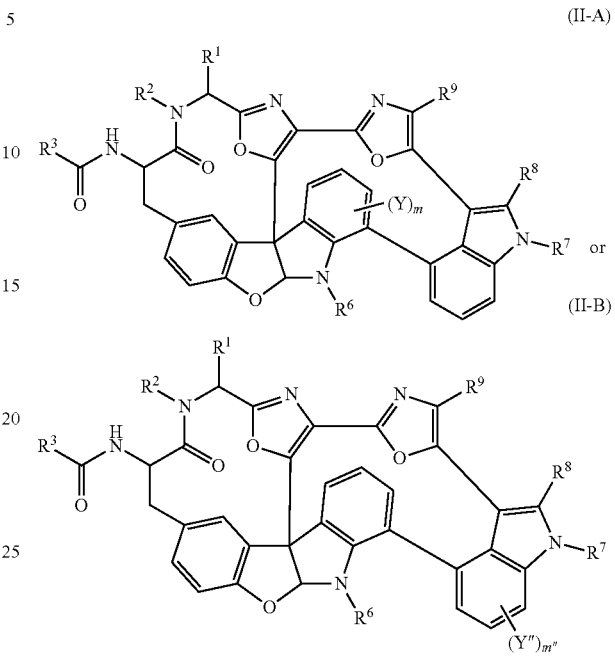

or a pharmaceutically acceptable salt or conjugate thereof, wherein $R^1$, $R^2$, $R^3$, $R^6$, $R^7$, $R^8$, $R^9$, Y, Y", m and m" are defined as for formula (II).

It will be understood that embodiments of formula (II) described herein also apply to compounds of formula (II-A) and (II-B).

In compounds of formula (II), $R^1$, $R^2$, $R^3$, $R^6$, $R^7$, $R^8$, $R^9$, Y, Y", m and m" are defined as for formula (I). In certain preferred embodiments, m is 0 or 1, and Y is halo when m is 1. In other preferred embodiments, m" is 0 or 1, and Y" is OH or OMe when m" is 1.

In compounds of formula (II-A), $R^1$, $R^2$, $R^3$, $R^6$, $R^7$, $R^8$, $R^9$, Y and m are defined as for formula (II). In preferred embodiments, m is 0 or 1, and Y is halo when m is 1.

In compounds of formula (II-B), $R^1$, $R^2$, $R^3$, $R^6$, $R^7$, $R^8$, $R^9$, Y" and m" are defined as for formula (II). In preferred embodiments, m" is 0 or 1, and Y" is OH or OMe when m is 1.

In preferred embodiments of formula (II), $R^3$ is C1-C8 alkyl, C2-C10 alkenyl, C3-C6 cycloalkyl, C4-C8 cycloalkylalkyl, or C6-C8 arylalkyl, each of which may be optionally substituted. In particularly preferred embodiments, the alkyl group comprising part of $R^3$ is substituted with at least one substituent selected from the group consisting of OH, OMe, OAc, $NH_2$, NHMe, $CH_2OH$ and NHAc.

In certain embodiments of formula (II), $R^3$ is a group of the form —C(Z)$R^{10a}R^{10b}$, where Z is OH, OR, $CH_2OR$, SR, or $NR_2$, where each R is independently H, optionally fluorinated C1-C4 alkyl, or optionally fluorinated C1-C4 acyl, and each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted. In some such embodiments, Z is OH, OMe, OAc, $CH_2OH$, SH, SMe, SAc, $NH_2$, NHMe, $NMe_2$, or NHAc. Sometimes, Z is OH, OMe, OAc, NH₂, NHMe, or NHAc. In certain preferred embodiments, Z is OH. In some such embodiments, each of $R^{10a}$ and $R^{10b}$ is independently C1-C4 alkyl, C3-C6 cycloalkyl, or optionally substituted phenyl. In other embodiments, the two $R^{10}$ groups may be taken together with the carbon atom to which they are attached to form a C3-C8 cycloalkyl or a C3-C8 heterocyclyl group, each of which may be optionally substituted.

In other embodiments of formula (II), $R^3$ is a group of the formula —CH(Z)$R^{10}$, where Z is OH, OR, CH₂OR, SR, or NR₂, where each R is independently H, optionally fluorinated C1-C4 alkyl, or optionally fluorinated C1-C4 acyl, and $R^{10}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted. In some such embodiments, Z is OH, OMe, OAc, CH₂OH, SH, SMe, SAc, NH₂, NHMe, NMe₂, or NHAc. Sometimes, Z is OH, OMe, OAc, NH₂, NHMe, or NHAc. In certain preferred embodiments, Z is OH. In some such embodiments, $R^{10}$ is C1-C4 alkyl, C3-C6 cycloalkyl, or optionally substituted phenyl.

In some embodiments of formula (II), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or COO$R^{11}$ or CON$R^{11}$₂, where each $R^{11}$ is independently H or C1-C4 alkyl. In some embodiments of formula (II), $R^8$ and $R^9$ are independently H, halo, or C1-C6 alkyl, C2-C6 alkenyl, C2-C6 alkynyl, C6-C12 aryl, or C5-C12 heteroaryl, each of which may be optionally substituted. In frequent embodiments, each of $R^8$ and $R^9$ is H.

Specific embodiments described for formulae (I) and (II) are also suitable for compounds of formula (III), (IV), (V), and (VI).

In further aspect, the invention provides a compound of formula (III):

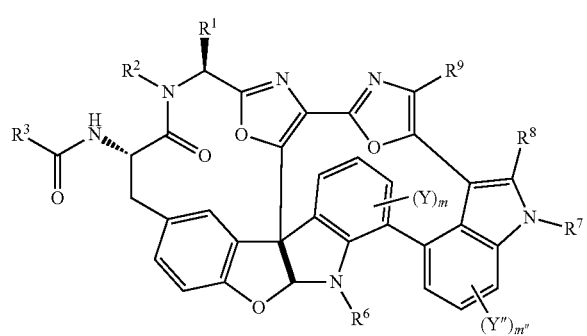

(III)

or a pharmaceutically acceptable salt or conjugate thereof, wherein $R^1$, $R^2$, $R^3$, $R^6$, $R^7$, $R^8$, $R^9$, Y, Y", m and m" are defined as for formula (I).

In some embodiments, the compound of formula (III) has the structure of formula (III-A) or (III-B):

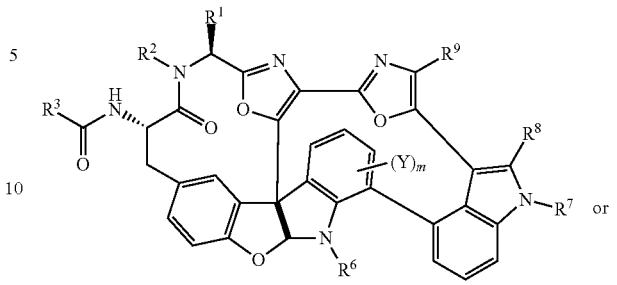

(III-A)

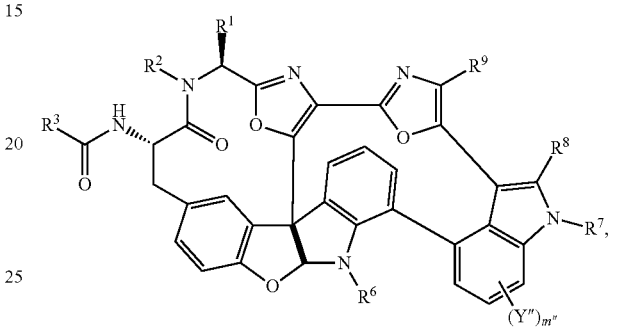

(III-B)

or a pharmaceutically acceptable salt or conjugate thereof, wherein $R^1$, $R^2$, $R^3$, $R^6$, $R^7$, $R^8$, $R^9$, Y and m are defined as for formula (III).

It will be understood that embodiments of formula (III) described herein also apply to compounds of formula (III-A) and (III-B).

In compounds of formula (III), $R^1$, $R^2$, $R^3$, $R^6$, $R^7$, $R^8$, and $R^9$, Y, Y", m and m" are as defined for formula (I). In certain preferred embodiments, m is 0 or 1, and Y is halo when m is 1. In other preferred embodiments, m" is 0 or 1, and Y" is OH or OMe when m" is 1.

In compounds of formula (III-A), $R^1$, $R^2$, $R^3$, $R^6$, $R^7$, $R^8$, and $R^9$, m and Y are defined as for formula (III). In certain preferred embodiments, m is 0 or 1, and Y is halo when m is 1.

In compounds of formula (III-B), $R^1$, $R^2$, $R^3$, $R^6$, $R^7$, $R^8$, and $R^9$, m and Y are defined as for formula (III). In certain preferred embodiments, m" is 0 or 1, and Y" is OH or OMe when m is 1.

In certain embodiments of formula (III), $R^1$ is optionally substituted C1-C4 alkyl, C2-C4 alkenyl or C2-C4 alkynyl; in some such embodiments, $R^1$ is isopropyl. In some embodiments of formula (III), $R^2$ is H or methyl. In certain preferred embodiments, $R^2$ is H. In other embodiments of formula (III), $R^1$ and $R^2$ are taken together with the atoms to which they are attached to form an optionally substituted 5- to 7-membered azacyclic ring, optionally containing an additional heteroatom selected from N, O, and S.

In certain embodiments of formula (III), $R^3$ is a group of the formula —C(Z)$R^{10a}R^{10b}$, where Z is OH, OR, CH₂OR, SR, or NR₂, where each R is independently H, optionally fluorinated C1-C4 alkyl, or optionally fluorinated C1-C4 acyl, and each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted. In some such embodiments, Z is OH, OMe, OAc, CH$_2$OH, SH, SMe, SAc, NH$_2$, NHMe, NMe$_2$, or NHAc. Sometimes, Z is OH, OMe, OAc, NH$_2$, NHMe, or NHAc. In certain preferred embodiments, Z is OH. In some such embodiments, each of R$^{10a}$ and R$^{10b}$ is independently C1-C4 alkyl, C3-C6 cycloalkyl, or optionally substituted phenyl. In other embodiments, the two R$^{10}$ groups may be taken together with the carbon atom to which they are attached to form a C3-C8 cycloalkyl or a C3-C8 heterocyclyl group, each of which may be optionally substituted.

In other embodiments of formula (III), R$^3$ is a group of the formula —CH(Z)R$^{10}$, where Z is OH, OR, CH$_2$OR, SR, or NR$_2$, where each R is independently H, optionally fluorinated C1-C4 alkyl, or optionally fluorinated C1-C4 acyl, and R$^{10}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted. In some such embodiments, Z is OH, OMe, OAc, CH$_2$OH, SH, SMe, SAc, NH$_2$, NHMe, NMe$_2$, or NHAc. Sometimes, Z is OH, OMe, OAc, NH$_2$, NHMe, or NHAc. In certain preferred embodiments, Z is OH.

In some embodiments of formula (III), R$^8$ and R$^9$ are independently H, halo, or C1-C6 alkyl, C2-C6 alkenyl, C2-C6 alkynyl, C6-C12 aryl, C5-C12 heteroaryl, each of which may be optionally substituted, or COOR$^{11}$ or CONR$^{11}$$_2$, where each R$^{11}$ is independently H or C1-C4 alkyl. In some embodiments of formula (II), R$^8$ and R$^9$ are independently H, halo, or C1-C6 alkyl, C2-C6 alkenyl, C2-C6 alkynyl, C6-C12 aryl, or C5-C12 heteroaryl, each of which may be optionally substituted. In frequent embodiments, each of R$^8$ and R$^9$ is H.

In specific embodiments of formula (III), the compound has the formula:

(III-a)

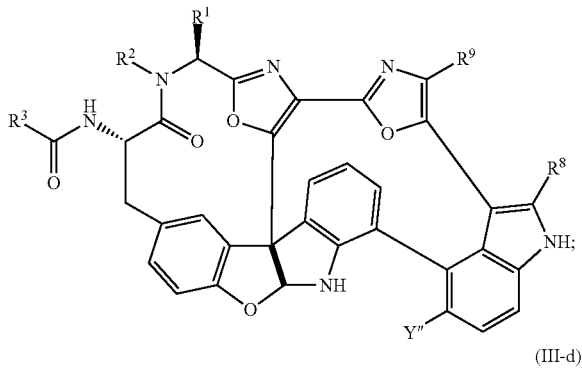

(III-b)

(III-c)

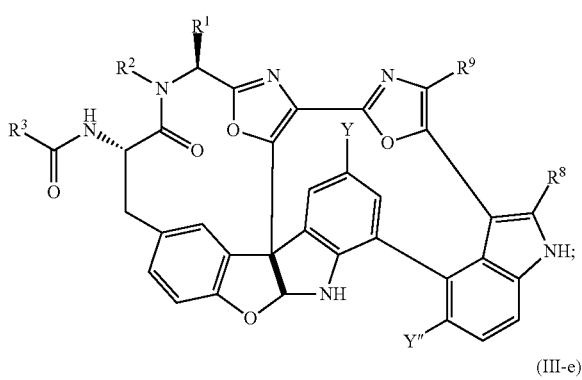

(III-d)

(III-e)

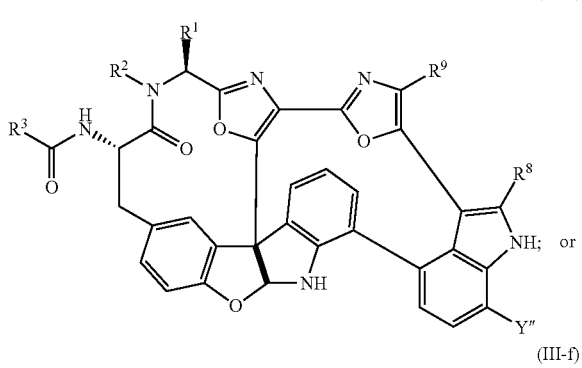

(III-f)

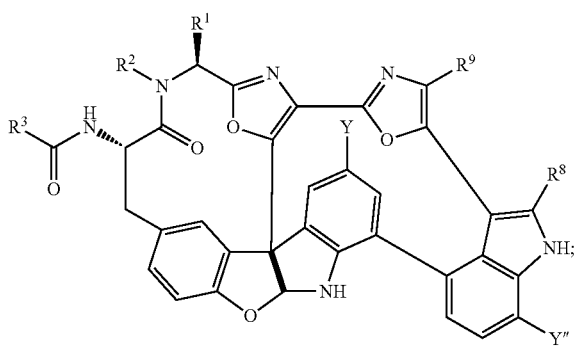

or a pharmaceutically acceptable salt or conjugate thereof, wherein R$^1$, R$^2$, R$^3$, R$^8$, R$^9$, Y and Y" are defined as for formula (III).

In a preferred embodiment of formula (III), the compound has the formula (III-a) or (III-b) and each of R$^8$ and R$^9$ is H. In another embodiment of formula (III), the compound has the formula (III-a) or (III-b) and at least one of R$^8$ and R$^9$ is chloro. In other preferred embodiments, the compound has the formula (III-c), (III-d), (III-e) or (III-f), and Y" is OH or OMe.

Specific embodiments described for formulae (I), (II), and (III) are also suitable for compounds of formula (IV), (V), and (VI).

In another aspect, the invention provides a compound of formula (IV):

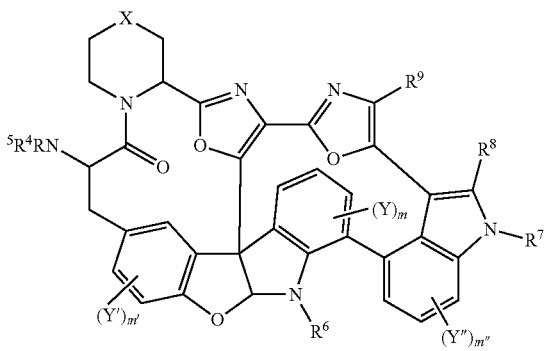

(IV)

or a pharmaceutically acceptable salt or conjugate thereof;
wherein X is O, S, NR" or $(CH_2)_n$, where n is 0-2, and R" is H, C1-C8 alkyl, C5-C8 aryl, C6-C12 arylalkyl, C1-C6 acyl, C6-C12 aroyl, alkylsulfonyl, or arylsulfonyl; and $R^4$, $R^5$, $R^6$, $R^7$, $R^8$, $R^9$, Y, Y', Y", m, m' and m" are defined as for formula (I).

In certain embodiments of formula (IV), the compound has the formula of (IV-A) or (IV-B):

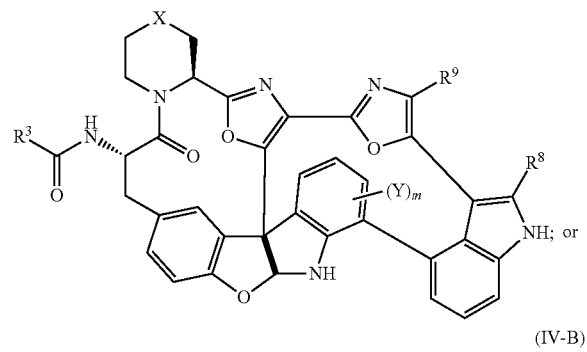

(IV-A)

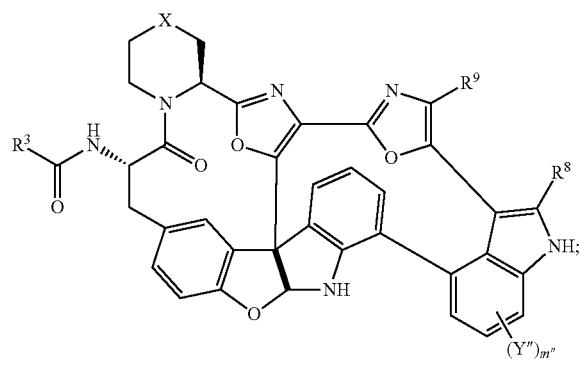

(IV-B)

or a pharmaceutically acceptable salt or conjugate thereof;

wherein $R^3$, $R^8$, $R^9$, Y, Y", m, m" and X are defined as for formula (IV).

It will be understood that embodiments of formula (IV) described herein also apply to compounds of formula (IV-A) and (IV-B).

In compounds of formula (IV), $R^4$, $R^5$, $R^6$, $R^7$, $R^8$, $R^9$, Y, Y', Y", m, m' and m" are defined as for formula (I). In compounds of formula (IV), X is O, S, NR" or $(CH_2)_n$, where n is 0-2, and R" is H, C1-C8 alkyl, C5-C8 aryl, C6-C12 arylalkyl, C1-C6 acyl, C6-C12 aroyl, alkylsulfonyl, or arylsulfonyl. In certain preferred embodiments, X is $(CH_2)_n$, where n is 0-2.

In compounds of formula (IV), $R^4$ is H, or C1-C4 alkyl. In preferred embodiments, $R^4$ is H. In some embodiments of formula (IV), $R^5$ is —C(=O)$R^3$ where $R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C6-C14 arylalkyl, or C6-C14 heteroarylalkyl, each of which may be optionally substituted. In certain embodiments, $R^5$ is C(=O)$R^3$, where $R^3$ is C1-C8 alkyl, C2-C10 alkenyl, C3-C6 cycloalkyl, C4-C8 cycloalkylalkyl, or C6-C8 arylalkyl, each of which may be optionally substituted. In preferred embodiments, the alkyl group comprising part of $R^3$ is substituted with at least one substituent selected from the group consisting of OH, OMe, OAc, $NH_2$, NHMe, $CH_2$OH and NHAc.

In some embodiments of formula (IV) where $R^5$ is C(=O) $R^3$, or in some embodiments of formula (IV-A) or (IV-B), $R^3$ is a group of the form —C(Z)$R^{10a}R^{10b}$, where Z is OH, OR, $CH_2$OR, SR, or $NR_2$, where each R is independently H, optionally fluorinated C1-C4 alkyl, or optionally fluorinated C1-C4 acyl. In such embodiments, each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted; or $R^{10a}$ and $R^{10b}$ may be taken together with the carbon to which they are attached to form a C3-C8 cycloalkyl or a C3-C8 heterocyclyl ring, which may be optionally substituted. In some such embodiments, Z is OH, OMe, OAc, $CH_2$OH, SH, SMe, SAc, $NH_2$, NHMe, $NMe_2$, or NHAc. Sometimes, Z is OH, OMe, OAc, $NH_2$, NHMe, or NHAc. In certain preferred embodiments, Z is OH.

In other embodiments of formula (IV) where $R^5$ is C(=O) $R^3$, or in some embodiments of formula (IV-A) or (IV-B), $R^3$ is a group of the formula —CH(Z)$R^{10}$, where Z is OH, OR, $CH_2$OR, SR, or $NR_2$, where each R is independently H, optionally fluorinated C1-C4 alkyl, or optionally fluorinated C1-C4 acyl, and $R^{10}$ is independently C1-C6 alkyl, C2-C6 alkenyl, C2-C6 alkynyl, C3-C8 cycloalkyl, C3-C8 cycloalkylalkyl, C6-C12 aryl, C7-C20 arylalkyl, or a heteroform of one of these, each of which may be optionally substituted. In some such embodiments, Z is OH, OMe, OAc, $CH_2$OH, SH, SMe, SAc, $NH_2$, NHMe, $NMe_2$, or NHAc. Sometimes, Z is OH, OMe, OAc, $NH_2$, NHMe, or NHAc. In certain preferred embodiments, Z is OH.

In some embodiments of formula (IV), (IV-A) and (IV-B), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or COO$R^{11}$ or CONR$^{11}_2$, where each $R^{11}$ is independently H or C1-C4 alkyl. In other embodiments of formula (IV), (IV-A) and (IV-B), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted. In frequent embodiments, each of $R^8$ and $R^9$ is H.

Specific embodiments described for formulae (I), (II), (III), and (IV) are also suitable for compounds of formula (V) or (VI).

In a preferred aspect, the invention provides a compound of formula (V):

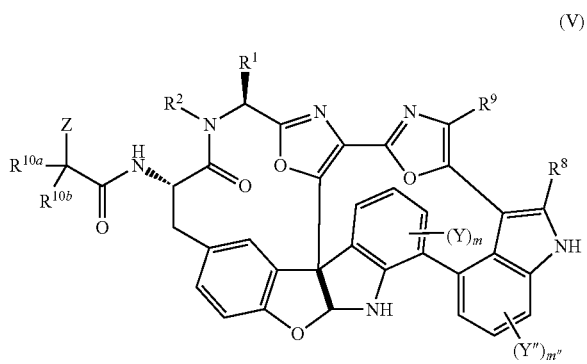

(V)

or a pharmaceutically acceptable salt or conjugate thereof;
wherein $R^1$, $R^2$, $R^8$, $R^9$, Y, Y'', m and m'' are defined as for formula (I);
Z is OH, OR, $CH_2OR$, SR, or $NR_2$, where each R is independently H, optionally fluorinated C1-C4 alkyl, or optionally fluorinated C1-C4 acyl; and
each of $R^{10a}$ and $R^{10b}$ is independently C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted; or
$R^{10a}$ and $R^{10b}$ may be taken together with the carbon to which they are attached to form a C3-C8 cycloalkyl or a C3-C8 heterocyclyl ring, which may be optionally substituted.

In some embodiments, the compound of formula (V) has the structure of formula (V-A) or (V-B):

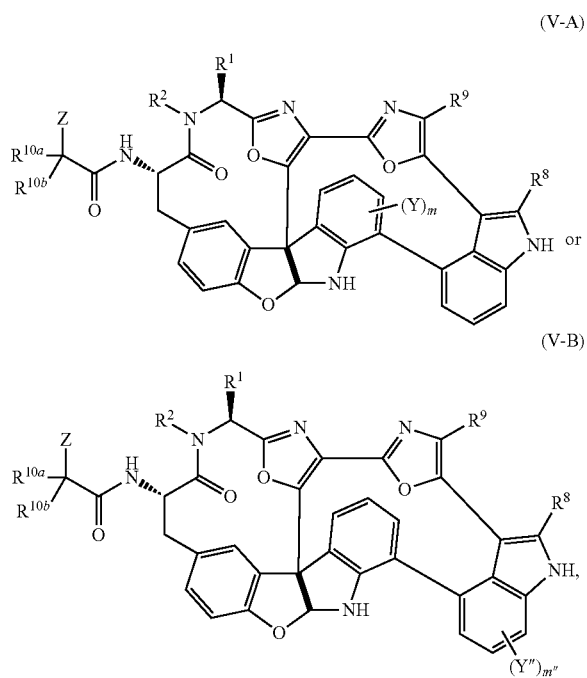

or a pharmaceutically acceptable salt or conjugate thereof;

wherein $R^1$, $R^2$, $R^8$, $R^9$, Y, Y'', m, m'', Z, $R^{10a}$ and $R^{10b}$ are defined as for formula (V).

It will be understood that embodiments of formula (V) described herein also apply to compounds of formula (V-A) and (V-B).

In certain embodiments of Formula (V), $R^1$ is optionally substituted C1-C4 alkyl, C2-C4 alkenyl or C2-C4 alkynyl; in some such embodiments, $R^1$ is isopropyl. In some embodiments of formula (V), $R^1$ is H or C1-C4 alkyl; sometimes, $R^2$ is H or methyl. In certain preferred embodiments, $R^2$ is H. In other embodiments, $R^1$ and $R^2$ are taken together with the atoms to which they are attached to form an optionally substituted 5- to 7-membered azacyclic ring, optionally containing an additional heteroatom selected from N, O, and S as a ring member. In specific embodiments, $R^1$ and $R^2$ are taken together to form an optionally substituted 5- to 7-membered azacyclic ring containing no additional heteroatoms, i.e., an optionally substituted pyrrolidine, piperidine or homopiperidine ring. In other embodiments, $R^1$ and $R^2$ are taken together to form an optionally substituted 5- to 7-membered azacyclic ring containing an additional heteroatom selected from N, O and S. In some such embodiments, $R^1$ and $R^2$ are taken together to form an optionally substituted morpholine, thiomorpholine, piperazine, or homopiperazine ring.

In some embodiments of formula (V), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or $COOR^{11}$ or $CONR^{11}_2$, where each $R^{11}$ is independently H or C1-C4 alkyl. In other embodiments of formula (V), (V-A) and (V-B), $R^8$ and $R^9$ are independently H, halo, or C1-C6 alkyl, C2-C6 alkenyl, C2-C6 alkynyl, C6-C12 aryl, or C5-C12 heteroaryl, each of which may be optionally substituted. In certain embodiments, at least one of $R^8$ and $R^9$ is halo. In other embodiments, $R^8$ and $R^9$ are both chloro. In other preferred embodiments, $R^8$ and $R^9$ are both H. In other preferred embodiments, at least one of $R^8$ and $R^9$ is $COOR^{11}$ or $CONR^{11}_2$.

In compounds of formula (V), each of m and/or m'' is an integer from 0-3. In certain embodiments, each of m and m'' is 0 or 1. In compounds of formula (V) and (V-A), each Y is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m is 1 and Y is halo, preferably chloro. In other embodiments, m is 0. In compounds of formula (V) and (V-B), each Y'' is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m'' is 1 and Y'' is OH or OMe. In other embodiments, m'' is 0.

In compounds of formula (V), m'' is an integer from 0-3. In certain embodiments, m'' is 0 or 1. In compounds of formula (V), each Y'' is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m'' is 1 and Y'' is OH or OMe. In other embodiments, m'' is 0. In frequent embodiments, each of m and m'' is 0.

In compounds of formula (V), Z is OH, OR, $CH_2OR$, SR, or $NR_2$, where each R is independently H, optionally fluorinated C1-C4 alkyl, or optionally fluorinated C1-C4 acyl. In certain embodiments, Z is OH, OMe, OAc, $CH_2OH$, SH, SMe, SAc, $NH_2$, NHMe, $NMe_2$, or NHAc. In preferred embodiments, Z is OH.

In some embodiments of formula (V), $R^{10a}$ and $R^{10b}$ are the same. In other embodiments, $R^{10a}$ and $R^{10b}$ are different. In certain preferred embodiments, each of $R^{10a}$ and $R^{10b}$ comprises at least two carbon atoms. For example, each of $R^{10a}$ and $R^{10b}$ may independently be ethyl, propyl, isopropyl, allyl, propargyl, n-butyl, s-butyl, isobutyl, t-butyl, pentyl, cyclopropyl, and the like; in some such embodiments, $R^{10a}$ and $R^{10b}$ are the same. In a preferred embodiment, each of $R^{10a}$ and $R^{10b}$ is ethyl.

In other embodiments of formula (V), $R^{10a}$ and $R^{10b}$ are taken together with the carbon to which they are attached to form a C3-C8 cycloalkyl or a C3-C8 heterocyclyl ring, which may be optionally substituted. For example, $R^{10a}$ and $R^{10b}$ may be taken together to form an optionally substituted cyclopropyl, cyclobutyl, cyclopentyl, cyclopentenyl, cyclohexyl, cyclohexenyl, tetrahydrofuran, tetrahydropyran, tetrahydrothiofuran, tetrahydrothiopyran, pyrrolidine, or piperidine ring, and the like. In a preferred embodiment, each of $R^{10a}$ and $R^{10b}$ are taken together to form a cyclohexyl or a cyclopentyl ring. In some embodiments, the ring formed by $R^{10a}$ and $R^{10b}$ may be fused to a substituted or unsubstituted phenyl ring to provide, for example, and indenyl or tetrahydronaphthyl ring system.

In specific embodiments of formula (V), the compound has the structure of formula:

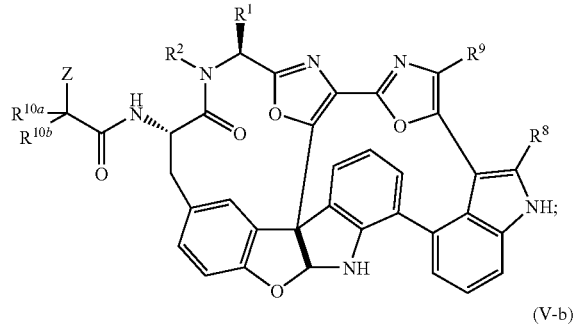

(V-a)

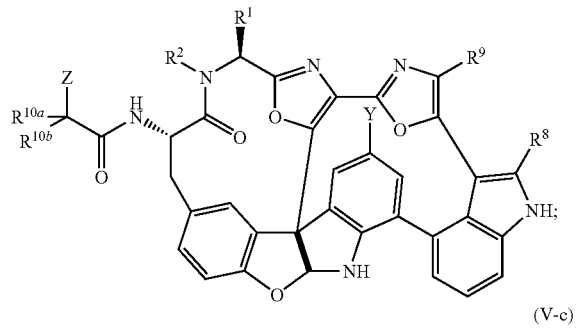

(V-b)

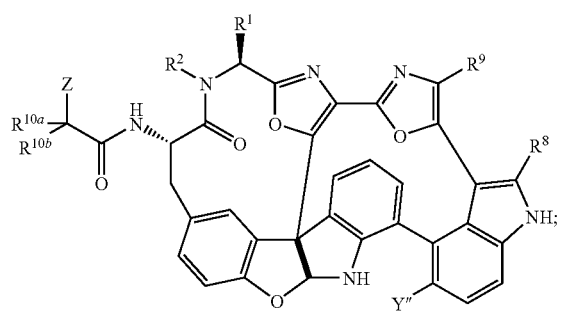

(V-c)

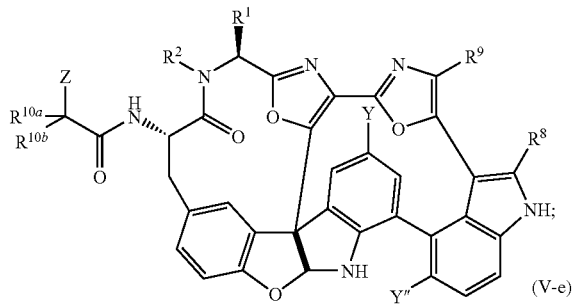

(V-d)

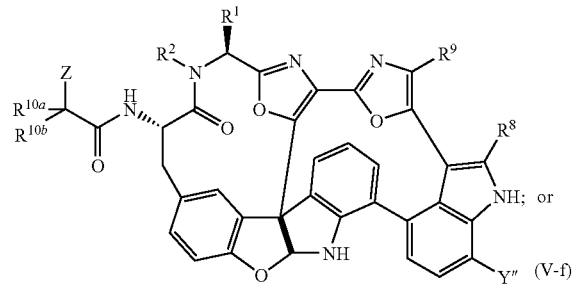

(V-e)

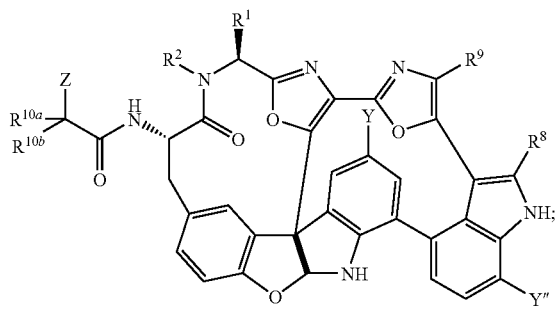

(V-f)

or a pharmaceutically acceptable salt or conjugate thereof; wherein $R^1$, $R^2$, $R^8$, $R^9$, Y, Y", Z, $R^{10a}$ and $R^{10b}$ are defined as for formula (V).

In a preferred embodiment of formula (V), the compound has the formula (V-a) or (V-b) and each of $R^8$ and $R^9$ is H. In other embodiments of formula (V), the compound has the formula (V-a) or (V-b) and at least one of $R^8$ and $R^9$ is chloro. In other preferred embodiments, the compound has the formula (V-c), (V-d), (V-e) or (V-f), and Y" is OH or OMe. In some such embodiments, each of $R^8$ and $R^9$ is H. In other embodiments, at least one of $R^8$ and $R^9$ is $COOR^{11}$ or $CONR^{11}{}_2$.

In another aspect, the invention provides a compound of formula (VI):

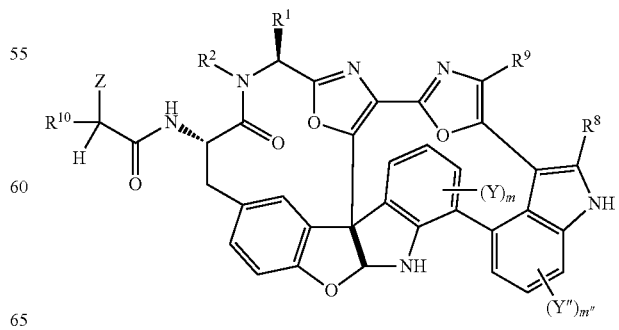

(VI)

or a pharmaceutically acceptable salt or conjugate thereof;

wherein $R^1$, $R^2$, $R^8$, $R^9$, Y, Y", m and m" are defined as for formula (I);

Z is OH, OR, CH$_2$OR, SR, or NR$_2$, where each R is independently H, optionally fluorinated C1-C4 alkyl, or optionally fluorinated C1-C4 acyl; and $R^{10}$ is C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted.

In some embodiments, the compound of formula (VI) has the formula (VI-A) or (VI-B):

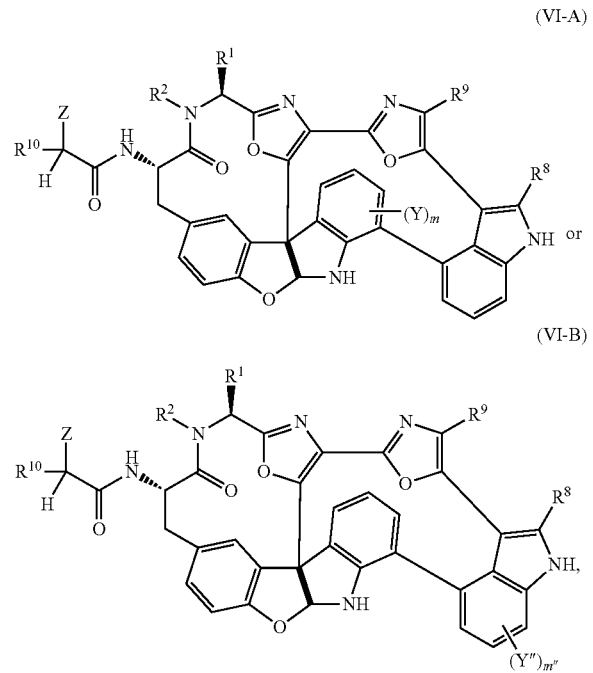

or a pharmaceutically acceptable salt or conjugate thereof;
wherein $R^1$, $R^2$, $R^8$, $R^9$, Y, Y", m and m", Z, and $R^{10}$ are defined as for formula (VI).

It will be understood that embodiments of formula (VI) described herein also apply to compounds of formula (VI-A) and (VI-B).

In certain embodiments of Formula (VI), $R^1$ is optionally substituted C1-C4 alkyl, C2-C4 alkenyl or C2-C4 alkynyl; in some such embodiments, $R^1$ is isopropyl. In some embodiments of formula (VI), $R^2$ is H or C1-C4 alkyl; sometimes, $R^2$ is H or methyl. In certain preferred embodiments, $R^2$ is H. In other embodiments, $R^1$ and $R^2$ are taken together with the atoms to which they are attached to form an optionally substituted 5- to 7-membered azacyclic ring, optionally containing an additional heteroatom selected from N, O, and S as a ring member. In specific embodiments, $R^1$ and $R^2$ are taken together to form an optionally substituted 5- to 7-membered azacyclic ring containing no additional heteroatoms, i.e., an optionally substituted pyrrolidine, piperidine or homopiperidine ring. In other embodiments, $R^1$ and $R^2$ are taken together to form an optionally substituted 5- to 7-membered azacyclic ring containing an additional heteroatom selected from N, O and S. In some such embodiments, $R^1$ and $R^2$ are taken together to form an optionally substituted morpholine, thiomorpholine, piperazine, or homopiperazine ring.

In some embodiments of formula (VI), $R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or COOR$^{11}$ or CONR$^{11}{}_2$, where each $R^{11}$ is independently H or C1-C4 alkyl. In other embodiments of formula (VI), (VI-A) and (VI-B), $R^8$ and $R^9$ are independently H, halo, or C1-C6 alkyl, C2-C6 alkenyl, C2-C6 alkynyl, C6-C12 aryl, or C5-C12 heteroaryl, each of which may be optionally substituted. In certain preferred embodiments, each of $R^8$ and $R^9$ is H. In certain embodiments, at least one of $R^8$ and $R^9$ is halo. In other embodiments, at least one of $R^8$ and $R^9$ is COOR$^{11}$ or CONR$^{11}{}_2$.

In compounds of formula (VI), (VI-A) and (VI-B), each of m and/or m" is an integer from 0-3. In certain embodiments, each of m and m" is 0 or 1. In compounds of formula (VI) and (VI-A), each Y is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m is 1 and Y is halo, preferably chloro. In other embodiments, m is 0. In compounds of formula (VI) and (VI-B), each Y" is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m" is 1 and Y" is OH or OMe. In other embodiments, m" is 0.

In compounds of formula (VI), m" is an integer from 0-3. In certain embodiments, m" is 0 or 1. In compounds of formula (VI), each Y" is independently is halo, OH, or C1-C4 alkoxy, or is C1-C8 alkyl, C2-C8 alkenyl, C2-C8 alkynyl, C6-C12 aryl, or C6-C14 arylalkyl, or a heteroform of one of these, each of which may be optionally substituted. In certain embodiments, m" is 1 and Y" is OH or OMe. In other embodiments, m" is 0. In frequent embodiments, each of m and m" is 0.

In compounds of formula (VI), Z is OH, OR, CH$_2$OR, SR, or NR$_2$, where each R is independently H, optionally fluorinated C1-C4 alkyl, or optionally fluorinated C1-C4 acyl. In certain embodiments, Z is OH, OMe, OAc, CH$_2$OH, SH, SMe, SAc, NH$_2$, NHMe, NMe$_2$, or NHAc. In preferred embodiments, Z is OH.

In some embodiments of formula (VI), $R^{10}$ is C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted. For example, $R^{10}$ may be ethyl, propyl, isopropyl, allyl, propargyl, n-butyl, s-butyl, isobutyl, t-butyl, pentyl, cyclopropyl, and the like.

In specific embodiments of formula (VI), the compound has the formula:

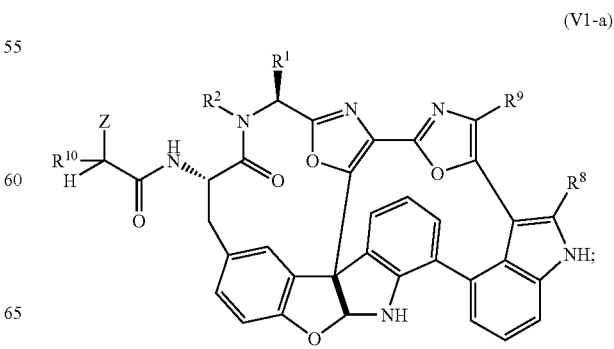

-continued (V1-b)
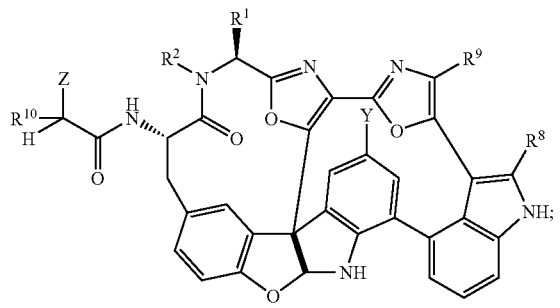

(V1-c)
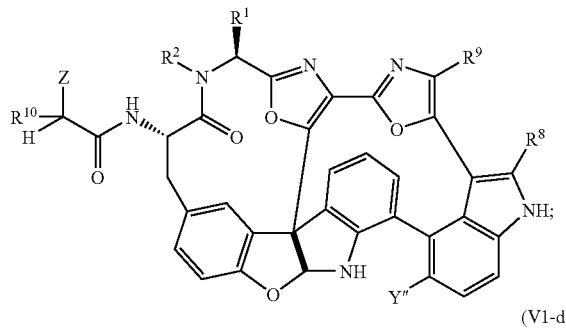

(V1-d)
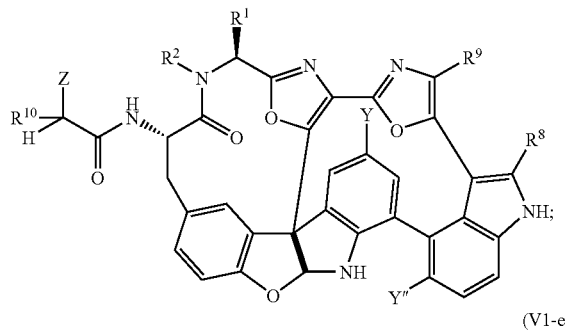

(V1-e)
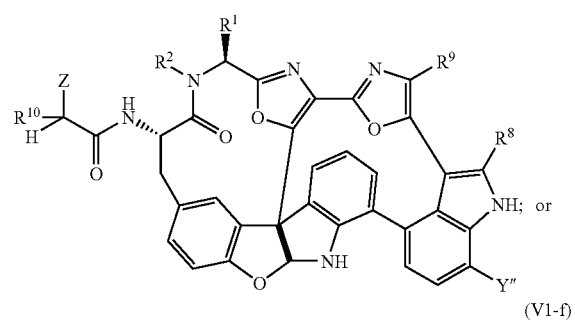

(V1-f)
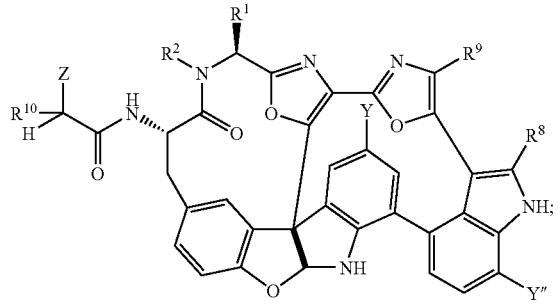

or a pharmaceutically acceptable salt or conjugate thereof;

wherein $R^1$, $R^2$, $R^8$, $R^9$, Y, Y", Z, and $R^{10}$ are defined as for formula (VI).

The present invention specifically excludes the compounds of formula:

Diazonamide A
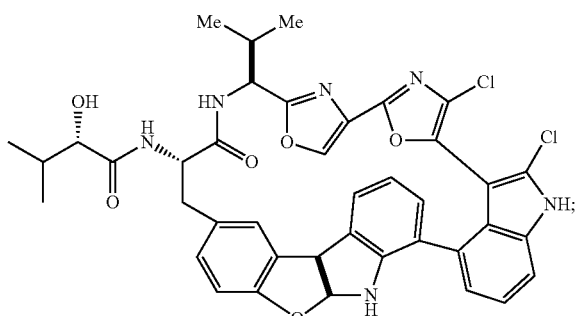

Diazonamide B
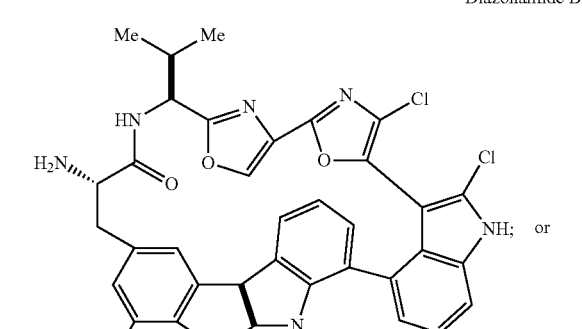

Compound J
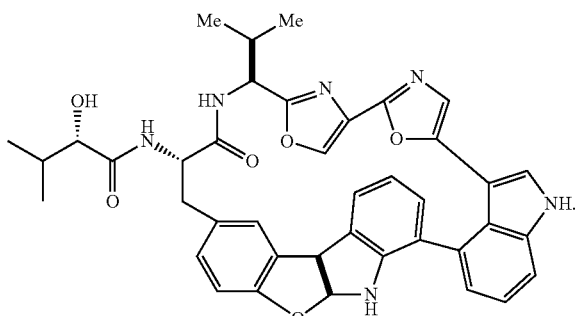

Where chiral carbons are included in chemical structures, unless a particular orientation is depicted, both stereoisomeric forms are intended to be encompassed. Compounds of formulae (I), (II), (III), (IV), (V) and (VI) may, for example, have two or more asymmetric centers and therefore exist in different enantiomeric and/or diastereomeric forms. All optical isomers and stereoisomers of the compounds described herein, and mixtures thereof, are considered to be within the scope of the invention, including the racemate, one or more enantiomeric forms, one or more diastereomeric forms, or mixtures thereof. In particular, racemic mixtures of single diastereomers such as the ones described, diastereomers having an diastereomeric excess (d.e.) of greater than 90% or greater than about 95%, and enantiomers having an enantiomeric excess (e.e.) of greater than 90% or greater than about 95%. Similarly, where double bonds are present, the compounds can exist in some cases as either cis or trans isomers;

the invention includes each isomer individually as well as mixtures of isomers. Where the compounds described may also exist in tautomeric forms, this invention relates to the use of all such tautomers and mixtures thereof.

Compounds of formulae (I), (II), (III), (IV), (V) and (VI) can be supplied in free base form, or can be supplied as a pharmaceutically acceptable salt, or as a mixture of the free base form and the corresponding salt. The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases that could be used include trimethylamine, triethylamine, pyridine, picoline, ethanolamine, diethanolamine, triethanolamine, dicyclohexylamine, N,N'-dibenzylethylenediamine, etc.

Suitable salts include those of inorganic acids such as hydrochlorides, hydrobromides, sulfates, hydrosulfates, and the like, or organic acid addition salts. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, compounds of formulae (I), (II), (III), (IV), (V) and (VI) may be coupled to moieties such as targeting agents. Among such targeting agents are antibodies or immunologically active fragments thereof, including single-chain antibody forms directed against tumor antigens or against receptors or integrins associated with tumors, peptidomimetics directed against these moieties, and the like. In addition, compounds of formulae (I), (II), (III), (IV), (V) and (VI) may be coupled to an excipient such as polyethylene glycol for altering pharmacokinetics. The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa.

Compounds of formulae (I), (II), (III), (IV), (V) and (VI) are useful in treating or ameliorating cell proliferative diseases. In particular, the compounds and methods described herein are useful for the treatment or amelioration of tumors and malignancies associated with breast, ovary, lung (SCLC and NSCLC), colon, rectum, prostate, testes, skin (e.g., melanoma, basal cell carcinoma, and squamous cell carcinoma), pancreas, liver, kidney, brain (e.g., glioma, meningioma, schwannomas, and medulloblastomas), and the blood and hematopoietic system, including, e.g., leukemia, non-Hodgkins lymphoma, and multiple myeloma.

In the methods described herein, for example, cell proliferation may be reduced, and/or cell death, such as apoptosis or apoptotic cell death, may be induced. The cell proliferative disorder may be a tumor or non-tumor cancer in a human or animal subject.

The compounds and methods provided herein for reducing cell proliferation and/or inducing cell death may be used alone, or in conjunction with or in combination with surgical, radiation, chemotherapeutic, immunotherapy, and bone marrow and/or stem cell transplantation methods, or with other palliative agents, such as compounds that aid in nutrition or general health, anti-emetic agents, and the like.

In some embodiments, the compounds of the present invention are administered in combination with a chemotherapeutic agent, and used to reduce cell proliferation, induce cell death, and/or treat or ameliorate a cell proliferative disorder.

The compounds described herein are also useful against certain drug resistant tumors and cancer cell lines, in particular against cancers that are resistant to TAXOL® and/or vinca alkaloid anti-cancer agents.

Where an additional chemotherapeutic drug is administered, it is typically one known to have cytostatic, cytotoxic or antineoplastic activity. These agents include, without limitation, antimetabolites (e.g., cytarabine, fludaragine, 5-fluoro-2'-deoxyuridine, gemcitabine, hydroxyurea, methotrexate); DNA active agents (e.g., bleomycin, chlorambucil, cisplatin, cyclophosphamide); intercalating agents (e.g., adriamycin and mitoxantrone); protein synthesis inhibitors (e.g., L-asparaginase, cycloheximide, puromycin); topoisomerase type I inhibitors (e.g., camptothecin, topotecan or irinotecan); topoisomerase type II inhibitors (e.g. etoposide, teniposide anthraquinones, anthracyclines and podophyllotoxin); microtubule inhibitors (e.g., taxanes, such as paclitaxel and docetaxel, colcemid, colchicines, or vinca alkaloids, such as vinblastine and vincristine); kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), TRAIL, a TRAIL receptor antibody, TNF-α or TNF-β, and/or radiation therapy.

In some preferred embodiments, the additional cancer therapeutic agent is TRAIL, a TRAIL receptor antibody, TNF-α or TNF-β. In other preferred embodiments, the additional drugs for co-administration with the compounds of the invention affects Hsp90 (heat-shock protein 90).

Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets*, 3, 359-69 (2003), and in Yamamoto, et al., *Angew. Chem.*, 42, 1280-84 (2003); and in Moulin, et al., *J. Amer. Chem. Soc.*, vol 127, 6999-7004 (2005); purine derivatives such as PU3, PU24FCl and PUH64 (see Chiosis et al., *ACS Chem. Biol.* Vol. 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.*, vol. 15, 3338-43 (2005). Antibodies or antibody fragments that selectively bind to Hsp90 may also be administered as drugs to cause inhibition of Hsp90, and can be used in combination with the compounds of the invention.

Where a compound described herein is utilized in conjunction with or in combination with another therapeutic, the two agents may be co-administered, or they may be administered separately where their administration is timed so the two agents act concurrently or sequentially.

Accordingly, the compositions used in the methods described herein include at least one compound of the invention, and can optionally include one or more additional cytotoxic or cytostatic therapeutic such as, but not limited to, those disclosed above. Similarly, the methods of the invention include methods wherein a subject diagnosed as in need of treatment for cancer is treated with at least one compound or composition of the invention, and is simultaneously or concurrently treated with one or more of the additional therapeutic agents described above.

Formulation and Administration

The formulations useful in the invention include standard formulations such as those set forth in *Remington's Pharmaceutical Sciences*, latest edition, Mack Publishing Co., Easton, Pa., incorporated herein by reference. Such formulations include those designed for oral delivery, slow release, topical administration, parenteral administration, or any other suitable route as determined by an attending physician or veterinarian. Thus administration may be systemic or local. Suitable vehicles or excipients include liposomes, micelles, nanoparticles, polymeric matrices, buffers, and the full range of formulations known to practitioners.

Formulations of the compounds and compositions of the invention may be prepared in a manner suitable for systemic administration or topical or local administration. Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery may also be appropriate for some of the compositions and methods of the invention. Thus the compositions of the invention may be administered transmucosally using technology and formulation methods that are known in the art.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or salt or conjugate thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

For administration to animal or human subjects, the dosage of a compound of the invention is typically 1-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

Synthetic Processes

Diazonamide analogs of formula (I) were prepared through a novel and efficient multi-step process, as shown in Scheme 1 and Scheme 2 and exemplified throughout the Examples. A key step in the process of forming the macrocyclic structure of these compounds involved the electrochemical oxidative cyclization of a phenolic intermediate to provide the macrocyclic indoline intermediate. This transformation has been described in U.S. application Ser. No. 12/134,984, filed Jun. 6, 2008, published as US 2009/0005572, the contents of which are incorporated herein by reference in their entirety.

As shown in Scheme 1, dipeptide starting materials were prepared under standard conditions known in the art, for example, by coupling an N-hydroxysuccinimide ester or another activated ester of a protected amino acid with serine. It will be understood by one of skill in the art that a wide variety of suitable conditions may be utilized to form the dipeptide starting materials, including the extensive body of literature describing synthesis of peptides and peptide mimetics.

The dipeptide was reacted with an optionally substituted indole and an activating reagent, optionally in the presence of a protic acid, to provide an indole-containing dipeptide. Suitable activating reagents include, for example, carboxylic acid anhydrides, mixed anhydrides, or acyl halides (e.g., acetic anhydride, trifluoroacetic anhydride, acetyl chloride, oxalyl chloride), sulfonic acid anhydrides or halides (e.g., methanesulfonic anhydride, trifluoromethanesulfonic anhydride, methanesulfonyl chloride), mineral acid halides (e.g., thionyl chloride, or phosphoryl chloride), and the like.

In a preferred embodiment, the activating agent was acetic anhydride, and the reaction was conducted in acetic acid as a protic solvent. In a particularly preferred embodiment, the dipeptide and an optionally substituted indole were reacted with acetic anhydride in acetic acid at about 80° C., to provide the desired compound.

The preparation of N-acetyl tryptophan derivatives by reaction of serine or N-acetyl serine and an optionally substituted indole in acetic anhydride and acetic acid has been previously reported. Y. Yokoyama, et al., *Tetrahedron Letters* (1999), 40: 7803; Y. Yokoyama, et al., *Eur. J. Org. Chem.* (2004), 1244; Y. Konda-Yamada, et al., *Tetrahedron* (2002), 58: 7851; M. W. Orme, et al., U.S. Pat. No. 6,872,721. However, the preparation of other acylated tryptophan derivatives under these conditions, such as the dipeptide analogs of the present invention, has not been described to our knowledge.

Esterification of the free carboxylic acid, followed by oxidative cyclization of the dipeptide intermediate with an oxidizing agent, for example, DDQ, provided an oxazole intermediate. It will be understood by those in the art that other oxidative conditions could be utilized, such as, for example, 7,7,8,8-tetracyanoquinodimethane (TCNQ), ceric ammonium nitrate, hypervalent iodide reagents, and the like.

Deprotection of the protected amino group and amide bond formation provided a phenolic intermediate. Electrochemical oxidative cyclization of the phenolic intermediate provided a macrocyclic indoline compound. Such compounds can be further elucidated to compounds of formula (I). A representative synthesis is shown in Scheme 2. Deprotection of the carboxylate ester followed by amide bond formation installed the indole ring. Cyclization to provide an oxazole intermediate, followed by an oxidative photochemical cyclization provided macrocyclic intermediates. Straightforward functional group manipulations provide compounds of formula (I). Following removal of the phenolic group used to direct the cyclization, the Cbz protecting group was removed. Standard functional group reactions, such as for example by acylation, amide coupling, sulfonylation, alkylation, reductive alkylation, and the like, may be used to install the substituents at $R^4$ and/or $R^5$.

Those skilled in the art will appreciate that certain reaction conditions can be varied without altering the essence of the present invention. For example, coupling reactions can be accomplished with a variety of activated esters, such as by way of example only N-hydroxybenzotriazole ester, perfluorophenyl ester, N-hydroxyphthalimide esters, activated esters generated by the reaction of the carboxylic acid with a carbodiimide, and other activated esters conventionally used for acylation of an amine to form amide bonds. It will be understood by one of skill in the art that the representative routes shown may be modified, for example by the use of different protecting groups on the amine, indole, and/or indoline nitrogen atoms, or on functionality present elsewhere in the molecule (for example, as substituent Y). Suitable protecting groups and methods to attach and remove them are well known in the art, and are described, for example, in T. H. Greene, PROTECTIVE GROUPS IN ORGANIC SYNTHESIS, 2 ed.

The selection of orthogonal protecting groups for polyfunctional molecules is known in the art. In the present methods, while amino groups are conveniently protected as carbobenzyloxy (Cbz) group, one of skill in the art will recognize that other suitable protecting groups could be utilized. It will be further understood that the methods shown herein include an optional deprotection step or steps to remove protecting groups present in the molecules. It will be understood by one of skill in the art that compounds of formulae described herein can be prepared by modification of Schemes 1 and 2, for example by deprotection of the protected amine in Scheme 2 and amide bond formation to install an appropriate acyl substituent, for example, the group —C(O)$R^3$ or —C(O)C(Z)$R^{10a}R^{10b}$ or —C(O)CH(Z)$R^{10}$ at $R^5$ in formula (I).

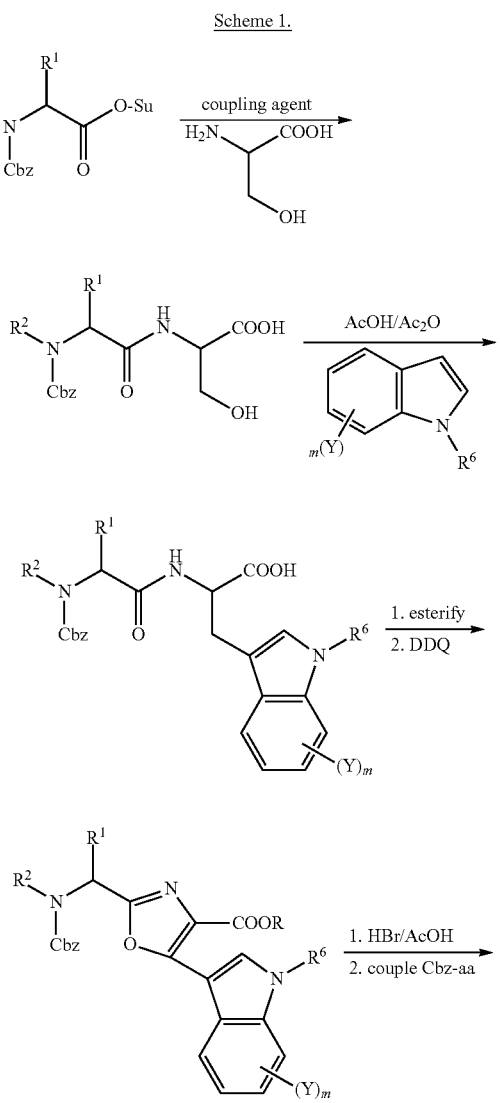

Scheme 1.

39
-continued
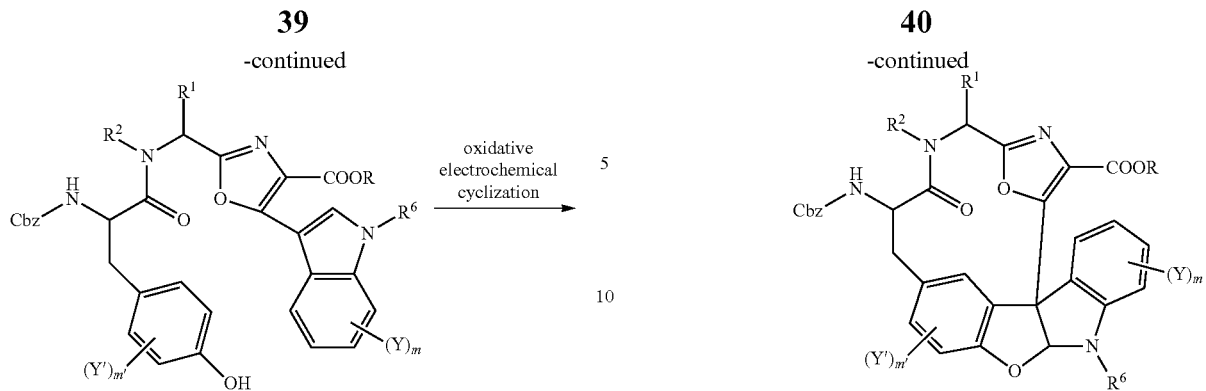
oxidative electrochemical cyclization
40
-continued
Scheme 2.
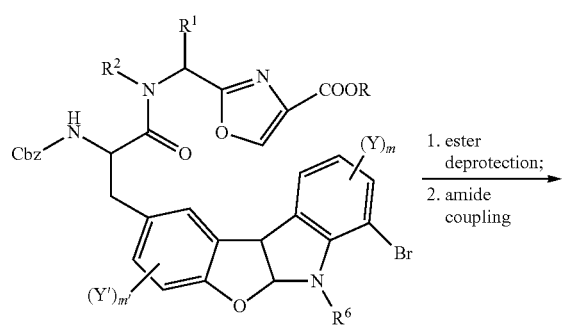
1. ester deprotection;
2. amide coupling
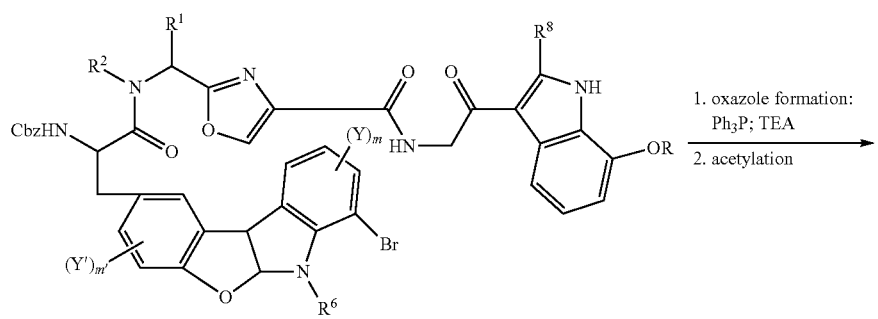
1. oxazole formation: Ph₃P; TEA
2. acetylation
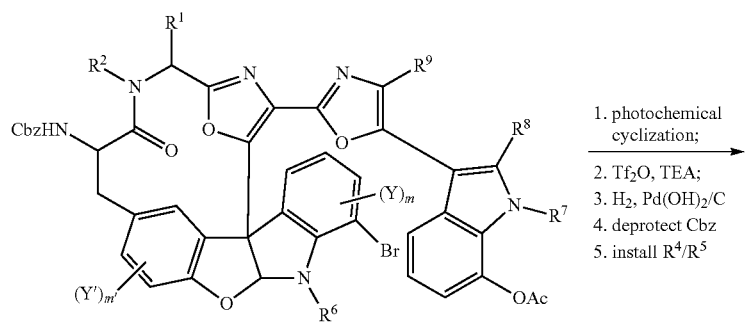
1. photochemical cyclization;
2. Tf₂O, TEA;
3. H₂, Pd(OH)₂/C
4. deprotect Cbz
5. install $R^4/R^5$

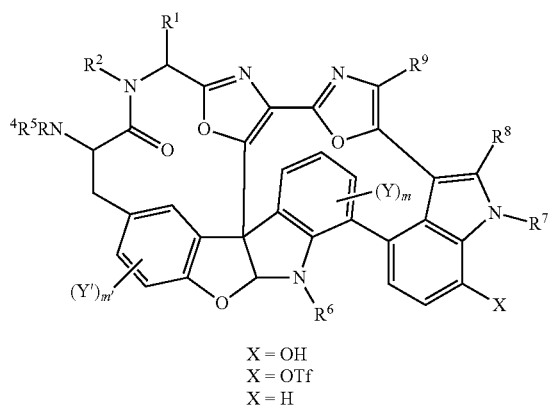

X = OH
X = OTf
X = H

Compound of the formulae described herein are available in high yield and purity. In particular, the compounds of the present invention are available in good yield and with high diastereomeric purity, preferably in greater than 95% diastereomeric excess, sometimes greater than 98% diastereomeric excess.

Mass spectrometry (MS) was conducted with various techniques. Mass spectra were typically obtained using liquid chromatograph electrospray ionization mass spectrometry, MS (ESP).

The following examples are offered to illustrate but not to limit the invention.

Example 1

7-Bromoindole

2-Bromonitrobenzene (1.10 kg, 5.45 mol) was dissolved in THF (10 L) at RT. This solution was cooled with stirring in a bath maintained at −78° C. When the internal temperature reached −40° C., vinylmagnesium bromide (16.3 L, 16.3 mol) was added at such a rate as to maintain the internal temperature at −40° C. during the addition. Upon complete addition, the reaction was removed from the bath and allowed to warm slowly to −30° C. over the course of 45 min. This required occasional cooling. The −30° C. reaction solution was quenched by rapid addition of a slightly cool (~10° C.) solution of saturated aqueous $NH_4Cl$ (10 L). Slight foaming occurred (inverse quench into the $NH_4Cl$ solution is also satisfactory). This resulted in a biphasic mixture with some undissolved magnesium salts in the form of a gel. The mixture was stirred for 30 min and the layers were separated. The aqueous layer was back extracted with THF (10 L). The combined organic layers were evaporated at reduced pressure with a bath temperature of 35° C. and the resulting dark oil was taken up in $CH_2Cl_2$ (5 L) and dried with $Na_2SO_4$. The mixture was filtered and concentrated. The resulting material was chromatographed, eluting with 2% EtOAc-hexanes to give 7-bromoindole (557 g, 52% yield) as an off-white solid. $^1H$ NMR ($CDCl_3$): consistent with proposed structure.

Example 2

Cbz-Val-Ser-OH

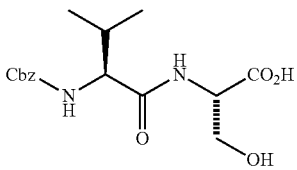

L-Serine (104.19 g, 991 mmol) was dissolved in water (1440 mL) in a 4-L Erlenmeyer flask. Solid $NaHCO_3$ (83.25 g, 991 mmol) was added and the mixture was stirred at RT to give a clear solution. Cbz-Val-OSu (300.0 g, 861 mmol) was added as a solution in 1,4-dioxane (1500 mL), with additional 1,4-dioxane (220 mL) used to rinse. The resulting cloudy mixture became clear after 1.5 h of stirring at 25° C. After 44 h, the mixture was divided into two equal portions. Methanol (700 mL) and 12 N aqueous HCl (42 mL, 504 mmol) were added to each portion, followed by EtOAc (1000 mL) and a solution of NaCl (100 g) dissolved in water (600 mL). The layers were separated and the organic layer was washed with saturated aqueous NaCl (350 mL). The aqueous layers were extracted in succession with EtOAc (1000 mL). The organic layers resulting from work-up of both portions of the reaction were combined, dried ($Na_2SO_4$), filtered, and evaporated to give a white solid (351 g). This material was suspended in $CH_2Cl_2$ (1500 mL) and stirred for 2 h. The mixture was filtered and the crystals were washed with $CH_2Cl_2$ (1000 mL) to give Cbz-Val-Ser-OH as white crystals (262.3 g, 90% yield). $^1$H NMR (300 MHz, DMSO-$d_6$): consistent with proposed structure. MS: m/z=339.1 (M+1).

Example 3

Cbz-Val-(7-Bromo-Trp)-OH

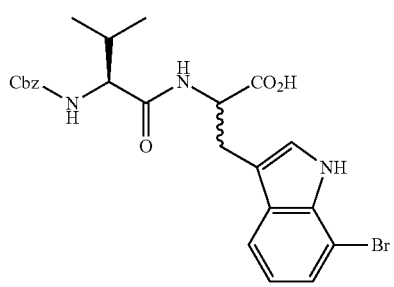

Acetic acid (180 mL) was added to Cbz-Val-Ser-OH (42.89 g, 127 mmol) from Example 2 and 7-bromoindole (30.96 g, 158 mmol) from Example 1 in a round-bottom flask fitted with a mechanical stirrer, reflux condenser, and internal thermometer. Acetic anhydride (40 mL, 43 g, 420 mmol) was added and the mixture was heated to 80° C. over 40 min. Heating was continued at this temperature for 4 h. After cooling to RT and standing overnight, the mixture was diluted with ethyl ether (180 mL) and stirred for 30 min. The mixture was filtered and the crystals were washed with ethyl ether (250 mL). Drying of the crystals yielded Cbz-Val-(7-bromo-Trp)-OH (42.49 g, 65% yield). $^1$H NMR (300 MHz, DMSO-$d_6$): consistent with proposed structure. MS: m/z=516.0 (M+1).

Example 4

Cbz-Val-(7-Bromo-Trp)-OMe

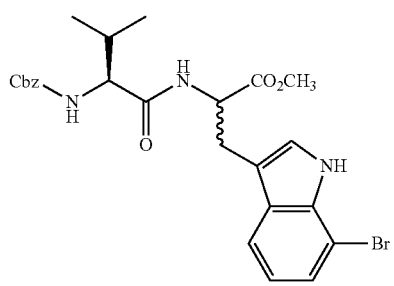

Concentrated aqueous HCl (60 mL, 720 mmol) was added to a stirred suspension of Cbz-Val-(7-bromo-Trp)-OH (32.53 g, 63.0 mmol) from Example 3 in 2,2-dimethoxypropane (1200 mL, 1020 g, 9.8 mol). After stirring for 24 h at 25° C., most of the solvent was evaporated to give wet crystals. MTBE (250 mL) was added and the mixture was allowed to stand with occasional swirling over 3 h. Filtration and washing of the crystals with MTBE (100 mL) gave Cbz-Val-(7-bromo-Trp)-OMe (30.31 g, 91% yield). $^1$H NMR (300 MHz, DMSO-$d_6$): consistent with proposed structure. MS: m/z=530.1 (M+1).

Example 5

Methyl 2-((S)-1-(benzyloxycarbonylamino)-2-methylpropyl)-5-(7-bromo-1H-indol-3-yl)oxazole-4-carboxylate

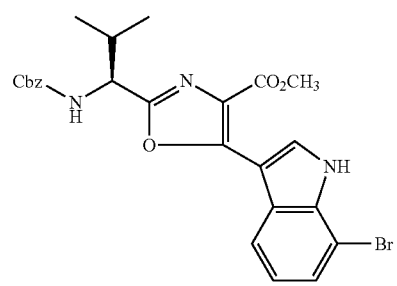

A solution of DDQ (28.41 g, 125 mmol) in THF (251 g, 282 mL) was added to Cbz-Val-(7-bromo-Trp)-OMe (30.20 g, 56.9 mmol) from Example 4 in THF (848 g, 954 mL) and the dark solution was heated to gentle reflux in an oil bath at 85° C. for 6 h. After cooling and standing overnight at RT, the solvent was removed on a rotary evaporator. Methanol (200 mL) was added and the solvent was evaporated to leave a brown crusty solid (91 g). Methanol (200 mL) was added and the solid was loosened with a spatula. The mixture was swirled until the appearance changed to a red liquid containing a yellow precipitate. The mixture was filtered and the precipitate was washed with methanol (60 mL). The pale gray crystals were air dried and then dried under vacuum to give methyl 2-((S)-1-(benzyloxycarbonylamino)-2-methylpropyl)-5-(7-bromo-1H-indol-3-yl)oxazole-4-carboxylate (17.98 g, 60% yield). $^1$H NMR (300 MHz, DMSO-$d_6$): consistent with proposed structure. MS: m/z=526.0 (M+1).

Example 6

Methyl 2-((S)-1-amino-2-methylpropyl)-5-(7-bromo-1H-indol-3-yl)oxazole-4-carboxylate hydrobromide

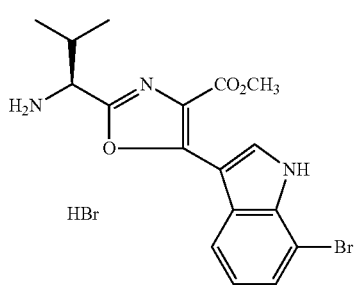

Glacial acetic acid (25 mL) was added to methyl 2-((S)-1-(benzyloxycarbonylamino)-2-methylpropyl)-5-(7-bromo-1H-indol-3-yl)oxazole-4-carboxylate (9.99 g, 19.0 mmol) in a 500-mL round-bottom flask fitted with a mechanical stirrer. The suspension was stirred at 25° C. and 33% HBr in acetic acid (50 mL) was added in one portion. The mixture became homogeneous and then a precipitate formed in 5-10 min.

After 1 h, MTBE (235 mL) was added and stirring was continued at 25° C. for another 1 h 20 min. The mixture was filtered and the precipitate was washed with MTBE (150 mL). The cream-colored powder was dried under vacuum to give methyl 2-((S)-1-amino-2-methylpropyl)-5-(7-bromo-1H-indol-3-yl)oxazole-4-carboxylate hydrobromide (8.91 g, 99% yield). $^1$H NMR (300 MHz, DMSO-d$_6$): consistent with proposed structure. MS: m/z=392.0 (M+1).

Example 7

Methyl 2-((S)-1-((S)-2-(benzyloxycarbonylamino)-3-(4-hydroxyphenyl)propanamido)-2-methylpropyl)-5-(7-bromo-1H-indol-3-yl)oxazole-4-carboxylate

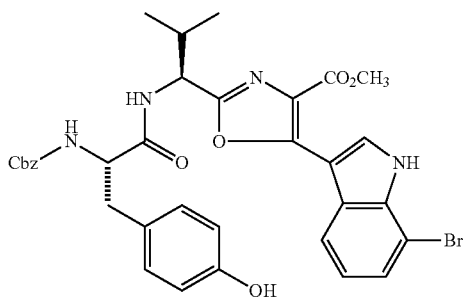

DMF (100 mL) was added to methyl 2-((S)-1-amino-2-methylpropyl)-5-(7-bromo-1H-indol-3-yl)oxazole-4-carboxylate hydrobromide (9.16 g, 19.4 mmol), HOBt (3.17 g, 23.5 mmol), and Cbz-Tyr-OH (6.44 g, 20.4 mmol) in a round-bottom flask. N,N-Diisopropylethylamine (4.22 mL, 3.13 g, 129 mmol) was added, followed by EDC (4.15 g, 21.6 mmol). After stirring for 24 h at 25° C., the solution was diluted with EtOAc (500 mL) and the mixture was washed with 1 N aqueous HCl (250 mL), saturated aqueous NaHCO$_3$ (250 mL), and saturated aqueous NaCl (250 mL). The solution was dried (Na$_2$SO$_4$), decanted, and evaporated to give a tan solid. This material was dissolved in 2-PrOH (180 mL) at 90° C. Hexanes (85 mL) were added and the solution was allowed to cool to RT. After standing overnight, the mixture was cooled to 5° C. for 4 h. The solid was separated by filtration and washed with 1:1 2-PrOH/hexanes (140 mL). This material, which at this point held residual solvent, was dried on a vacuum manifold to give methyl 2-((S)-1-((S)-2-(benzyloxycarbonylamino)-3-(4-hydroxyphenyl)propanamido)-2-methylpropyl)-5-(7-bromo-1H-indol-3-yl)oxazole-4-carboxylate (11.58 g, 87% yield). $^1$H NMR (300 MHz, DMSO-d$_6$): consistent with proposed structure. MS: m/z=689.0 (M+1).

Example 8

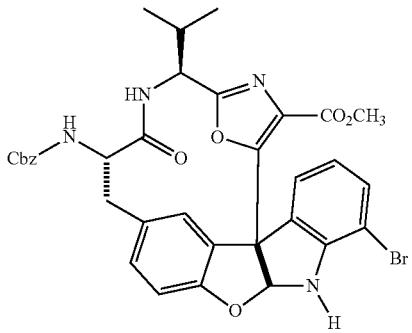

An electrochemical cell was assembled using a polyethylene cylinder (15 cm diameter×30 cm height) and a custom rack (polypropylene and nylon) which supported 48 vertical graphite rods (6.15 mm diameter×30 cm length). The rods were arranged in a pattern of three concentric rings with 12 and 24 anodes in the inner and outer rings, respectively. The intermediate ring contained 12 cathodes, separated from adjacent anodes by approximately 7 mm. Electrodes were immersed to a depth of 24 cm. The phenolic material synthesized in Example 7 (20.00 g, 29.0 mmol) and Et$_4$NBF$_4$ (70.00 g, 322 mmol) were dissolved in DMF (4000 mL), and. KOH (~86%, 1.68 g, 26 mmol) was added in 10 mL of water. The solution was stirred vigorously by two 4-bladed turbines (50 mm diameter, blades at 45°, approx. 680 rpm) on a single shaft. The electrochemical reaction was carried out at a potential of 1.5-1.6 volts. Additional phenolic starting material (20.00 g, 20.00 g, 20.00 g, and 7.94 g) was added as a solid, along with KOH (~86%, 1.60 g, 1.63 g, 1.53 g, and 0.65 g) in water (5.0 mL, 5.0 mL, 5.0 mL, and 2.0 mL) on days 3, 5, 8, and 10, respectively. After 13 days, approximately 27.7 amp-h of current had passed, and 5.8% of the original SM remained as determined by HPLC integration at 220 nM. The reaction mixture was concentrated on a rotary evaporator (bath temp. ≦35° C.) and dried further on a vacuum manifold. The residue was partitioned between EtOAc (1200 mL) and 0.5 N aqueous HCl (600 mL). The organic layer was washed with saturated aqueous NaHCO$_3$ (250 mL) and then saturated aqueous NaCl (250 mL). The aqueous layers were extracted in succession with EtOAc (2×250 mL). The combined organic layers were dried (Na$_2$SO$_4$), decanted and evaporated to give 70.1 g of crude product. This material was purified by flash column chromatography in three portions. Each portion used silica gel (283 g) with 25% EtOAc in CH$_2$Cl$_2$ (approx. 2.4 L for packing column and elution). This yielded 35.6 g (41% yield) of product as a mixture of stereoisomers (83.5: 13.6 as measured by HPLC integration at 220 nM). MTBE (500 mL) was added and the mixture was stirred at RT for 2 h. After standing an additional 3 h, the mixture was filtered and the solid was washed with MTBE (3 portions, 100 mL total). HPLC analysis of the filtrate showed 94.8% purity (94.8:2.1 stereoisomer ratio measured by integration at 220 nm). The filtrate was evaporated and the resulting residue was dried under vacuum to yield 31.99 g of product (36% yield) of as a pale yellow solid. MS: m/z=687.0 (M+1).

Example 9

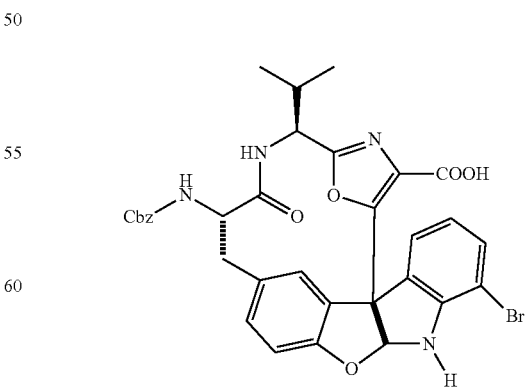

To a three-neck round-bottom flask equipped with a thermometer, an addition funnel and a magnetic stir bar was added the methyl ester synthesized in Example 8 (530 mg, 0.77 mmol) and methanol (18 mL). The solution was cooled to 0° C. in an ice-water bath followed by addition of LiOH in water (324 mg/5 mL, 7.7 mmol) at 0° C. with stirring. After the addition the reaction mixture became a slurry. The cooling bath was removed and the mixture was allowed to warm to RT. The precipitate disappeared gradually. After 4.5 h stirring at RT less than 2% of SM remained as determined by LCMS. Ice (40 g) was added to the reaction mixture and 1 N aqueous HCl (10 mL) was added dropwise from an addition funnel with vigorous stirring to acidify the 0° C. reaction mixture. The pH of the mixture was adjusted to 2.5-3.0. A pale yellow solid precipitated, which was extracted using EtOAc (2×50 mL). The aqueous phase was concentrated to remove most of the methanol and then extracted with EtOAc (2×50 mL). The combined organic layers was dried over $Na_2SO_4$ and concentrated to afford crude product (516 mg, 0.77 mmol, ca. 96% pure and containing by-product hydantoin) which was used directly in the next step without further purification. MS: m/z=673.2 (M+1).

Example 10

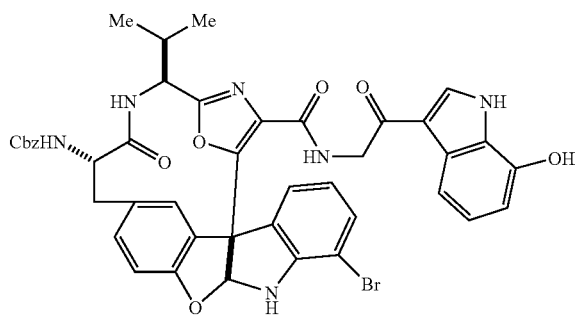

To a dry 250-mL round-bottom flask with magnetic stir bar was added DHOBt (545 mg, 3.34 mmol), EDC (2.75 g, 14.32 mmol), anhydrous DMF (130 mL) and TEA (2.0 mL, 14.32 mmol). The resulting reagent mixture was stirred for 20 min. To another dry 500-mL round-bottom flask was added the crude product from Example 9 (6.43 g, 9.6 mmol), 2-amino-1-(7-hydroxy-1H-indol-3-yl)ethanone hydrochloride (3.25 g, 14.32 mmol) and DMF (30 mL). Then TEA (2.0 mL, 14.32 mmol) was added dropwise followed by the addition of the reagent mixture above. The resulting reaction mixture was stirred for 6 h at 40-42° C. and cooled to RT overnight. About 4% of starting acid remained as determined by LCMS. Most of DMF was removed under vacuum at 45° C. Less than 1% of starting material remained. The residue was diluted with EtOAc (800 mL)/water (200 mL). Some undissolved brown solid was removed by filtration. The organic phase was separated and the aqueous phase was extracted by EtOAc (2×100 mL). The combined organic layers were washed with water (100 mL), 10% aqueous $NaHSO_4$ (100 mL), water (100 mL), saturated $NaHCO_3$ (100 mL), water (2×100 mL) and brine (100 mL), and then dried over $Na_2SO_4$. After concentration the crude product (8.4 g, 9.6 mmol) was obtained and used directly in next step without further purification. $^1$H NMR (400 MHz, $CDCl_3$): consistent with proposed structure. MS: m/z=845.1 (M+1).

Example 11

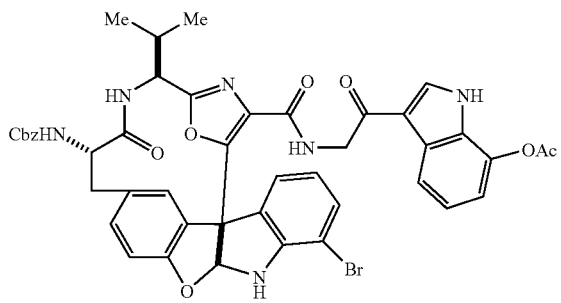

To a dry 500-mL flask containing crude product from Example 10 (8.4 g, 9.6 mmol) was added anhydrous THF (40 mL) and anhydrous $CH_2Cl_2$ (150 mL). The resulting solution was cooled to 0° C. in an ice-water bath. Acetic anhydride (2.69 mL, 28.65 mmol) and pyridine (1.16 mL, 14.33 mmol) were added sequentially at 0° C. Then the mixture was allowed to warm to RT and stirred under $N_2$. The reaction was monitored using LCMS. After 3.5 h only 2% of starting material was not consumed and 2% of over-acetylated product was formed. The reaction solution was diluted with EtOAc (700 mL) followed by washing with water (3×100 mL) and brine (100 mL) and drying over $Na_2SO_4$. After concentration, the crude compound product was purified by flash chromatography eluting with a EtOAc-$CH_2Cl_2$ gradient (30/70 to 35/65) to afford desired product (4.56 g, 5.14 mmol, 51% yield over three steps). $^1$H NMR (400 MHz, $CDCl_3$): consistent with proposed structure. MS: m/z=887.1 (M+1).

Example 12

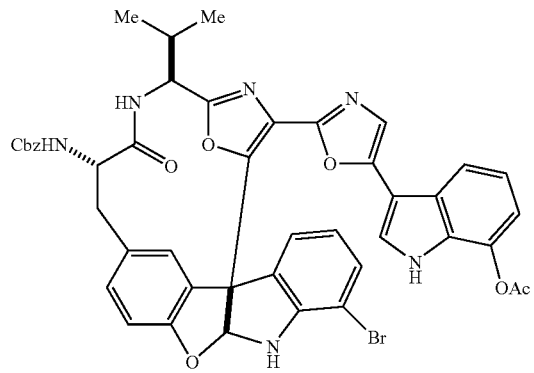

Triphenylphosphine (13.48 g, 51.4 mmol) and hexachloroethane (12.17 g, 51.4 mmol) were added to a dry 1-L three-neck round-bottom flask equipped with a thermometer, an addition funnel and a magnetic stir bar. Anhydrous $CH_2Cl_2$ (320 mL) was added and the resulting solution was cooled to 10° C. in an ice-water bath under $N_2$. TEA (10.03 mL, 71.96 mmol) was added slowly to the solution, followed by stirring for 10 min at 10° C. The solution of the product from Example 11 (4.56 g, 5.14 mmol) in anhydrous $CH_2Cl_2$ (160 mL) was added dropwise over 5 min. and the temperature was kept at 10-12° C. The reaction mixture was stirred at 10° C. for another 10 min, and TLC showed that no starting material left. The reaction mixture was cooled to −30° C. followed by addition of phosphate buffer (200 mL, pH=6.9, 0.5 μl) to consume excess reagents. The resulting reaction mixture was stirred in cold room (4° C.) for 48 h. Most of triphenylphosphine was consumed as determined by LCMS. The organic phase was separated and the aqueous phase was extracted by $CH_2Cl_2$ (2×100 mL). Combined organic phase was washed with water (100 mL) and brine (100 mL) and dried over $Na_2SO_4$. All solvent was removed under reduced pressure on a rotary evaporator followed by the addition of EtOAc (40 mL) to precipitate triphenylphosphine oxide. After filtering and washing with $CH_2Cl_2$, the filtrate was concentrated. The crude compound was purified by flash chromatography eluting with EtOAc/toluene (60/40; column 4×28 cm) to give desired compound (3.41 g, 3.92 mmol, 76% yield). $^1$H NMR (400 MHz, $CDCl_3$): consistent with proposed structure. MS: m/z=869.1 (M+1).

Example 13

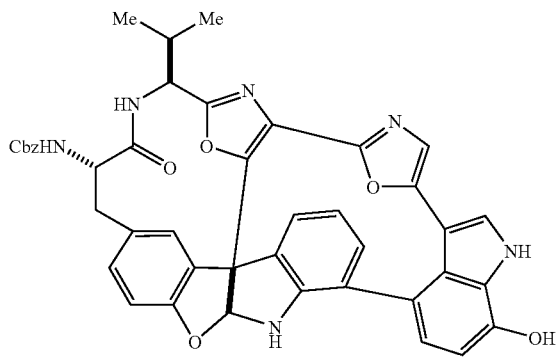

The solution of the product from Example 12 (1.2 g, 1.38 mmol) in acetonitrile (400 mL) was added to a 500-mL flask of a Hanovia photoreactor in a photochemical safety cabinet. The solution was degassed by a stream of argon for 30 min. Then a pre-degassed aqueous solution of lithium hydroxide (83 mg/70 mL, 3.45 mmol) was added by syringe. The resulting solution was degassed again for another 1 h. The door of cabinet was closed. Then the water flow (for cooling the UV lamp) was turned on and UV lamp (with Pyrex filter) was turned on. The reaction solution was irradiated with UV for 120 min followed by quenching with 70 mL of saturated $NH_4Cl$. The organic phase was separated and the aqueous phase was extracted with EtOAc (2×100 mL). The combined organic phase was washed with brine (100 mL) and dried over $Na_2SO_4$. This photoreaction protocol was performed three times using a total of 3.41 g (3.92 mmol) of starting material. All crude product was combined and purified by flash chromatography eluting with an EtOAc-$CH_2Cl_2$ gradient (40:60 to 55:45) to afford desired product (1.29 g, 1.72 mmol, 44% yield). $^1$H NMR (400 MHz, $CDCl_3$): consistent with proposed structure. MS: m/z=747.2 (M+1). Deacetylated starting material (865 mg, 1.05 mmol, 27% yield) was recovered.

Example 14

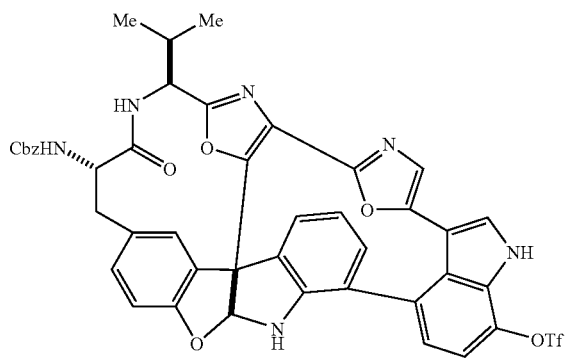

To a dry 250-mL two-neck round-bottom flask equipped with a thermometer containing the product from Example 13 (1.29 g, 1.72 mmol) was added anhydrous $CH_2Cl_2$ (100 mL) and TEA (0.719 mL, 5.16 mmol). The suspension was cooled to 0° C. in an ice-brine bath followed by addition of the solution of trifluoromethanesulfonic anhydride (0.407 mL, 2.41 mmol) in anhydrous $CH_2Cl_2$ (14 mL) dropwise at 0° C. The mixture was stirred at 0° C. under $N_2$ for 2 h and TLC showed that all starting material was consumed. Saturated $NaHCO_3$ (20 mL) was added to quench the reaction. The organic phase was separated, washed with water (30 mL) and brine (2×30 mL) and dried over $Na_2SO_4$. The solution was concentrated to afford the crude product (1.50 g, 1.71 mmol) which was used directly in next step without further purification. $^1$H NMR (400 MHz, $CDCl_3$): consistent with proposed structure. MS: m/z=879.2 (M+1).

Example 15

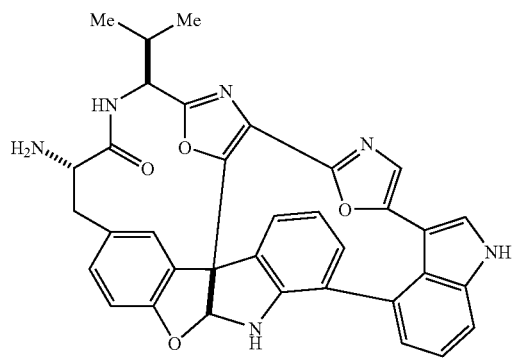

To a 250-mL round-bottom flask containing crude product from Example 14 (1.47 g, 1.67 mmol) was added methanol (75 mL) and TEA (0.838 mL, 6.0 mmol). The flask was purged with $N_2$ flow for 10 min followed by addition of 20% $Pd(OH)_2$/C (2.64 g) under $N_2$. A $H_2$ balloon was attached and the flask was purged with $H_2$ four times. Then the $H_2$-filled balloon was opened to the reaction system. After 6.5 h stirring about 5% of starting material remained. The reaction was stopped. The reaction mixture was filtered through a pad of Celite® and the black cake was washed with methanol (5×15 mL). The filtrate was concentrated and the residue was dissolved in $CH_2Cl_2$ (500 mL). The resulting solution was washed with water (3×100 mL) and brine (100 mL), and dried over $Na_2SO_4$. The solution was concentrated to afford the crude product (930 mg, 1.56 mmol) which was used directly in next step without further purification. $^1H$ NMR (400 MHz, $CD_3OD$): consistent with proposed structure. MS: m/z=597.2 (M+1).

Example 16

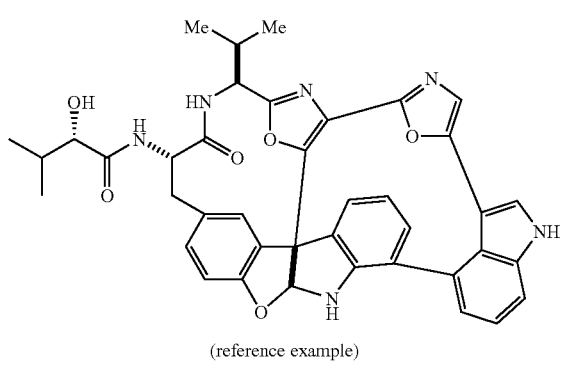

Compound J (reference example)

To a dry 100-mL round-bottom flask containing the product from Example 15 (930 mg, 1.56 mmol) was added anhydrous THF (45 mL). The solution of N-hydroxysuccinimide ester of (S)-2-hydroxy-3-methylbutyric acid (503 mg, 2.34 mmol) in anhydrous THF (4 mL) was added dropwise at RT under $N_2$. The resulting reaction solution was stirred for 18 h. Less than 5% of starting material remained. All solvent was evaporated under reduced pressure and the residue was dissolved in methanol (200 mL). The solution was cooled to 0° C. in an ice-water bath followed by the addition of aqueous KOH (1 N, 7 mL) to consume excess reagent. The solution was stirred at 0° C. for 30 min. Then saturated $NH_4Cl$ (40 mL) was added at 0° C. to neutralize the base. Most of the methanol was evaporated under reduced pressure and the residue was dissolved in EtOAc (500 mL) followed by washing with saturated $NaHCO_3$ (100 mL), water (2×100 mL) and brine (100 mL) and dried over $Na_2SO_4$. The solution was concentrated and the crude was purified by flash chromatography eluting with $EtOAc/CH_2Cl_2$ gradient (60/40, 70/30, 80/20 and pure EtOAc) to afford the desired product (563 mg, 0.808 mmol, 48% combined yield over three steps). $^1H$ NMR (500 MHz, $CD_3OD$): consistent with proposed structure. MS: m/z=697.2 (M+1).

Example 17

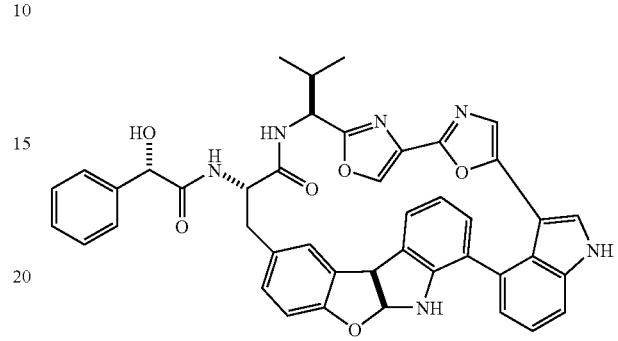

DMF (1.0 mL) was added to a reaction vial containing the compound synthesized in Example 15 (40 mg, 0.067 mmol), (S)-mandelic acid (11 mg, 0.072 mmol), and HOBt (11 mg, 0.081 mmol). A few 3 Å molecular sieve pellets were added and the mixture was stirred for 15 min before the addition of EDC (15 mg, 0.078 mmol). After 2.5 h, the reaction mixture was diluted into EtOAc (30 mL) and washed with 1 N aqueous HCl (15 mL), saturated aqueous $NaHCO_3$ (15 mL) and saturated aqueous NaCl (10 mL). The organic layer was dried over $Na_2SO_4$, decanted, and evaporated. The residue was purified by flash column chromatography on silica gel packed in 1:1 $EtOAc/CH_2Cl_2$, eluting with 3-4% MeOH in 1:1 $EtOAc/CH_2Cl_2$, to give 38 mg of the amide product. MS: m/z=731.1 (M+1).

Examples 18-29

The compounds in Examples 18-29 were prepared using coupling conditions similar to those used in Example 17, with the amine synthesized in Example 15 serving as the starting material. Coupling of this amine with a series of carboxylic acids produced the amide derivatives shown in Table 1.

TABLE 1

|  | LCMS m/z |
| --- | --- |
| Example 18 | 669.2 (M + 1) |

TABLE 1-continued

| | | LCMS m/z |
|---|---|---|
| Example 19 | [structure] | 711.2 (M + 1) |
| Example 20 | [structure] | 711.2 (M + 1) |
| Example 21 | [structure] | 737.1 (M + 1) |
| Example 22 | [structure] | 683.1 (M + 1) |

TABLE 1-continued
| | | LCMS m/z |
|---|---|---|
| Example 23 | 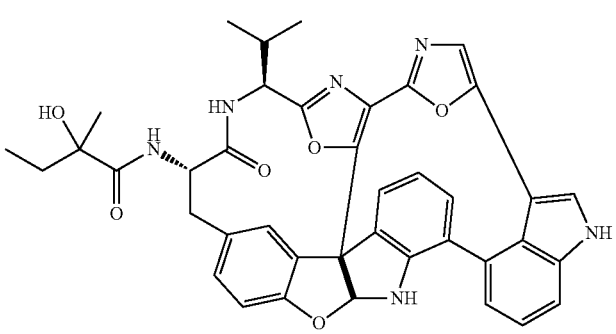 | 697.0 (M + 1) |
| Example 24 | 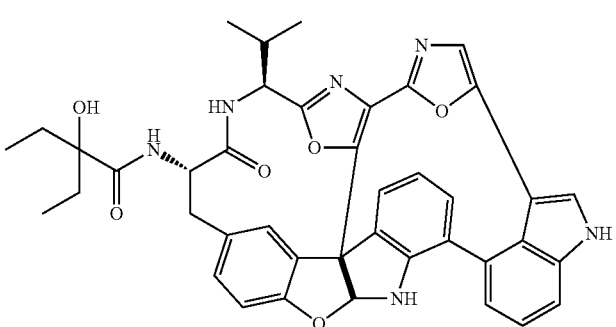 | 711.2 (M + 1) |
| Example 25 | 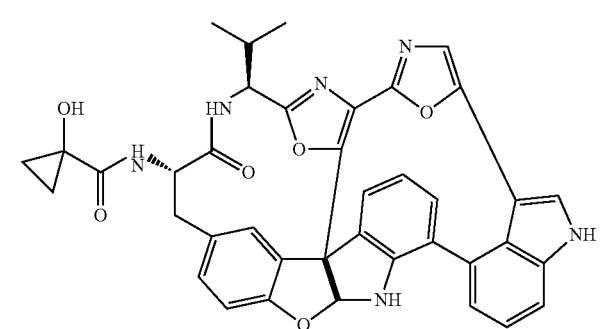 | 681.2 M + 1) |
| Example 26 | 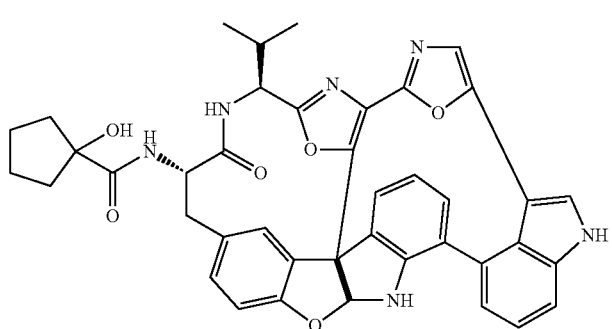 | 708.8 (M + 1) |

| | | LCMS m/z |
|---|---|---|
| Example 27 | | 722.7 (M + 1) |
| Example 28 | | 727.2 (M + 1) |
| Example 29 | | 864.2 (M + 1) |

Example 30

Step A

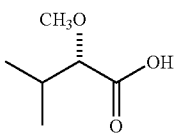

To a dry 15-mL flask were added NaH/mineral oil (60%, 116 mg, 2.91 mmol) and anhydrous hexane (10 mL). The mixture was stirred for 5 min and the upper hexane layer was removed using a syringe. Anhydrous THF (5 mL) was added. The mixture was cooled in 0° C. bath for 20 min. Then a solution of methyl (S)-3-methyl-2-hydroxybutyrate (350 mg, 2.65 mmol) in anhydrous THF (1 mL) was added dropwise at 0° C. over 10 min. After the addition, the mixture was stirred at 0° C. for 1 h following by the addition of iodomethane (0.198 mL, 3.18 mmol). The mixture was allowed to warm to RT and was stirred overnight. $^1$H NMR showed that there was no starting material left. The mixture was cooled to 0° C. and aqueous KOH (1 M, 5.4 mL, 5.4 mmol) was added dropwise followed by stirring at RT for 4 h. The resulting mixture was added to ice (10 g) and was neutralized by adding aqueous HCl (1 M, 5.5 mL, 5.5 mmol). The mixture was extracted by ether (3×15 mL), washed with brine (10 mL) and dried over $Na_2SO_4$. After concentration, the crude product (S)-3-methyl-2-methoxybutanoic acid (251 mg) was used in next step.

Step B

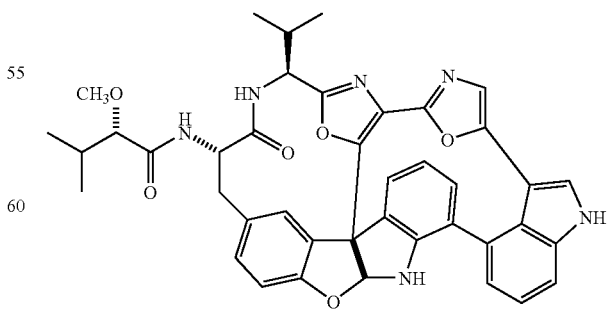

To a dry 15-mL flask with magnetic stir bar were added the amine synthesized in Example 15 (45 mg, 0.076 mmol), crude (S)-3-methyl-2-methoxybutanoic acid from step A above (12 mg, 0.091 mmol), HOBt (12.2 mg, 0.0908 mmol), N,N-diisopropylethylamine (0.0158 mL, 0.0908 mmol) and anhydrous DMF (1 mL), The reaction mixture was cooled to 0° C. followed by addition of EDC (17.4 mg, 0.0908). The resulting reaction mixture was stirred at RT for 18 h. The reaction was monitored by LCMS. The reaction mixture was diluted with EtOAc (30 mL)/water (10 mL). The organic phase was separated and the aqueous phase was extracted by EtOAc (2×10 mL). The combined organic layers were washed with water (20 mL), 10% aqueous $NaHSO_4$ (20 mL), water (20 mL), saturated $NaHCO_3$ (20 mL), and brine (2×20 mL), and then dried over $Na_2SO_4$. After concentration the crude product was purified by PTLC eluting with MeOH/$CH_2Cl_2$ (7/93) to afford desired product as an off-white solid (26 mg, 48%). MS: m/z=711.2 (M+1).

Example 31

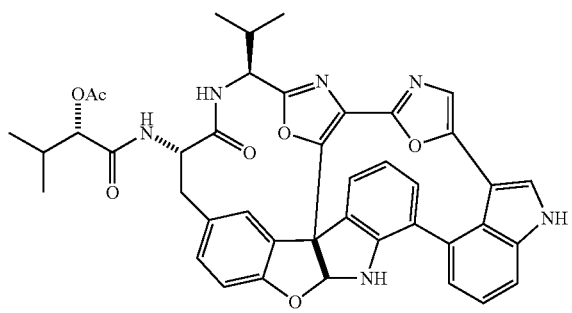

To a dry flask containing the material synthesized in Example 16 (9.2 mg, 0.013 mmol) were added anhydrous THF (0.2 mL) and anhydrous $CH_2Cl_2$ (0.5 mL). All solid dissolved. The solution was cooled in an ice-water bath for 20 min. Pyridine (0.0085 mL, 0.11 mmol) and acetic anhydride (0.0124 mL, 0.132 mmol) were added at 0° C. The resulting reaction mixture was allowed to warm to RT and was stirred overnight. The mixture was diluted with EtOAc (20 mL), washed with water (2×10 mL) and brine (10 mL), and dried over $Na_2SO_4$. After concentration the crude product was purified by PTLC eluting with MeOH/$CH_2Cl_2$ (10/90) to afford desired product as an off-white solid (5 mg, 51%). MS: m/z=739.3 (M+1).

Example 32

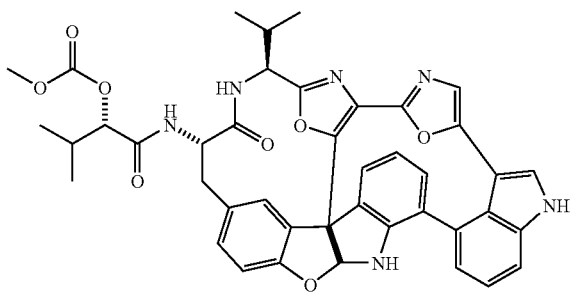

The compound synthesized in Example 16 (50 mg, 0.072 mmol) was dissolved in THF (3 mL) and pyridine (57 mg, 0.058 mL, 0.72 mmol) was added at RT under $N_2$. The solution was cooled to 0° C. in an ice-water bath followed by the addition of methyl chloroformate (68 mg, 0.055 mL, 0.72 mmol). After stirring at RT overnight, the reaction mixture was dissolved in EtOAc, washed with water and brine, and dried over $Na_2SO_4$. The solution was concentrated and the crude product was purified by flash chromatography to afford the desired product. MS: m/z=755.1 (M+1).

Example 33

Step A

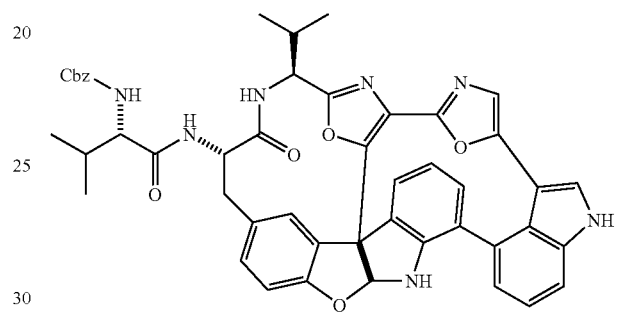

The conditions for this reaction are similar to those used for Example 16. The N-hydroxysuccinimide ester of L-Cbz-valine and the material synthesized in Example 15 served as the starting materials. MS: m/z=830.1 (M+1).

Step B

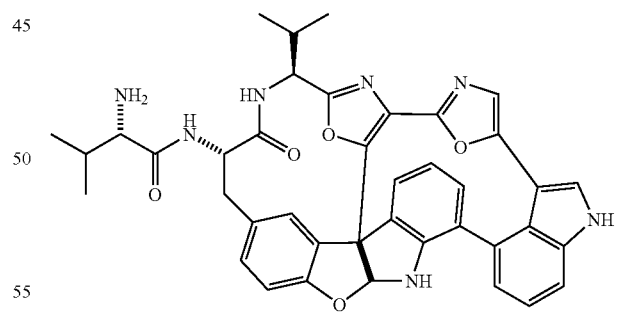

To a 15-mL flask containing material synthesized in Step A above (33 mg, 0.040 mmol) were added methanol (1 mL) and 10% Pd/C (4.2 mg) under $N_2$. A $H_2$ balloon was attached and the flask was purged four times with $H_2$. Then the $H_2$ balloon was opened to the reaction system. After 5 h stirring almost no starting material remained. The reaction was stopped. The reaction mixture was filtered through a pad of Celite® and the black cake was washed with methanol (3×1 mL). The filtrate was concentrated and the crude product was purified by PTLC eluting with MeOH/CH$_2$Cl$_2$ (15/85) to afford desired product as an off-white solid (13 mg, 47%). MS: m/z=696.2 (M+1).

Example 34

Step A

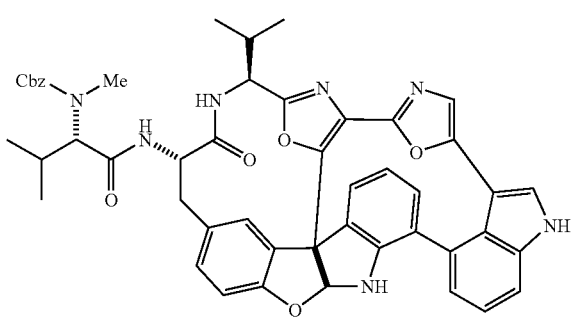

The conditions for this reaction are similar to those used for Step B of Example 30. L-Cbz-N-methylvaline and the material synthesized in Example 15 served as the starting materials. MS: m/z=844.2 (M+1).

Step B

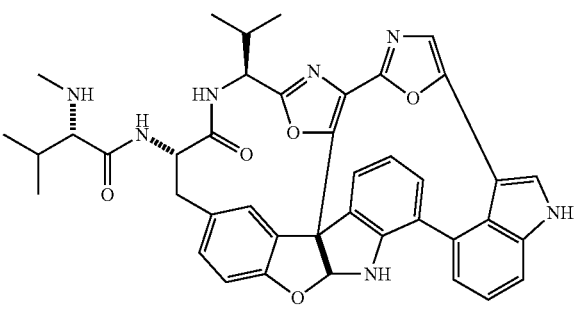

The conditions for this reaction are similar to those used for Step B of Example 33. The material synthesized in Step A above served as the starting material. MS: m/z=710.3 (M+1).

Example 35

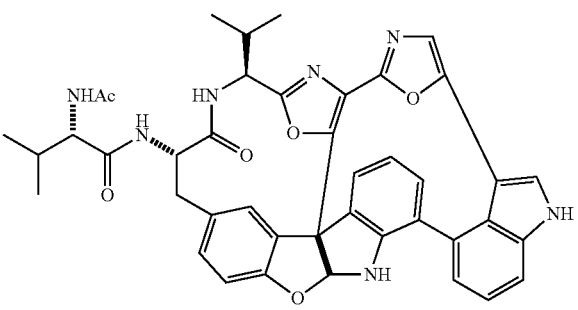

The conditions for this reaction are similar to those used for Example 31. The material synthesized in Step B of Example 33 served as the starting material. MS: m/z=738.2 (M+1).

Example 36

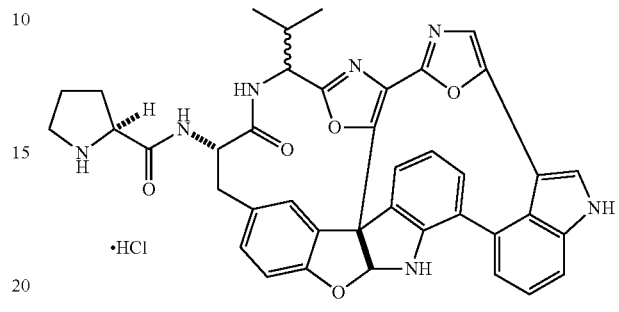

The product of Example 36 was prepared by reaction of the amine from Example 15, using coupling conditions similar to those described for Example 17. Boc-L-proline was used in place of (S)-mandelic acid. After isolation of the coupling product, the Boc protecting group was removed by treatment with 4 M HCl in 1,4-dioxane. MS: m/z=694.2 (M+1).

Example 37

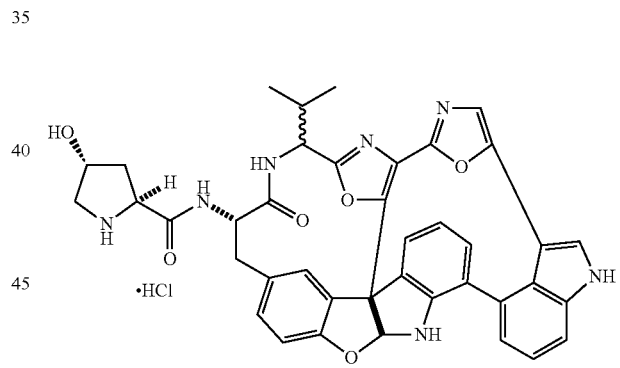

The product of Example 37 was prepared by reaction of the amine from Example 15, using coupling conditions similar to those described for Example 17. trans-Boc-4-hydroxy-L-proline was used in place of (S)-mandelic acid. After isolation of the coupling product, the Boc protecting group was removed by treatment with 4 M HCl in 1,4-dioxane. EDC/acid, then HCl/dioxane. MS: m/z=710.1 (M+1).

Examples 38-57

The compounds in Examples 38-57 were prepared using coupling conditions similar to those used in Example 17, with the amine synthesized in Example 15 serving as the starting material. Coupling of this amine with a series of carboxylic acids produced the amide derivatives shown in Table 2.

TABLE 2

| | | LCMS m/z |
|---|---|---|
| Example 38 | | 681.2 (M + 1) |
| Example 39 | | 681.2 (M + 1) |
| Example 40 | | 695.1 (M + 1) |
| Example 41 | | 708.8 (M + 1) |

TABLE 2-continued

| | LCMS m/z |
|---|---|
| Example 42 | 679.0 (M + 1) |
| Example 43 | 678.7 (M + 1) |
| Example 44 | 692.8 (M + 1) |
| Example 45 | 747.2 (M + 1) |

TABLE 2-continued
| | | LCMS m/z |
|---|---|---|
| Example 46 | 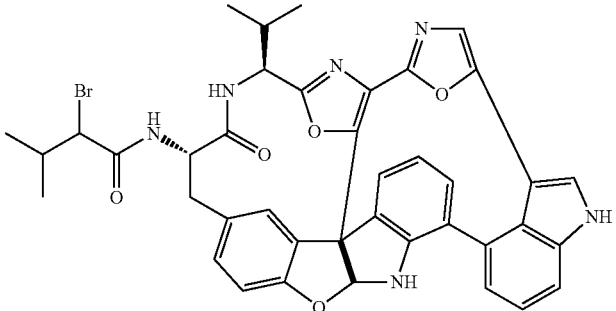 | 759.0 (M + 1) |
| Example 47 | 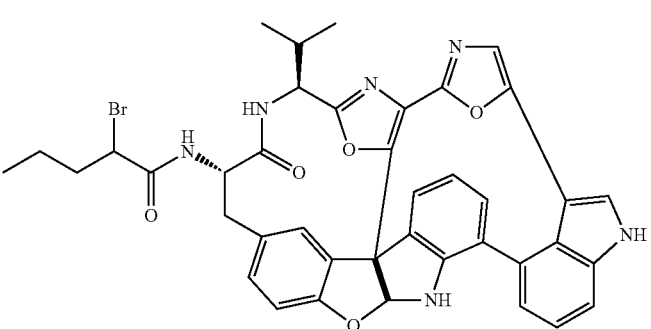 | 758.7 (M + 1) |
| Example 48 | 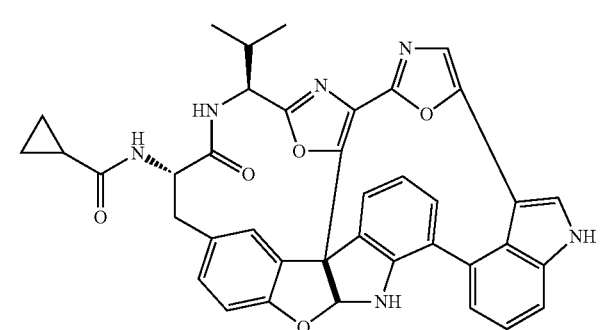 | 665.1 (M + 1) |
| Example 49 | 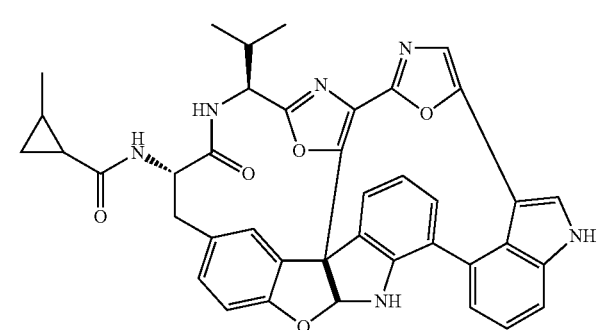 | 679.0 (M + 1) |

TABLE 2-continued

| | | LCMS m/z |
|---|---|---|
| Example 50 | [structure] | 692.8 (M + !) |
| Example 51 | [structure] | 706.8 (M + !) |
| Example 52 | [structure] | 720.8 (M + 1) |
| Example 53 | [structure] | 695.1 (M + 1) |

TABLE 2-continued
| | | LCMS m/z |
|---|---|---|
| Example 54 | 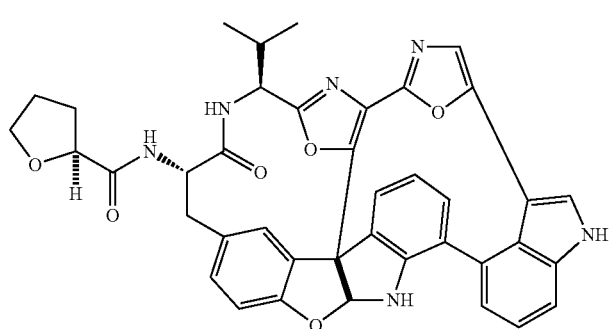 | 695.1 M + 1) |
| Example 55 | 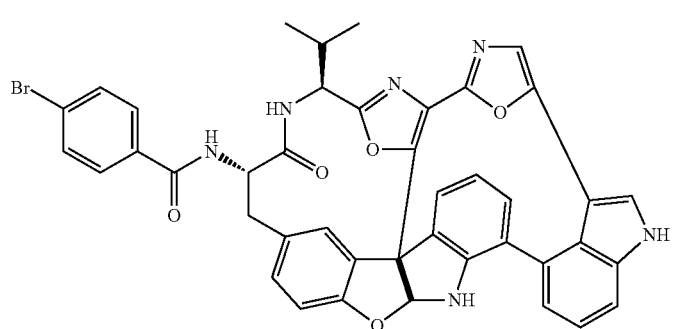 | 779.0 (M + !) |
| Example 56 | 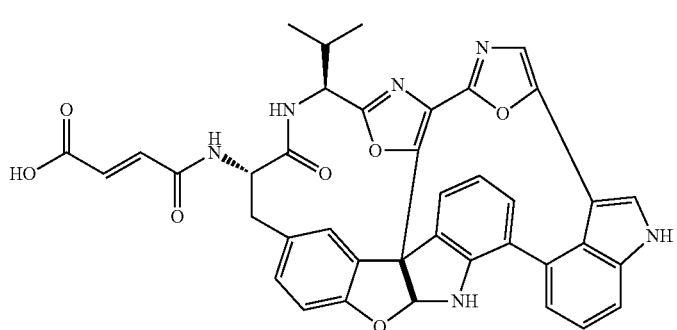 | 694.8 (M + 1) |
| Example 57 | 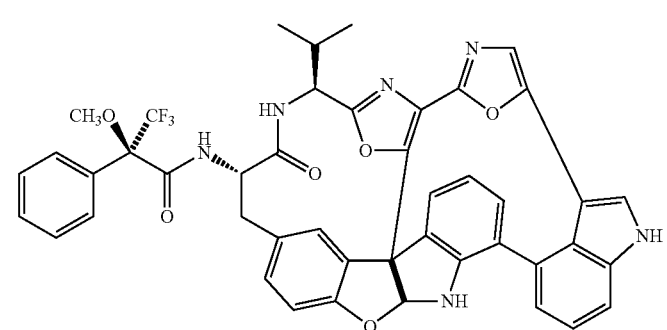 | 813.2 (M + 1) |

TABLE 2-continued

| | | LCMS m/z |
|---|---|---|
| Example 58 | | 813.2 (M + 1) |

Example 59

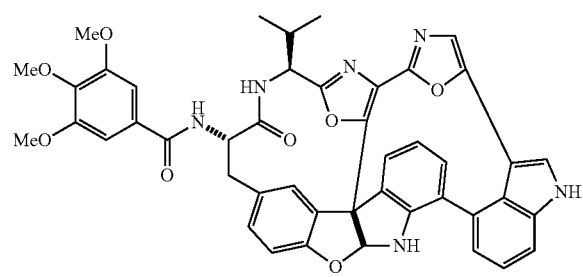

The compound synthesized in Example 15 (25 mg, 0.042 mmol) was dissolved in THF (1.0 mL) in a small reaction vial. A few 3 Å molecular sieve pellets were added along with 4-methylmorpholine (0.007 mL, 6 mg, 0.06 mmol), followed by 3,4,5-trimethoxybenzoyl chloride (10 mg, 0.043 mmol). After 3 h, the reaction mixture was diluted into EtOAc (30 mL) and washed with 1 N aqueous HCl (15 mL), saturated aqueous NaHCO$_3$ (15 mL) and saturated aqueous NaCl (10 mL). The organic layer was dried over Na$_2$SO$_4$, decanted, and evaporated. The residue was purified by flash column chromatography on silica gel packed in 1:1 EtOAc/CH$_2$Cl$_2$, eluting with 3% MeOH in 1:1 EtOAc/CH$_2$Cl$_2$, to give 25 mg of the amide product as a white solid. MS: m/z=791.1 (M+1).

Examples 60-65

The compounds in Examples 60-65 shown in Table 3 were prepared using coupling conditions similar to those used in Example 59, with the amine synthesized in Example 15 serving as the starting material. Coupling of this amine with a series of carboxylic acid chlorides produced the amide derivatives. N,N-Diisopropylethylamine was substituted for 4-methylmorpholine as the base.

TABLE 3

| | | LCMS m/z |
|---|---|---|
| Example 60 | | 680.8 (M + 1) |
| Example 61 | | 694.8 (M + 1) |

TABLE 3-continued

| | | LCMS m/z |
|---|---|---|
| Example 62 | | 694.8 (M + 1) |
| Example 63 | | 706.7 (M + 1) |
| Example 64 | | 720.8 (M + 1) |
| Example 65 | | 796.7 (M + 1) |

Example 66

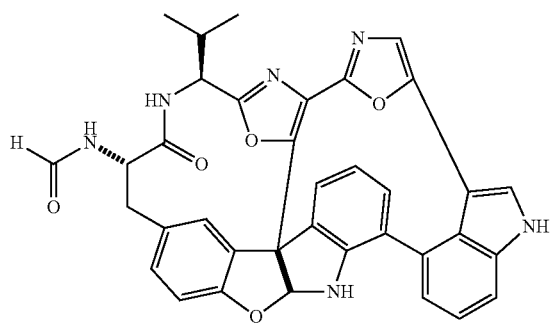

The conditions for this reaction are similar to those used for Step B of Example 30. Formic acid and the material synthesized in Example 15 served as the starting materials. MS: m/z=624.8 (M+1).

Example 67

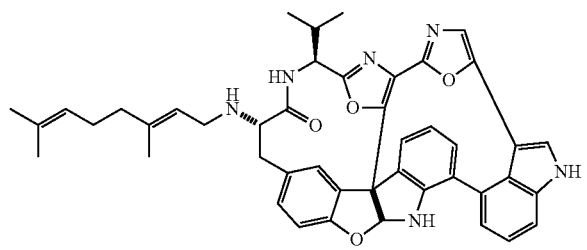

The compound synthesized in Example 15 (17 mg, 0.028 mmol) was dissolved in THF (3 mL). Geranyl bromide (0.006 mL, 0.028 mmol) and N,N-diisopropylethylamine (0.01 mL, 0.056 mmol) were added at 0° C. under N$_2$. After stirring overnight at RT, the solvent was removed at reduced pressure and the residue was purified by flash chromatography to afford the desired product. MS: m/z=733.2 (M+1).

Example 68

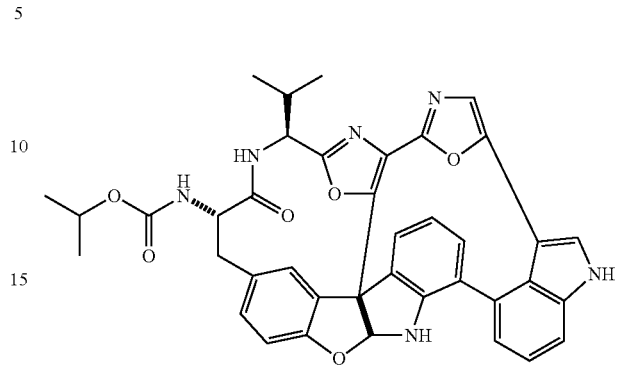

The compound synthesized in Example 15 (20 mg, 0.034 mmol) was dissolved in THF (1.0 mL) in a small reaction vial. A few 3 A molecular sieve pellets were added along with 4-methylmorpholine (0.007 mL, 6 mg, 0.06 mmol), followed by 1 M isopropyl chloroformate in toluene (0.037 mL, 0.037 mmol). After 4 h, the reaction mixture was diluted into EtOAc (30 mL) and washed with 1 N aqueous HCl (15 mL), saturated aqueous NaHCO$_3$ (15 mL) and saturated aqueous NaCl (10 mL). The organic layer was dried over Na$_2$SO$_4$, decanted, and evaporated. The residue was purified by flash column chromatography on silica gel packed in 1:1 EtOAc/CH$_2$Cl$_2$, eluting with 2% MeOH in 1:1 EtOAc/CH$_2$Cl$_2$, to give 19 mg of the carbamate product. MS: m/z=683.1 (M+1).

Examples 69-72

The compounds in Examples 69-72 shown in Table 4 were prepared using coupling conditions similar to those used in Example 68, with the amine synthesized in Example 15 serving as the starting material. Coupling of this amine with a series of alkyl chloroformates produced the carbamate derivatives. N,N-Diisopropylethylamine was substituted for 4-methylmorpholine as the base. For Example 72, S-propyl-chlorothioformate was used in the reaction.

TABLE 4

|  | LCMS m/z |
| --- | --- |
| Example 69 | 696.7 (M + 1) |

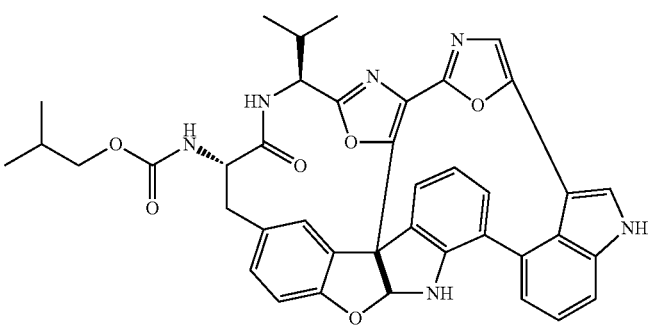

TABLE 4-continued

| | | LCMS m/z |
|---|---|---|
| Example 70 | (structure) | 678.7 (M + 1) |
| Example 71 | (structure) | 680.7 (M + 1) |
| Example 72 | (structure) | 698.7 (M + 1) |

Example 73

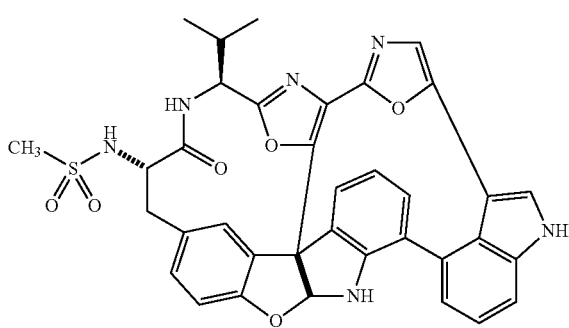

The compound synthesized in Example 15 (25 mg, 0.042 mmol) was dissolved in THF (1.0 mL) in a small reaction vial. A few 3 Å molecular sieve pellets were added along with 4-methylmorpholine (0.007 mL, 6 mg, 0.06 mmol), followed by methanesulfonyl chloride (0.0035 mL, 5.2 mg, 0.045 mmol). After 3 h, the reaction mixture was diluted into EtOAc (30 mL) and washed with 1 N aqueous HCl (15 mL), saturated aqueous NaHCO$_3$ (15 mL) and saturated aqueous NaCl (10 mL). The organic layer was dried over Na$_2$SO$_4$, decanted, and evaporated. The residue was purified by flash column chromatography on silica gel packed in 1:1 EtOAc/CH$_2$Cl$_2$, eluting with 3% MeOH in 1:1 EtOAc/CH$_2$Cl$_2$, to give 18 mg of the sulfonamide product as a white solid. MS: m/z=675.0 (M+1).

Examples 74-75

The compounds in Examples 58-63 shown in Table 5 were prepared using coupling conditions similar to those used in Example 73, with the amine synthesized in Example 15 serving as the starting material. Coupling of this amine with a series of sulfonyl chlorides produced the sulfonamide derivatives. In the case of Example 75, N,N-diisopropylethylamine was substituted for 4-methylmorpholine as the base.

TABLE 5

| | LCMS m/z |
|---|---|
| Example 74 | 737.0 (M + 1) |

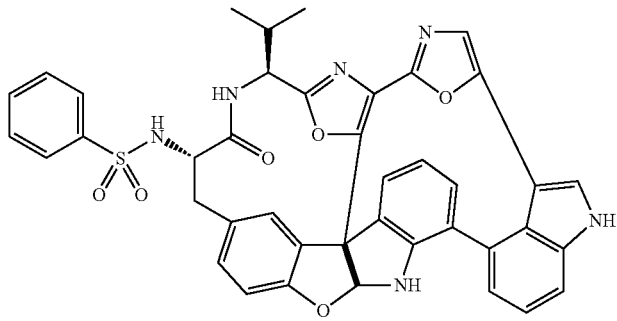

| Example 75 | 742.7 (M + 1) |

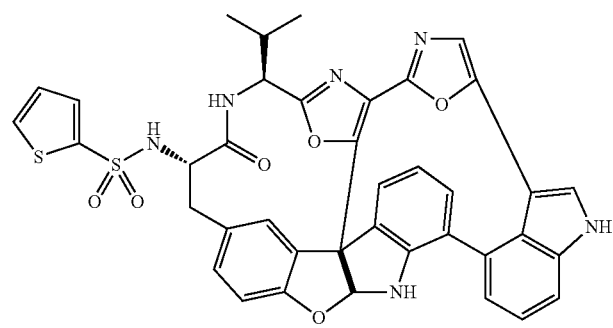

Example 76

Step A

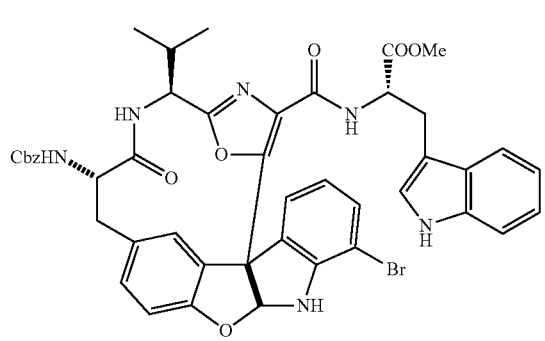

The conditions for this reaction are similar to those used for Example 10. L-Tryptophan methyl ester hydrochloride and the material synthesized in Example 9 served as the starting materials. MS: m/z=873.2 (M+1).

Step B

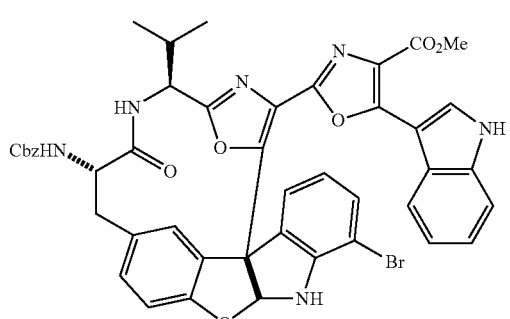

A solution of DDQ (411 mg, 1.81 mmol) in THF (5 mL) was added to the compound synthesized in Step A above (720 mg, 0.824 mmol) in THF (15 mL) and the dark solution was heated to gentle reflux in an oil bath at 85° C. for 1.5 h. After cooling, the solvent was removed on a rotary evaporator. The residue was diluted with EtOAc (200 mL), washed with saturated NaHCO$_3$ (50 mL), water (2×50 mL) and brine (50 mL), and dried over Na$_2$SO$_4$. After concentration the crude product was purified by silica gel chromatography eluting with EtOAc/hexanes (40/60 to 45/55) to afford desired product as a brownish yellow solid (427 mg, 60%). MS: m/z=869.1 (M+1).

Step C

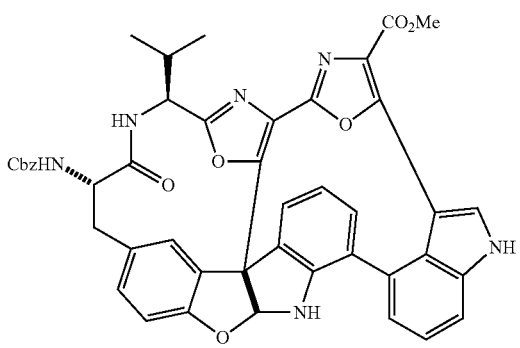

To a dry flask containing the material synthesized in Step B above (44 mg, 0.051 mmol) was added anhydrous acetonitrile (12 mL). The solution was transferred to two quartz tubes and argon was bubbled through the solutions for 30 min. The solutions were cooled to −30° C. and a solution of sodium bis(trimethylsilyl)amide in THF (1.0 M, 0.061 mL, 0.061 mmol) was added dropwise over 5 min. The resulting cold solution was irradiated by UV for 30 min and quenched by addition of aqueous saturated $NH_4Cl$ (2 mL). The mixture was extracted by EtOAc (2×50 mL) and the combined organic layers were washed with saturated aqueous $NH_4Cl$ (10 mL), water (2×10 mL) and brine (10 mL), and dried over $Na_2SO_4$. After concentration the crude product was purified by PTLC eluting with $MeOH/CH_2Cl_2$ (8/92) to afford desired product as an off-white solid (3.5 mg, 9%). MS: m/z=789.0 (M+1).

Step D

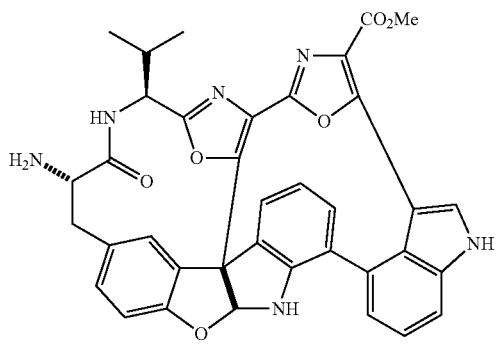

To a 15-mL flask containing the material synthesized in Step C above (3.5 mg, 0.00443 mmol) was added methanol (1 mL) and 20% $Pd(OH)_2$/C (5.0 mg) under $N_2$. A $H_2$ balloon was attached and the flask was purged four times with $H_2$. Then the $H_2$ balloon was opened to the reaction system. After 4 h stirring almost no starting material remained. The reaction was stopped. The reaction mixture was filtered through a pad of Celite® and the black cake was washed with methanol (3×1 mL). The filtrate was concentrated and the crude product was used in next step.

Step E

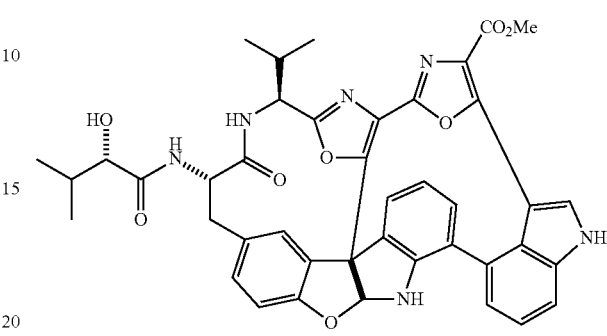

The conditions for this reaction are similar to those used for Example 16. The N-hydroxysuccinimide ester of (S)-2-hydroxy-3-methylbutyric acid and the material synthesized in Step D above served as the starting materials. MS: m/z=755.2 (M+1).

Example 77

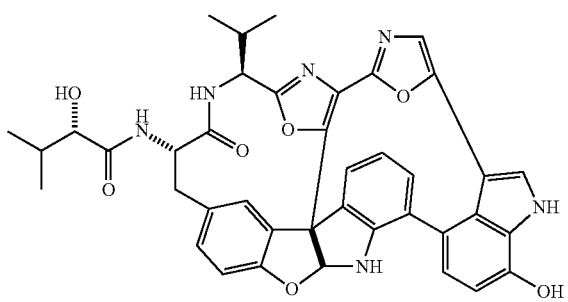

The conditions for this reaction are similar to those used for Step B of Example 80. The material synthesized in Step A Example 80 and (S)-2-hydroxy-3-methylbutyric acid served as the starting materials. MS: m/z=713.3 (M+1).

Example 78

Step A

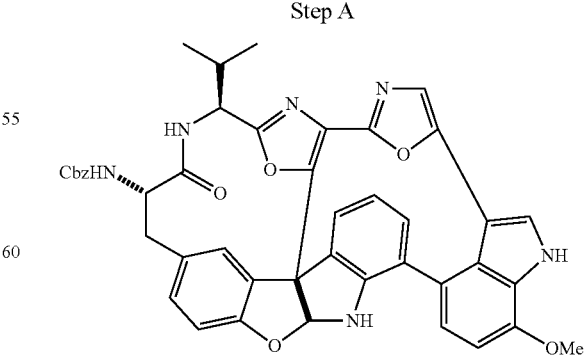

To a dry flask containing the material synthesized in Example 13 (55 mg, 0.074 mmol) was added $Cs_2CO_3$ (36 mg, 0.11 mmol), anhydrous DMF (1 mL) and iodomethane (0.023 mL, 0.37 mmol). The resulting reaction mixture was stirred at RT overnight. The mixture was diluted with EtOAc (30 mL), washed with water (3×10 mL) and brine (2×10 mL), and dried over Na$_2$SO$_4$. After concentration the crude product was purified by PTLC eluting with MeOH/CH$_2$Cl$_2$ (5/95) to afford desired product as an off-white solid (20 mg, 36%). MS: m/z=761.2 (M+1).

Step B

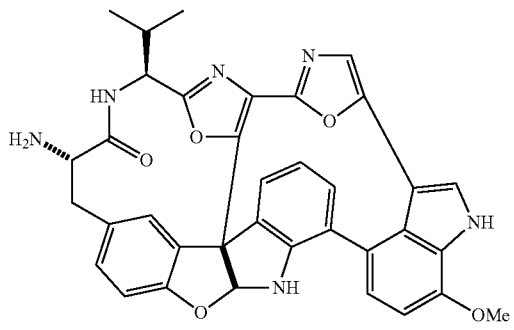

The conditions for this reaction are similar to those used for Step D of Example 76. The material synthesized in Step A above served as the starting material. The crude product was used in next step.

Step C

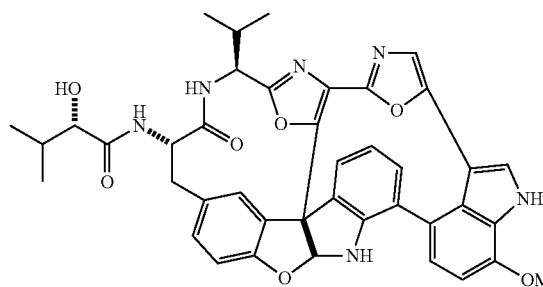

The conditions for this reaction are similar to those used for Example 16. The N-hydroxysuccinimide ester of (S)-2-hydroxy-3-methylbutyric acid and the material synthesized in Step B above served as the starting materials. MS: m/z=727.2 (M+1).

Example 79

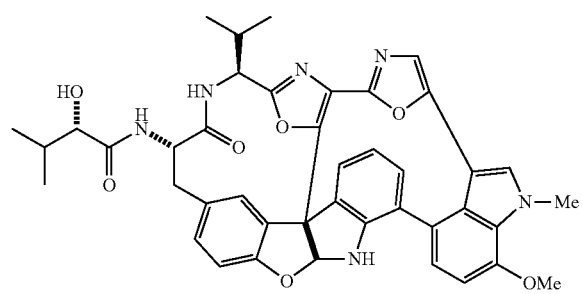

The product of Example 79 was isolated as a second product from the reaction described in Example 78. MS: m/z=741.3 (M+1).

Example 80

Step A

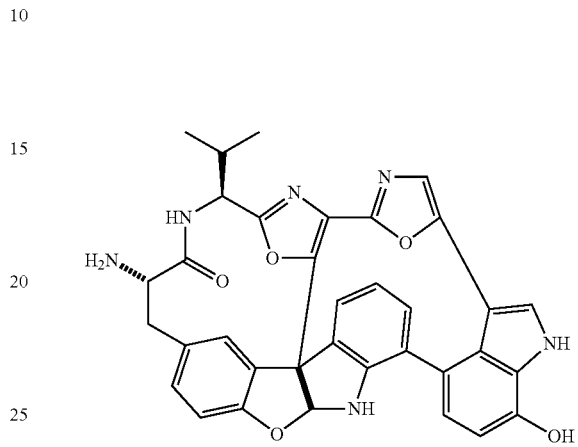

To a 50-mL flask containing the product from Example 13 (153 mg, 0.21 mmol) and 10% Pd/C (30 mg) was added methanol (5 mL) and triethylamine (0.086 mL, 0.62 mmol) under N$_2$. The flask was purged with H$_2$ using a H$_2$ balloon and the mixture was stirred under H$_2$ at RT. After 3 h the reaction mixture was filtered through a 0.45 micron filter. The filtrate was concentrated and the residue was used directly in next step without further purification. The structure of the product was confirmed by LCMS.

Step B

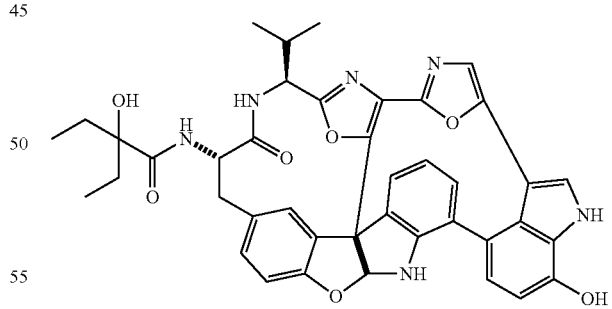

To a solution of the product from Step A above (84 mg, 0.14 mmol), 2-ethyl-2-hydroxybutyric acid (21.8 mg, 0.165 mmol) and HOBt (22.2 mg, 0.165 mmol) in DMF (3 mL) was added N,N-diisopropylethylamine (0.036 mL, 0.206 mmol), followed by EDC (31.5 mg, 0.165 mmol) at RT. After stirring for 12 h, the reaction solution was diluted with EtOAc (100 mL), and washed with 1 N HCl (20 mL), water (20 mL), saturated NaHCO$_3$ (20 mL) and brine (20 mL). After drying over Na$_2$SO$_4$, the solution was concentrated and the crude was purified by flash chromatography eluting with MeOH/CH$_2$Cl$_2$ gradient (5/95) to afford the desired product. MS: m/z=727.0 (M+1).

Example 81

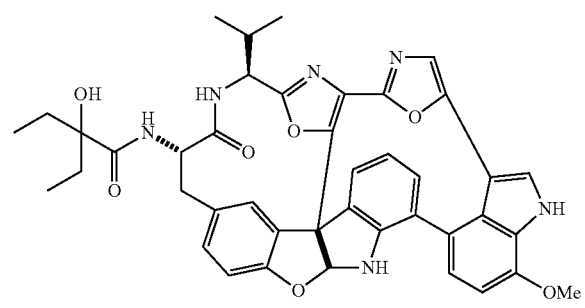

The conditions for this reaction are similar to those used for Step B of Example 80. The material synthesized in Step B of Example 78 and 2-ethyl-2-hydroxybutyric acid served as the starting materials. MS: m/z=741.2 (M+1).

Example 82

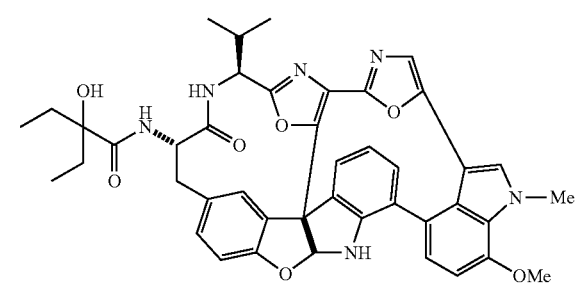

The product of Example 82 was isolated as a second product from the reaction described in Example 81. MS: m/z=755.1 (M+1).

Example 83

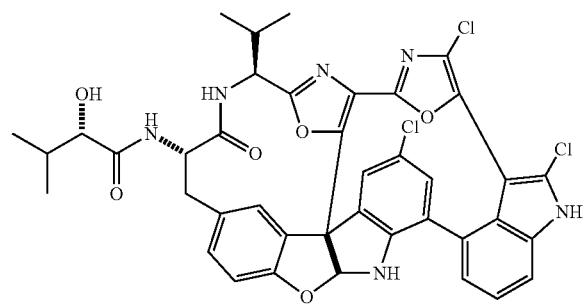

To a dry flask containing the material synthesized in Example 16 (7.0 mg, 0.01 mmol) was added the solution of NCS (7.3 mg, 0.055 mmol) in anhydrous THF (0.8 ml). The reaction solution was stirred at RT for 18 h under N$_2$. The reaction was monitored by LCMS. The reaction mixture was diluted with EtOAc (50 ml), followed by washing with water (2×20 ml) and brine (10 ml). The solution was dried over Na$_2$SO$_4$ and concentrated. The crude product was purified by PTLC eluting with MeOH/CH$_2$Cl$_2$ (8/92) to afford desired product as an off-white solid (7 mg, 88%). MS: m/z=799.0 (M+1).

Example 84

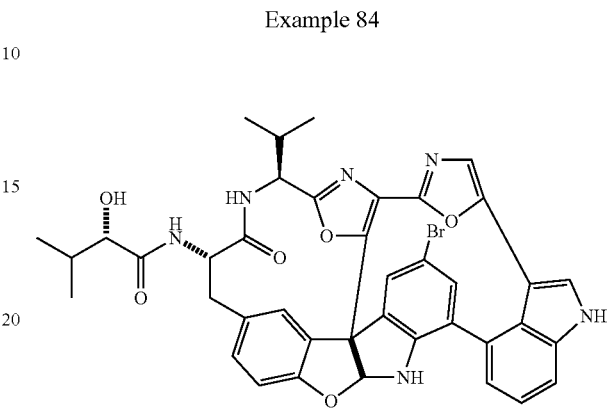

To a dry flask were added the material synthesized in Example 16 (33 mg, 0.047 mmol) and anhydrous THF (1 mL). All of the solid dissolved. A stock solution of NBS (12.6 mg, 0.071 mmol) in anhydrous THF (1 mL) was added dropwise at RT. After the addition, the reaction solution was stirred at RT for 18 h. The reaction was monitored by LCMS. All of the starting material was consumed. The reaction mixture was diluted with EtOAc (30 mL), washed with water (2×10 mL) and brine (10 mL), and dried over Na$_2$SO$_4$. The crude product was purified by PTLC (elute: EtOAc) to afford the desired product (8.1 mg, 22%). The structure was confirmed by LCMS [m/z=774.6 (M+1)] and $^1$H NMR (CD$_3$OD, 400 MHz).

Example 85

Step A

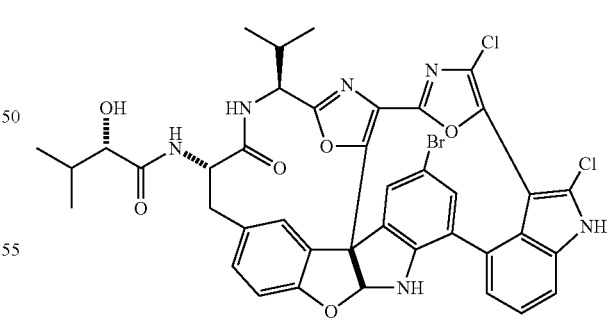

To a dry flask containing the product from Example 84 (5 mg, 0.00645 mmol) was added anhydrous THF (0.5 mL). A stock solution of NCS (2.2 mg, 0.016 mmol) in THF (1 mL) was added dropwise at RT. The reaction solution was stirred at RT for 3 h. The reaction was monitored by LCMS. No starting material remained. The reaction mixture was diluted with EtOAc (30 mL), washed with water (2×10 mL) and brine (10 mL), and dried over Na$_2$SO$_4$. The crude was purified by PTLC (elute: EtOAc) to afford the desired product (2.3 mg, 42%). MS: m/z=842.5 (M+1).

Step B

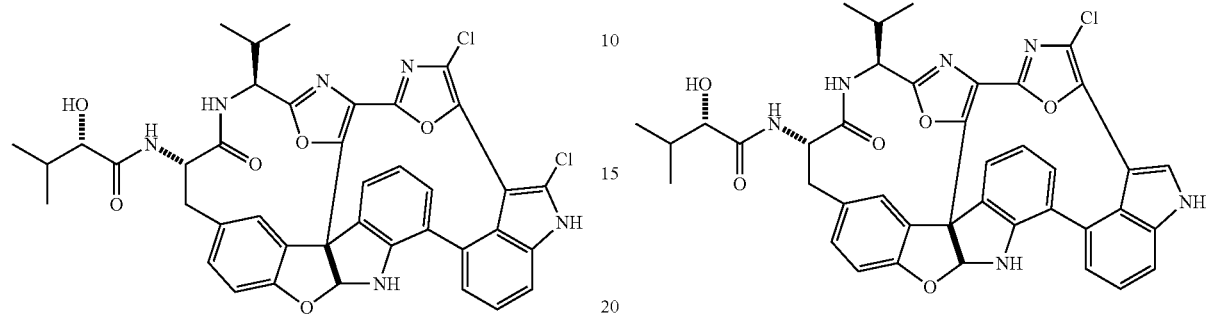

Diazonamide A (reference example)

To a flask containing the product from Step A above (2.3 mg, 0.0027 mmol) was added methanol (1.5 mL). Under N$_2$ atmosphere 10% Pd/C (1.4 mg) was added. A H$_2$ balloon was attached immediately and the flask was purged with H$_2$ four times. The reaction proceeded for 2 h. The mixture was filtered through a pad of Celite® and the residue was washed with MeOH (2×2 mL). The filtrate was concentrated and purified by PTLC (elute: EtOAc) to afford the desired product (2.0 mg, 96%). The structure was confirmed by LCMS [m/z=764.7 (M+1)] and $^1$H NMR (CD$_3$OD, 400 MHz).

Example 86

Step A

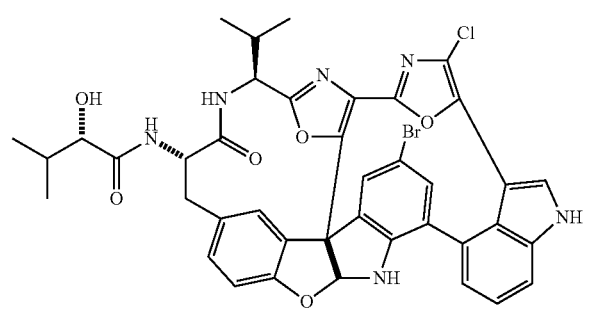

To a dry flask containing the material synthesized in Example 84 (5 mg, 0.0065 mmol) was added anhydrous THF (0.5 mL). A stock solution of NCS (2.2 mg, 0.0161 mmol) in THF (1 mL) was added dropwise at RT. The reaction solution was stirred at RT for 3 h. The reaction was monitored by LCMS. No starting material remained. The reaction mixture was diluted with EtOAc (30 mL), washed with water (2×10 mL) and brine (10 mL), and dried over Na$_2$SO$_4$. The crude product was purified by PTLC (elute: EtOAc) to afford the desired product (1.5 mg, 29%). MS: m/z=808.5 (M+1).

Step B

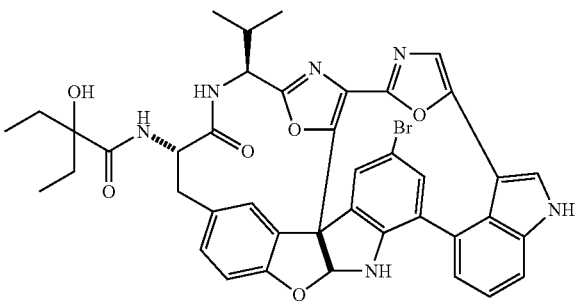

The conditions for this reaction are similar to those used in Step B of example 85. MS: m/z=730.7 (M+1).

Example 87

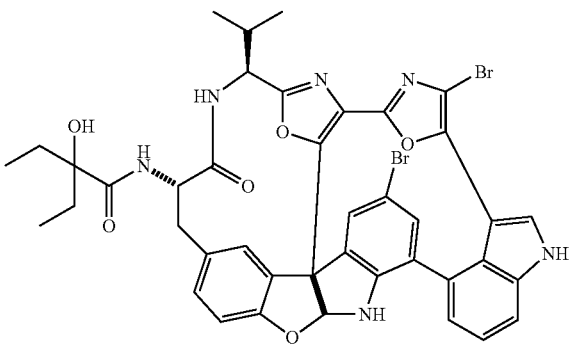

The product of Example 87 was prepared using reaction conditions similar to those described in Example 84. The material synthesized in Example 24 served as the starting material. MS: m/z=788.5 (M+1).

Example 88

The product of Example 88 was prepared using conditions similar to those described in Example 89. The material synthesized in Example 24 served as the starting material. MS: m/z=868.5 (M+1).

Example 89

Step A

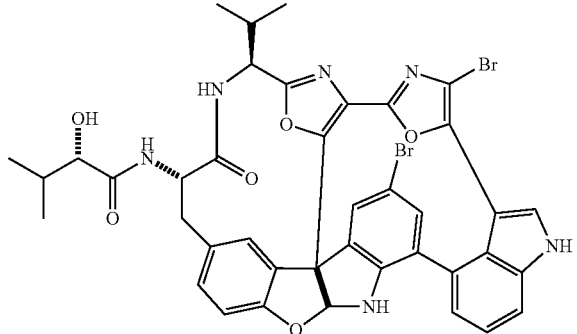

To a dry flask were added the material synthesized in Example 16 (33 mg, 0.047 mmol) and anhydrous THF (1 mL). All of the solid dissolved. A stock solution of NBS (12.6 mg, 0.071 mmol) in anhydrous THF (1 mL) was added dropwise at RT. The reaction solution was stirred at RT for an additional 18 hrs. The reaction was monitored by LCMS. All starting material was consumed. The reaction mixture was diluted with EtOAc (30 mL), washed with water (2×10 mL) and brine (10 mL), and dried over Na$_2$SO$_4$. The crude product was purified by PTLC (elute: EtOAc) to afford the desired product (11.5 mg, 28%). MS: m/z=852.5 (M+1).

Step B

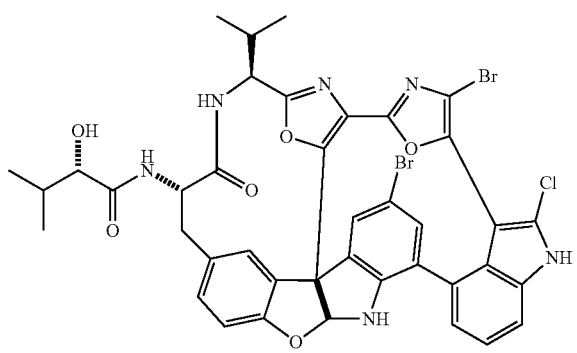

To a dry flask containing the material synthesized in example 70 (5.5 mg, 0.0064 mmol) was added anhydrous THF (0.5 mL). A stock solution of NCS (3.4 mg, 0.026 mmol) in THF (1 mL) was added dropwise at RT. The reaction solution was stirred at RT for 3 h. The reaction was monitored by LCMS. No starting material remained. The reaction mixture was diluted with EtOAc (30 mL), washed with water (2×10 mL) and brine (10 mL), and dried over Na$_2$SO$_4$. The crude product was purified by PTLC eluting with MeOH/CH$_2$Cl$_2$ (7/93) to afford the desired product (3.5 mg, 62%). MS: m/z=886.5 (M+1).

Step C

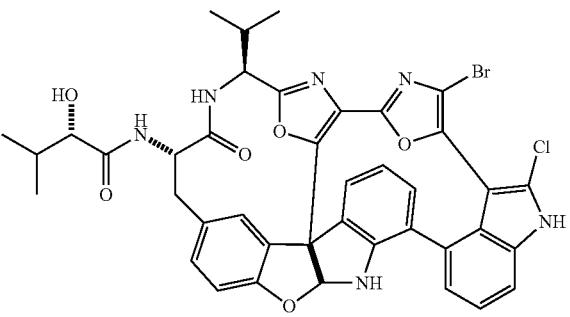

The conditions for this reaction are similar to those used in Step B of example 85. MS: m/z=808.5 (M+1).

Example 90

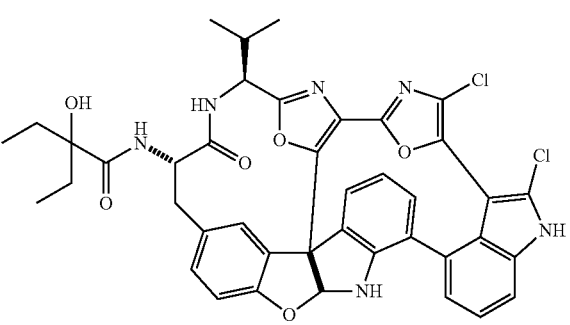

The product of Example 90 was prepared using reaction conditions similar to those described for Example 85. The material synthesized in Example 87 served as the starting material. MS: m/z=778.7 (M+1).

Example 91

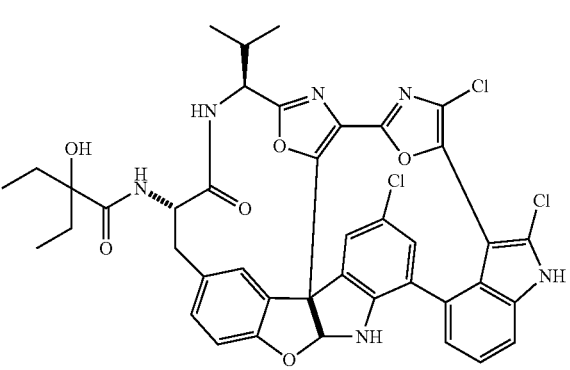

The product of Example 91 was isolated as a minor product from the reaction described in Example 90. MS: m/z=812.5 (M+1).

Example 92

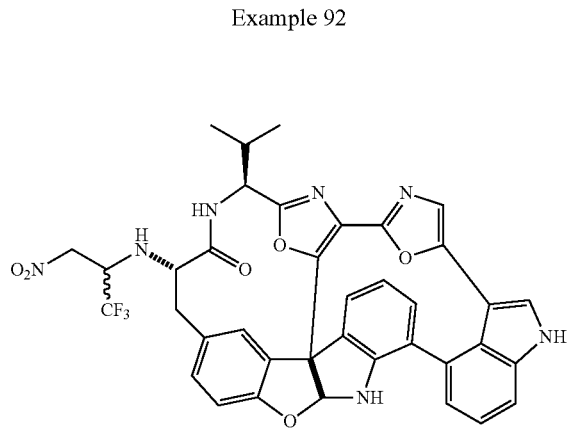

Chemical Formula: $C_{38}H_{30}F_3N_7O_6$
Exact Mass: 737.22; Molecular Weight: 737.68
Isolated as a 2:1 mixture of diastereomers.

Example 93

Additional Compounds

The compounds shown in Table 6 are also available by the methods of the invention as described herein.

TABLE 6

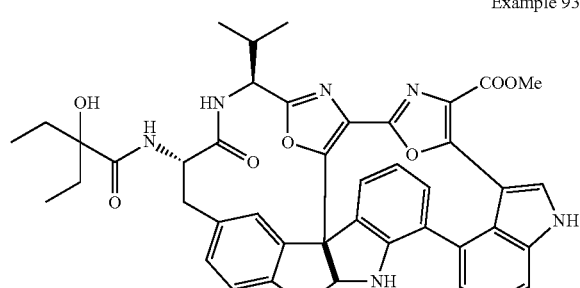

Example 93a

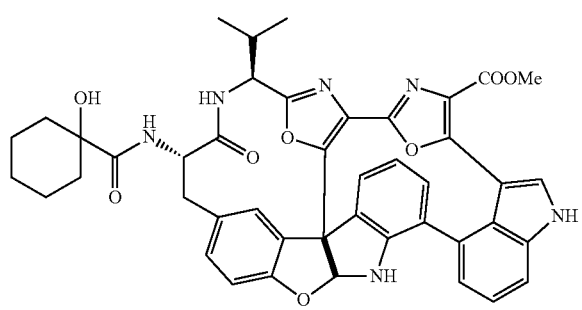

Example 93b

TABLE 6-continued

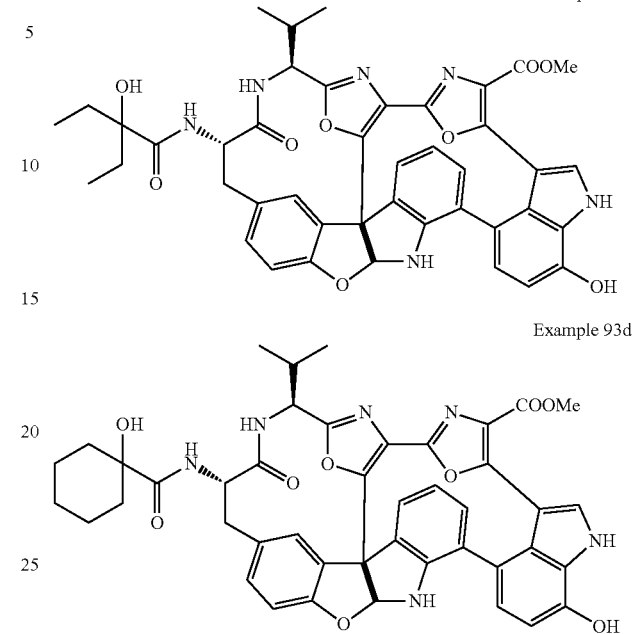

Example 93c

Example 93d

Example 93e

Example 93f

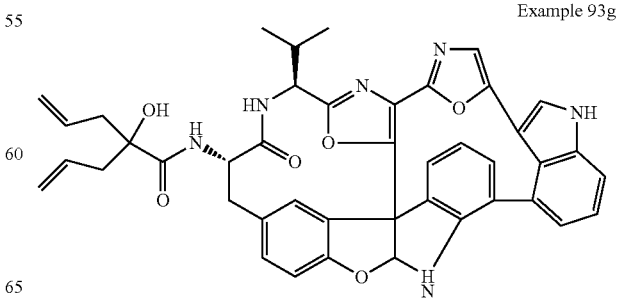

Example 93g

TABLE 6-continued

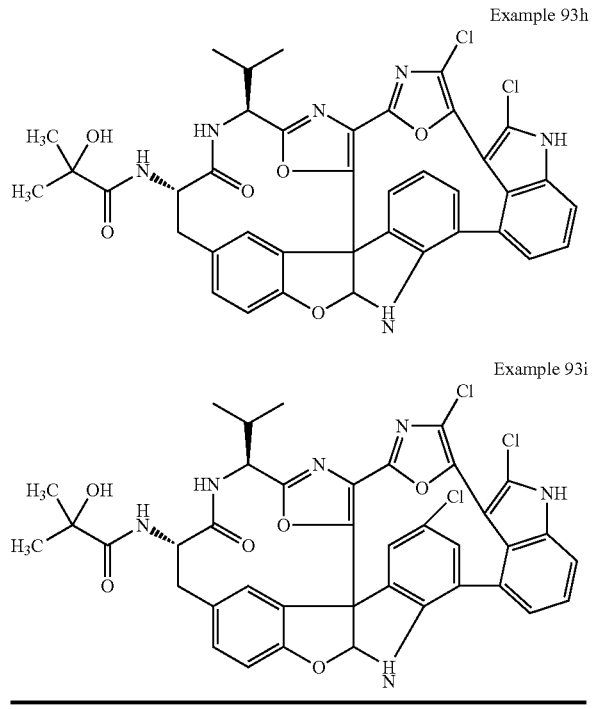

Example 93h

Example 93i

Example 94

Cell Viability Assay Protocol

Cell viability assays were run using standard protocols known to those of skill in art. Cells were plated in 96 well plates at the density of 3,000-10,000 cells per well. Twenty four hours later, cells were treated with increasing concentration of test compounds (1 nM to 1 µM). After another 48 hour, cell survival was measured using CELL-TITER-GLO® reagent (Promega) following the protocol provided by the manufacture. The $IC_{50}$ value was determined as the concentration of test compound that kills 50% of the cell population.

Example 95

Representative Biological Data

Cell viability data generated according to the protocol described herein was generated for representative compounds in the A2058 (human melanoma) and U937 (human leukemic monocyte lymphoma) cell lines. Data are provided below in Table 7. The compound of Example 16 ("Compound J") was used as a reference compound.

TABLE 7

Representative Cell Viability Data

| Example # | $IC_{50}$ (µM) A2058 | $IC_{50}$ (µM) U937 |
|---|---|---|
| 16 (Cpd J) | 0.043 | 0.034 |
| 17 | 0.630 | 0.465 |
| 18 | 0.394 | 0.208 |
| 19 | 0.222 | 0.062 |
| 20 | 0.158 | 0.142 |
| 21 | >1 | >1 |
| 22 | 0.230 | 0.146 |
| 23 | 0.124 | 0.156 |
| 24 | 0.105 | 0.062 |
| 25 | 0.769 | 0.420 |
| 26 | 0.214 | 0.154 |
| 27 | 0.181 | 0.128 |
| 28 | 0.208 | 0.133 |
| 29 | >1 | >1 |
| 30 | 0.197 | 0.224 |
| 31 | 0.194 | 0.062 |
| 32 | 0.211 | 0.157 |
| 33 | 1.444 | 0.572 |
| 34 | 0.221 | 0.393 |
| 35 | 0.232 | 0.183 |
| 36 | >1 | >1 |
| 37 | >1 | >1 |
| 38 | 0.417 | 0.216 |
| 39 | 0.707 | 0.555 |
| 40 | 0.233 | 0.164 |
| 41 | 0.397 | 0.220 |
| 42 | 0.409 | 0.221 |
| 43 | 0.356 | 0.186 |
| 44 | 0.587 | 0.399 |
| 45 | 0.887 | 0.780 |
| 46 | 0.313 | 0.443 |
| 47 | 0.546 | 0.323 |
| 48 | 0.457 | 0.220 |
| 49 | 0.443 | 0.245 |
| 50 | 0.339 | 0.331 |
| 51 | 0.235 | 0.276 |
| 52 | 0.386 | 0.491 |
| 53 | 0.209 | 0.078 |
| 54 | 0.081 | 0.078 |
| 55 | 0.613 | 0.406 |
| 56 | >1 | 0.756 |
| 57 | 0.580 | 0.618 |
| 58 | >1 | 0.821 |
| 59 | 0.798 | 0.619 |
| 60 | 0.538 | 0.255 |
| 61 | 0.636 | 0.550 |
| 62 | 0.556 | 0.247 |
| 63 | 0.488 | 0.206 |
| 64 | >1 | >1 |
| 65 | 0.796 | 0.509 |
| 66 | 0.766 | 0.499 |
| 67 | >1 | >1 |
| 68 | 0.451 | 0.214 |
| 69 | 0.541 | 0.272 |
| 70 | 0.692 | 0.434 |
| 71 | 0.451 | 0.185 |
| 72 | 0.600 | 0.543 |
| 73 | 0.140 | 0.067 |
| 74 | 0.429 | >1 |
| 75 | >1 | >1 |
| 76 | 0.013 | 0.018 |
| 77 | 0.070 | 0.052 |
| 78 | 0.042 | 0.051 |
| 79 | 0.022 | 0.027 |
| 80 | 0.183 | 0.182 |
| 81 | 0.123 | 0.054 |
| 82 | 0.029 | 0.021 |
| 83 | 0.630 | 0.693 |
| 84 | 0.510 | 0.648 |
| 85 | 0.057 | 0.086 |
| 86 | 0.081 | 0.084 |
| 87 | >1 | >1 |
| 88 | >1 | >1 |
| 89 | 0.158 | 0.079 |
| 90 | 0.375 | 0.302 |
| 91 | >1 | >1 |
| 92 | >1 | 0.750 |

Example 96

Cell Profiling Data (Example 24)

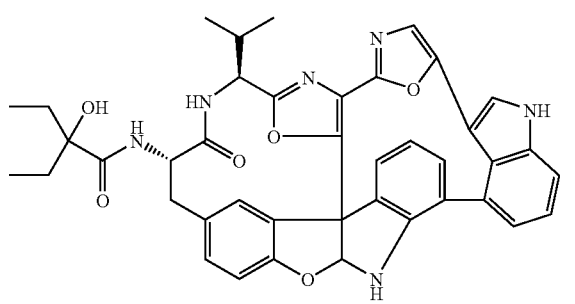

The compound prepared in Example 24 has been shown to kill tumor cells in cell lines derived from a variety of origins. Data is provided in Table 8.

TABLE 8

Cell profiling data for the compound of Example 24

| Tumor Cell line | Origin | IC$_{50}$ (μM) |
| --- | --- | --- |
| U937 | Blood | 0.044 |
| MDA-MB231 | Breast | 0.234 |
| MDA-MB435 | Breast | 0.029 |
| Colo205 | Colon | 0.144 |
| DLD-1 | Colon | 0.515 |
| HT29 | Colon | 0.090 |
| Lovo | Colon | 0.150 |
| T98G | Glial Cells | 0.067 |
| HCC1437 | Lung | 0.195 |
| HCC44 | Lung | 0.036 |
| NCI-H226 | Lung | 0.104 |
| NCI-H460 | Lung | 0.242 |
| SKMES-1 | Lung | 0.470 |
| BxPC3 | Pancreas | 0.213 |
| MiaPaca-2 | Pancreas | 0.111 |
| Panc-1 | Pancreas | 0.288 |
| PL45 | Pancreas | 0.113 |
| SW1990 | Pancreas | 0.360 |
| DU145 | Prostate | 0.057 |
| A2058 | Skin | 0.093 |
| A375 | Skin | 0.162 |
| G361 | Skin | 0.275 |
| SKMEL-5 | Skin | 0.070 |

Example 97

Xenograft Models

General Protocol

Experimental Design
  Animals: Athymic nude mice, female, 6-7 weeks old, 20-25 g. Animals bearing with 180-400 mg tumors were selected for experiment. 7 mice/group.
  Administration: Tail vein injection, 200 μL/mouse, to provide the dose indicated.
  Dosing schedule: 6 injections were given on the days indicated post-tumor cell injection.
  Controls: Vehicle, Compound J at 20 mg/kg.
  Test Compound preparation: Compound J and all test compounds were dissolved in 50% Cremophore/EtOH (1:1) at 10 mg/mL as stock solution. Each compound solution was diluted with saline before injection to the concentration indicated.

Example 98

MiaPaca Xenograft Models

Experimental Design
  Xenograft Model: MiaPaca (pancreatic cancer) cells
  Dosing schedule: 6 injections were given on days 9, 11, 14, 16, 18 and 21 post-tumor cell injection.
  Test Compounds: Example 23, Example 24, and Example 53, at 20 mg/kg.
  Controls: Vehicle, Compound J at 20 mg/kg.
Results
  The inhibition of tumor growth in the MiaPaca xenograft model is shown in FIG. 1, which shows tumor volume (mL$^3$) versus days post tumor cell injection. Treatment with the test compounds did not significantly affect body weight (data not shown). The number of tumor free animals at 35 days post tumor-cell injection for representative compounds is shown in Table 9. For animals treated with the compound of Example 24 at 20 mg/kg, 7 of 7 animals were tumor free at 35 days post tumor cell injection.

TABLE 9

| Test Compound (dose) | Tumor free animals (days) |
| --- | --- |
| Control | 0/7 (35) |
| Ex. 16 (20 mg/kg) | 0/7 (35) |
| Ex. 53 (20 mg/kg) | 1/7 (35) |
| Ex. 23 (20 mg/kg) | 0/7 (35) |
| Ex. 24 (20 mg/kg) | 7/7 (35) |

Example 99

MDA-MB-231-N1 Xenograft Model

Figure 2:
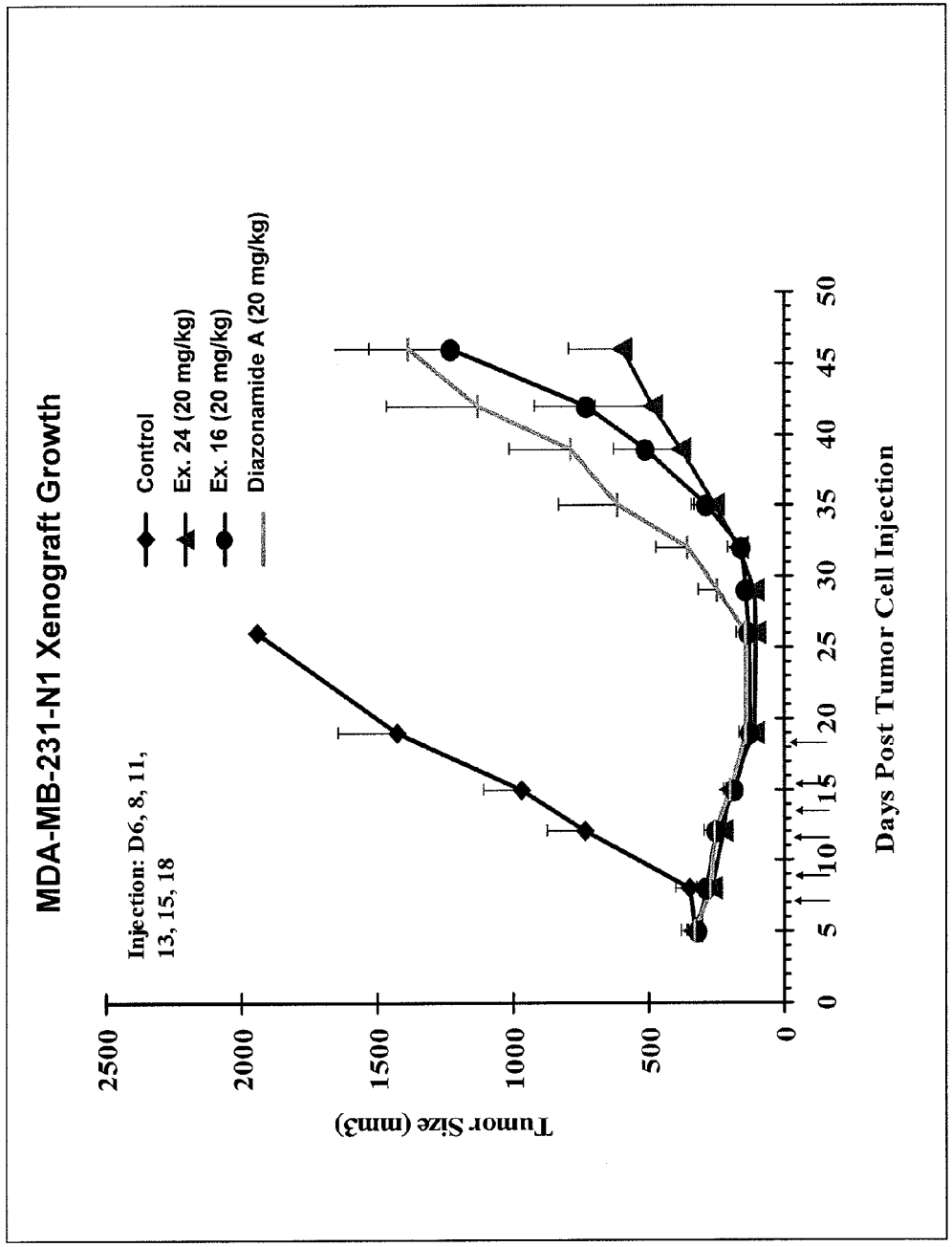
FIG. 2 shows the inhibition of tumor growth in a mouse MDA-MB-231N1 (breast cancer) xenograft model for animals treated with Compound J (Ex. 16), and the compound of Example 24 at 20 mg/kg.

Experimental Design
  Xenograft Model: MDA-MB-231-N1 (breast cancer) cells.
  Dosing schedule: 6 injections were given on days 6, 8, 11, 13, 15 and 18 post-tumor cell injection.
  Test Compounds: Example 24 and Diazonamide A at 20 mg/kg.
  Controls: Vehicle, Compound J at 20 mg/kg.
Results
  The inhibition of tumor growth in the MDA-MB-231-N1 xenograft model is shown in FIG. 2.

Example 100

Colo205 Xenograft Model

Figure 3:
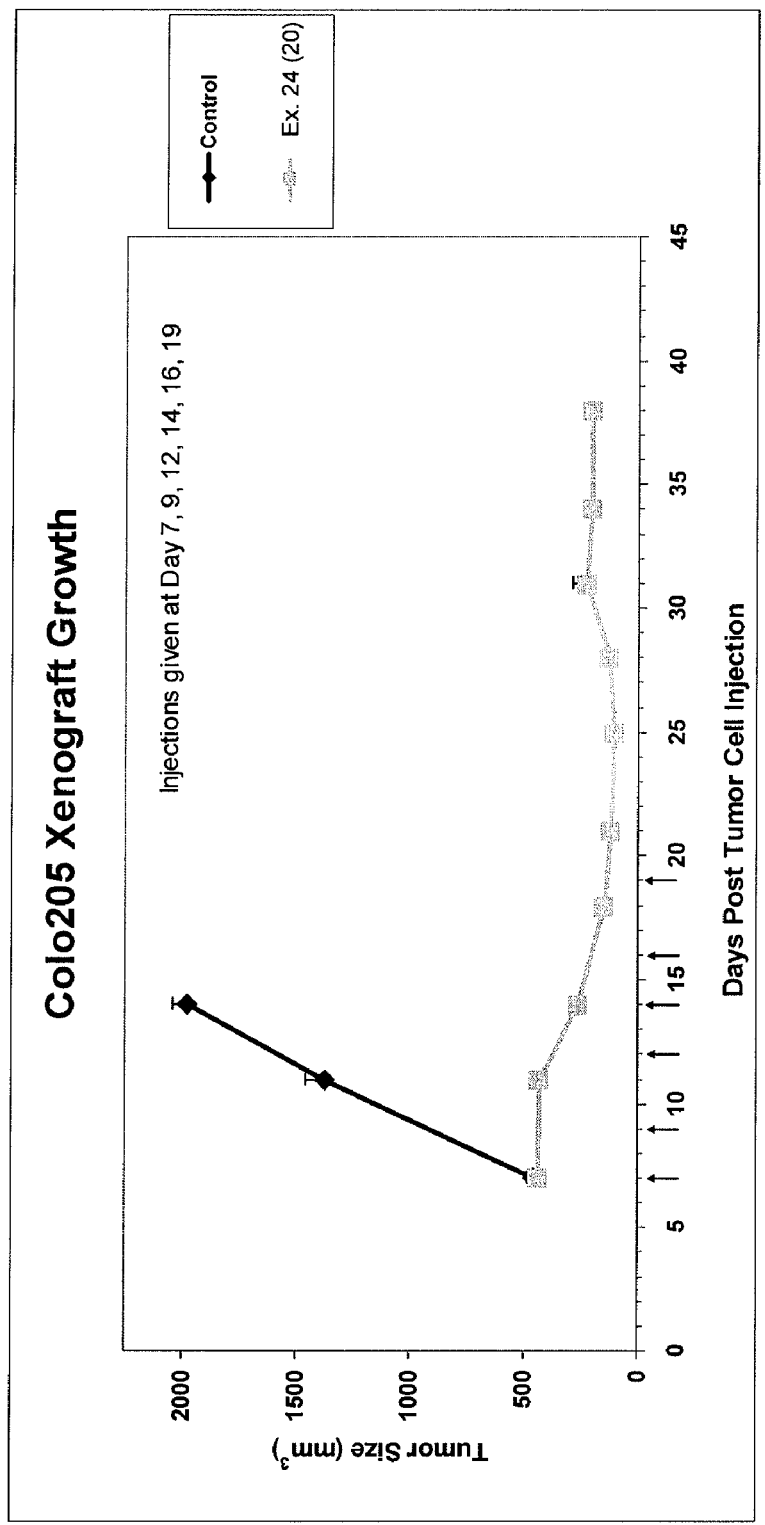
FIG. 3 shows the inhibition of tumor growth in a mouse Colo205 (colon cancer) xenograft model for animals treated with the compound of Example 24 at 20 mg/kg.

Experimental Design
  Xenograft Model: Colo205 (colon cancer) cells.
  Dosing schedule: 6 injections were given on days 7, 9, 12, 14, 16 and 19 post-tumor cell injection.
  Test Compounds: Example 24 at 20 mg/kg.
  Controls: Vehicle.
Results
  The inhibition of tumor growth in the Colo205 xenograft model is shown in FIG. 3.

Example 101

MDA-MB231N1 Xenograft Model

Figure 4:
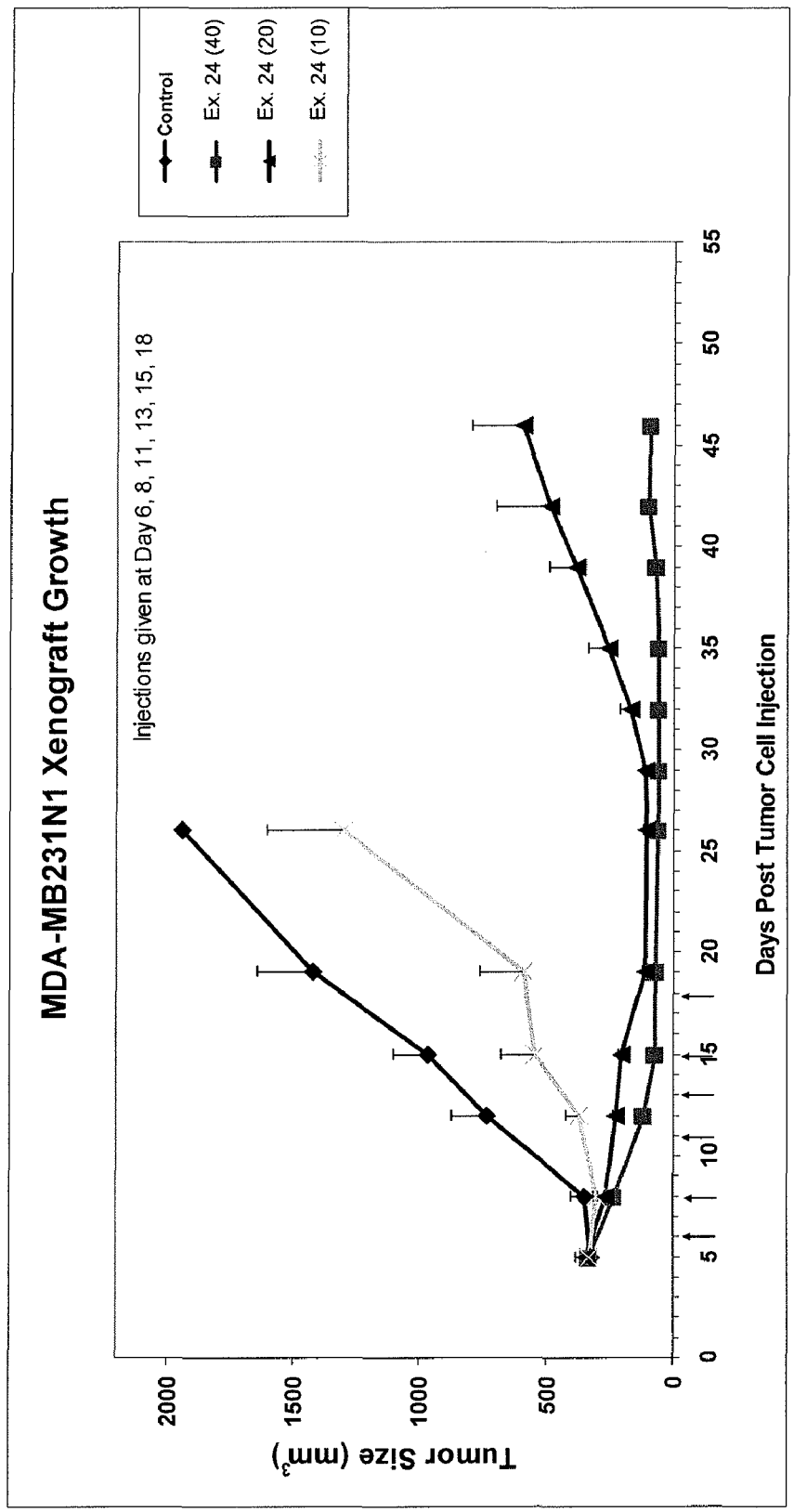
FIG. 4 shows the inhibition of tumor growth in a mouse MDA-MB231N1 (breast cancer) xenograft model for animals treated with the compound of Example 24 at doses of 40 mg/kg, 20 mg/kg and 10 mg/kg.

Experimental Design
   Xenograft Model: MDA-MB231N1 (breast cancer) cells
   Dosing schedule: 6 injections were given on days 6, 8, 11, 13, 15 and 18 post-tumor cell injection.
   Test Compounds: Example 24 at 40 mg/kg, 20 mg/kg and 10 mg/kg.
   Control: Vehicle.
Results
   The comparative inhibition of tumor growth in the MDA-MB231N1 xenograft model at three doses is shown in FIG. 4.

Example 102

MDA-MB435 Xenograft Model

Figure 5:
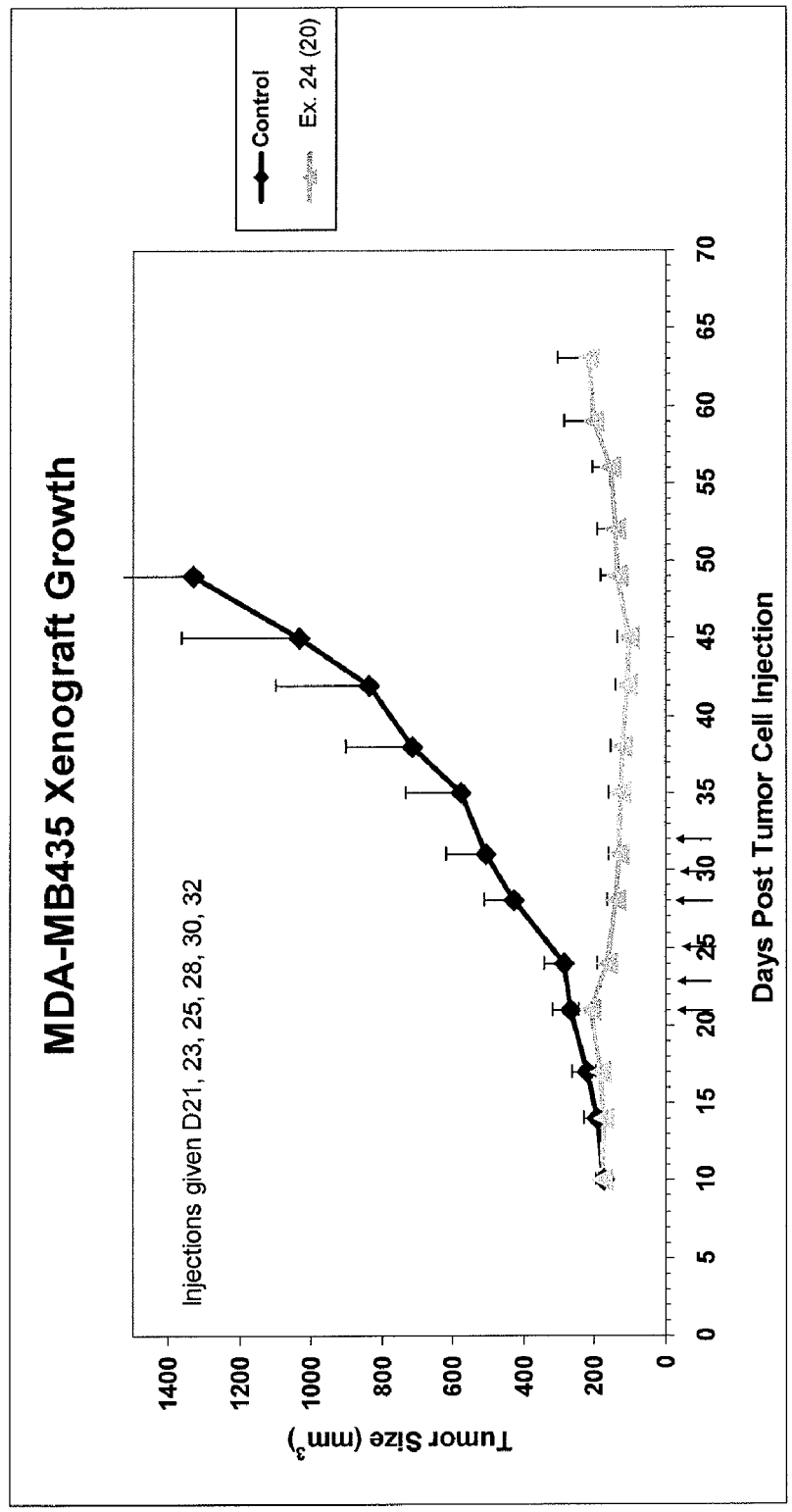
FIG. 5 shows the inhibition of tumor growth in a mouse MDA-MBA435 (breast cancer) xenograft model for animals treated with the compound of Example 24 at 20 mg/kg.

Experimental Design
   Xenograft Model: MDA-MB435 (breast cancer) cells.
   Dosing schedule: 6 injections were given on days 21, 23, 25, 28, 30 and 32 post-tumor cell injection.
   Test Compounds: Example 24 at 20 mg/kg.
   Control: Vehicle.
Results
   The inhibition of tumor growth in the MDA-MB435 xenograft model is shown in FIG. 5.

Example 103

MiaPaca Xenograft Model

Figure 6:
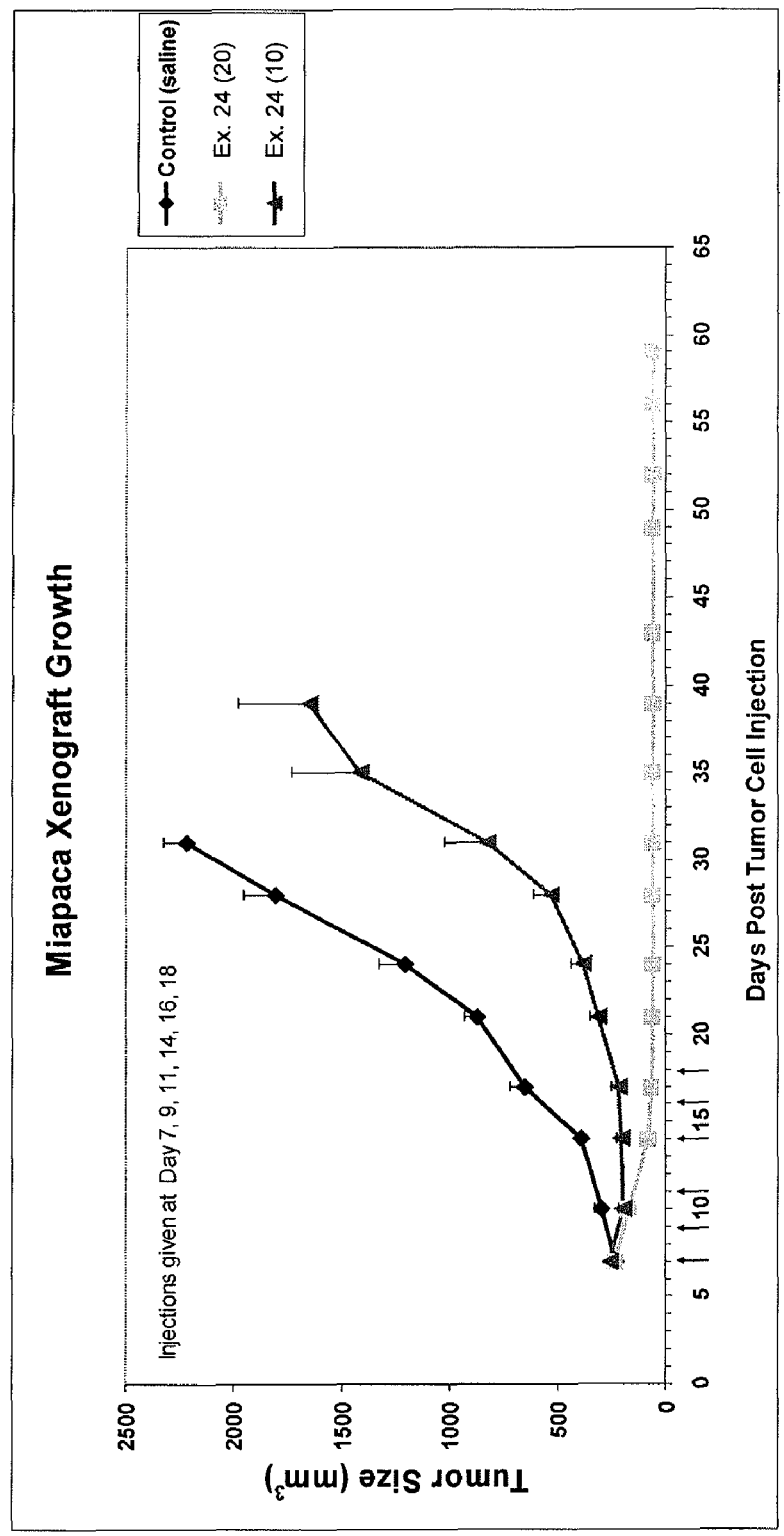
FIG. 6 shows the inhibition of tumor growth in a mouse MiaPaca (pancreatic cancer) xenograft model for animals treated with the compound of Example 24 at 20 mg/kg and 10 mg/kg.

Experimental Design
   Xenograft Model: MiaPaca (pancreatic cancer) cells.
   Dosing schedule: 6 injections were given on days 7, 9, 11, 14, 16 and 18 post-tumor cell injection.
   Test Compounds: Example 24 at 20 mg/kg and 10 mg/kg.
   Control: Vehicle.
Results
   The inhibition of tumor growth in the MiaPaca xenograft model at two doses is shown in FIG. 6.

Example 104

HT29 Xenograft Model

Figure 7:
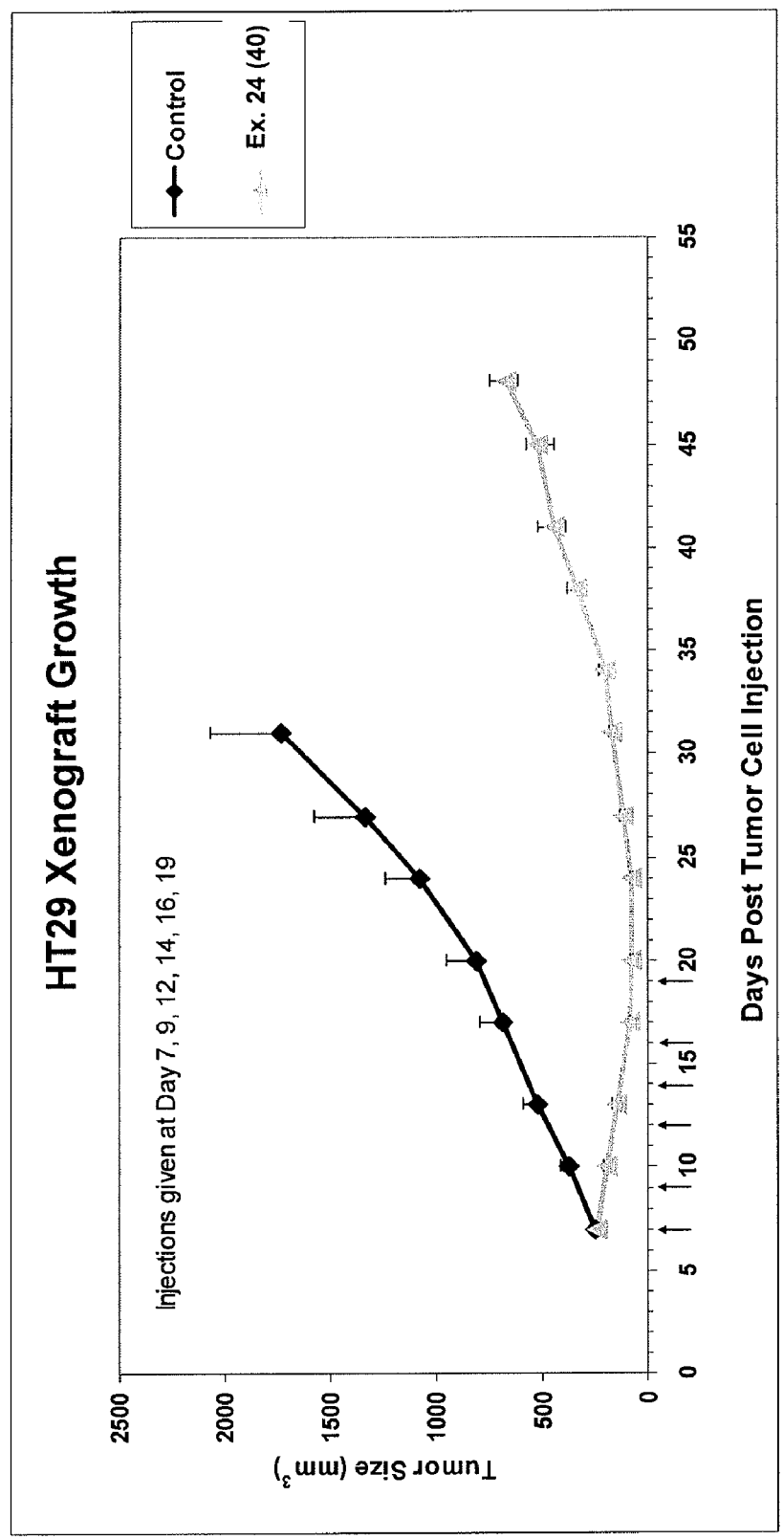
FIG. 7 shows the inhibition of tumor growth in a mouse HT29 (colon cancer) xenograft model for animals treated with the compound of Example 24 Example at 40 mg/kg.

Experimental Design
   Xenograft Model: HT29 (colon cancer) cells.
   Dosing schedule: 6 injections were given on days 7, 9, 12, 14, 16 and 19 post-tumor cell injection.
   Test Compounds: Example 24 at 40 mg/kg.
   Control: Vehicle.
Results
   The inhibition of tumor growth in the HT29 xenograft model is shown in FIG. 7.

Example 105

HPAC Xenograft Model

Figure 8:
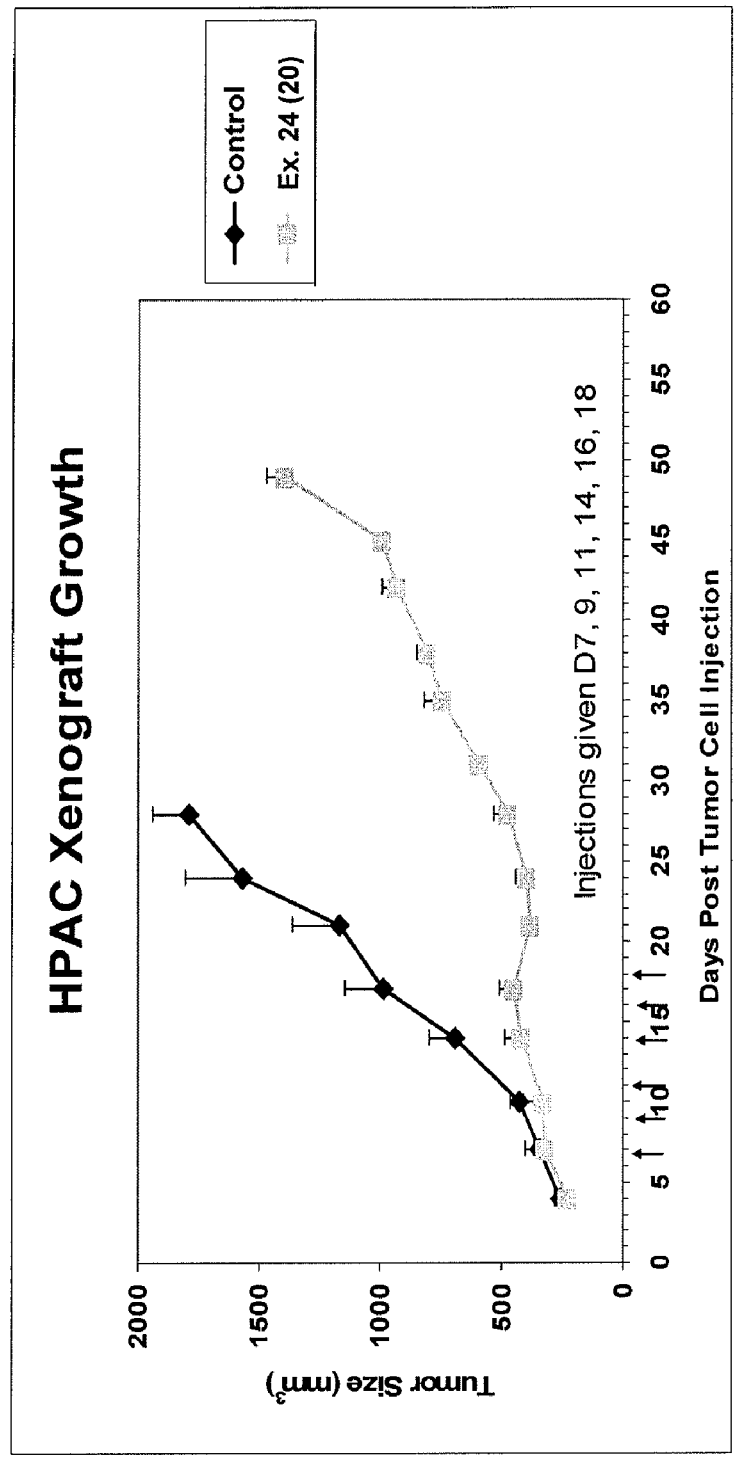
FIG. 8 shows the inhibition of tumor growth in a mouse HPAC (pancreatic cancer) xenograft model for animals treated with the compound of Example 24 at 20 mg/kg.

Experimental Design
   Xenograft Model: HPAC (pancreatic cancer) cells.
   Dosing schedule: 6 injections were given on days 7, 9, 11, 14, 16 and 18 post-tumor cell injection.
   Test Compounds: Example 24 at 20 mg/kg.
   Control: Vehicle.
Results
   The inhibition of tumor growth in the HPAC xenograft model is shown in FIG. 8.

Example 106

A2058 Xenograft Model

Figure 9:
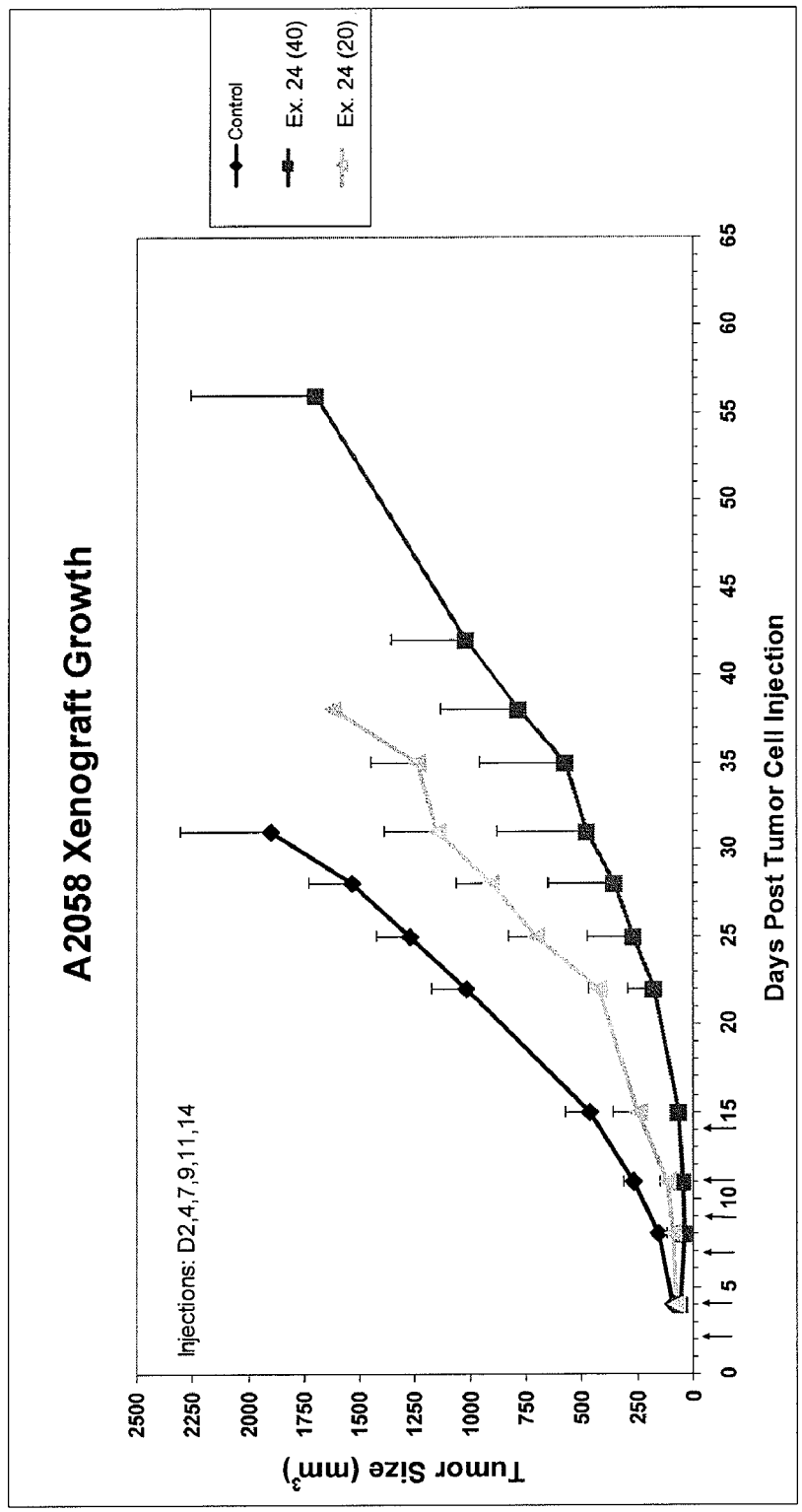
FIG. 9 shows the inhibition of tumor growth in a mouse A2058 (melanoma) xenograft model for animals treated with the compound of Example 24 at 40 mg/kg and 20 mg/kg.

Experimental Design
   Xenograft Model: A2058 (melanoma) cells.
   Dosing schedule: 6 injections were given on days 2, 4, 7, 9, 11 and 14 post-tumor cell injection.
   Test Compounds: Example 24 at 40 mg/kg and 20 mg/kg.
   Control: Vehicle.
Results
   The inhibition of tumor growth in the A2058 xenograft model is shown in FIG. 9.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

The invention claimed is:
1. A compound having the formula (V):

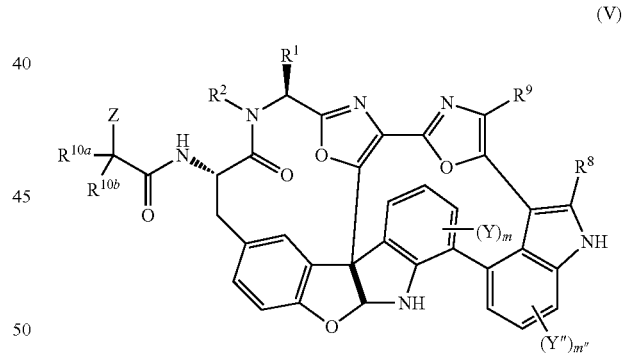

(V)

or a pharmaceutically acceptable salt or conjugate thereof;
wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;
$R^2$ is H, or C1-C8 alkyl, C1-C8 heteroalkyl, C6-C14 arylalkyl, C6-C14 heteroarylalkyl, each of which may be optionally substituted; or
$R^1$ and $R^2$ may be taken together with the atoms to which they are attached to form an optionally substituted 5- to 7-membered azacyclic ring, optionally containing an additional heteroatom selected from N, O, and S as a ring member;
$R^8$ and $R^9$ are independently H, halo, or C1-C6 alkyl, C2-C6 alkenyl, C2-C6 alkynyl, C6-C12 aryl, C5-C12 heteroaryl, each of which may be optionally substituted, or COOR$^{11}$ or CONR$^{11}_2$, where each R$^{11}$ is independently H or C1-C4 alkyl;

m and m" are independently 0-3; and each Y and Y" is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted;

Z is OH, OR, CH$_2$OR, SR, or NR$_2$, where each R is independently H, optionally fluorinated C1-C4 alkyl, or optionally fluorinated C1-C4 acyl; and R$^{10a}$ and R$^{10b}$ are taken together with the carbon to which they are attached to form a C3-C8 cycloalkyl or a C3-C8 heterocyclyl ring, which may be optionally substituted.

2. The compound of claim 1, wherein each of R$^8$ and R$^9$ is independently H or Cl.

3. The compound of claim 1, wherein Z is OH.

4. The compound of claim 1, wherein each of R$^{10a}$ and R$^{10b}$ is an optionally substituted C1-C6 alkyl.

5. The compound of claim 1, wherein each of R$^{10a}$ and R$^{10b}$ is methyl or ethyl.

6. The compound of claim 1, wherein R$^{10a}$ and R$^{10b}$ are taken together with the carbon to which they are attached to form a C3-C8 cycloalkyl.

7. The compound of claim 1, having the formula:

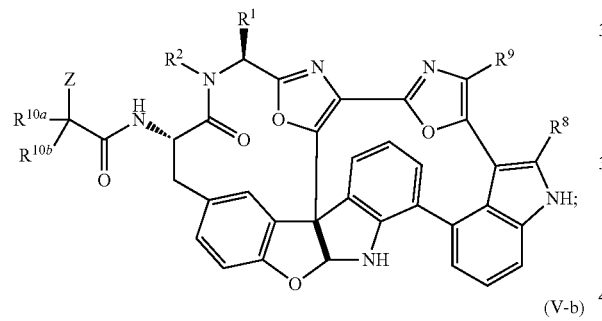
(V-a)

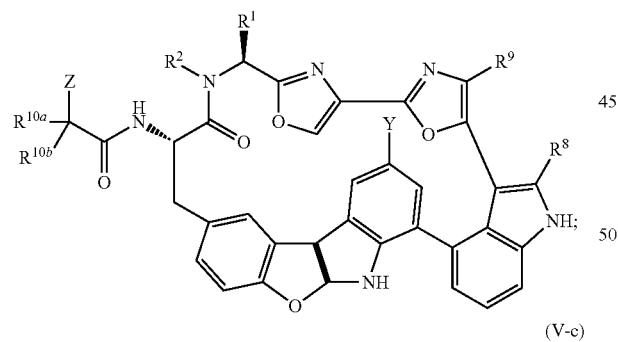
(V-b)

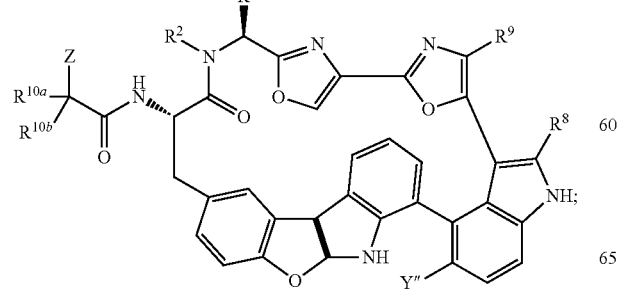
(V-c)

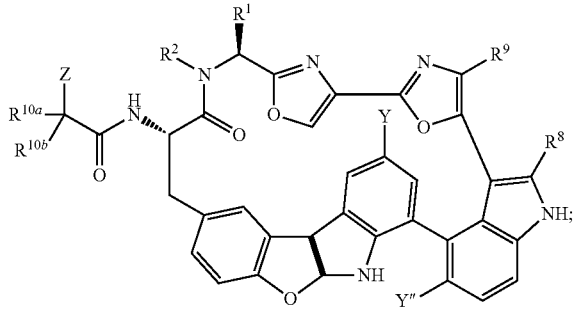
(V-d)

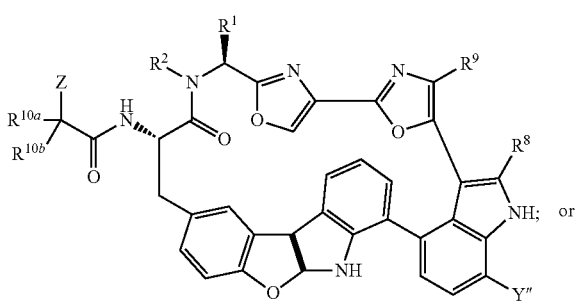
(V-e)

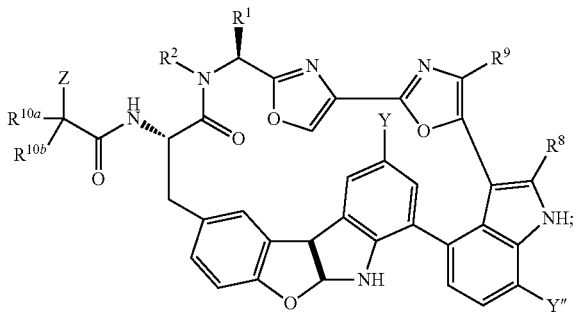
(V-f)

or a pharmaceutically acceptable salt or conjugate thereof.

8. A compound having the formula (VI):

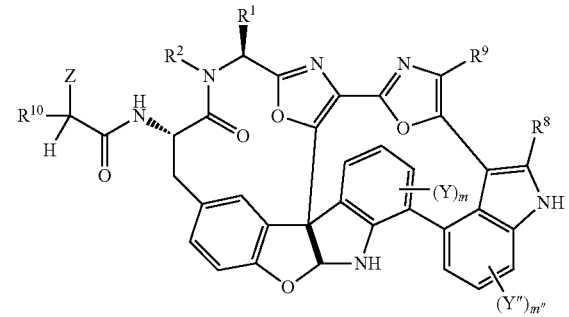
(VI)

or a pharmaceutically acceptable salt or conjugate thereof;

wherein R$^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

R² is H, or C1-C8 alkyl, C1-C8 heteroalkyl, C6-C14 arylalkyl, C6-C14 heteroarylalkyl, each of which may be optionally substituted; or R¹ and R² may be taken together with the atoms to which they are attached to form an optionally substituted 5- to 7-membered azacyclic ring, optionally containing an additional heteroatom selected from N, O, and S as a ring member;

R⁸ and R⁹ are independently H, halo, or C1-C6 alkyl, C2-C6 alkenyl, C2-C6 alkynyl, C6-C12 aryl, C5-C12 heteroaryl, each of which may be optionally substituted, or COOR¹¹ or CONR¹¹₂, where each R¹¹ is independently H or C1-C4 alkyl;

m and m'' are independently 0-3; and each Y and Y'' is independently halo, OH, C1-C4 alkoxy, or C1-C8 alkyl, C2-C8 alkenyl, C2-C8 alkynyl, C6-C12 aryl, or C6-C14 arylalkyl, or a heteroform of one of these, each of which may be optionally substituted;

Z is OH, OR, CH₂OR, SR, or NR₂, where each R is independently H, optionally fluorinated C1-C4 alkyl, or optionally fluorinated C1-C4 acyl; and R¹⁰ is C1-C6 alkyl, C2-C6 alkenyl, C2-C6 alkynyl, C3-C8 cycloalkyl, C3-C8 cycloalkylalkyl, C6-C12 aryl, C6-C20 arylalkyl, or a heteroform of one of these, each of which may be optionally substituted; provided the compound is not:

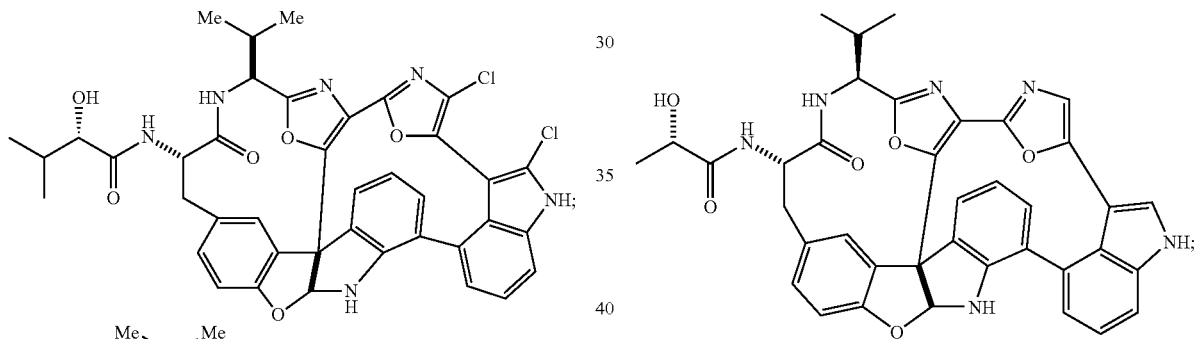

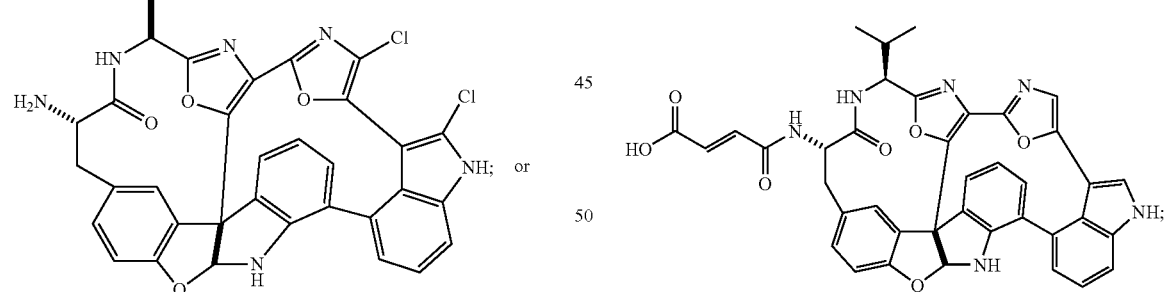

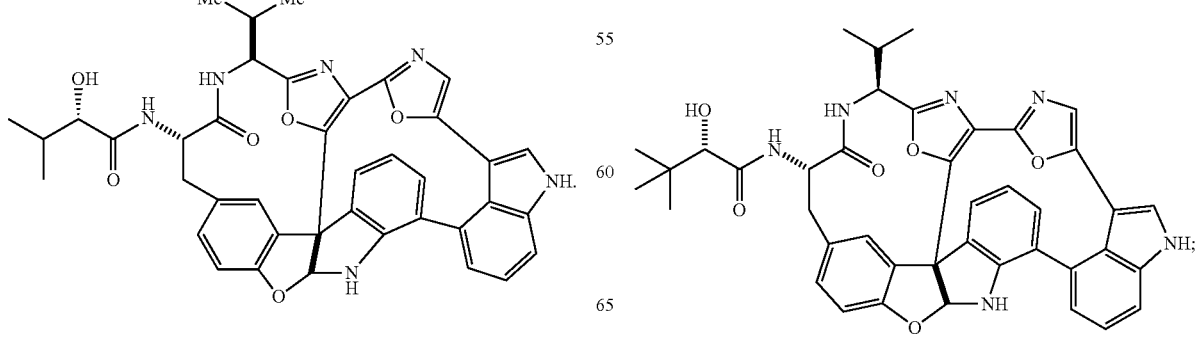

9. A compound selected from the group consisting of:

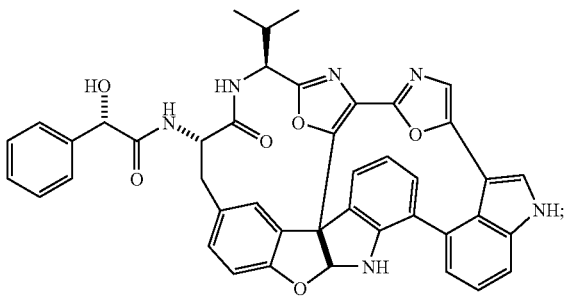

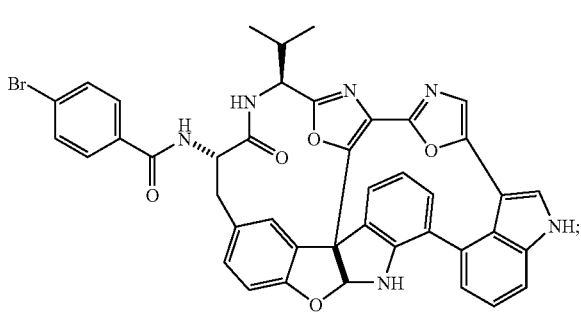

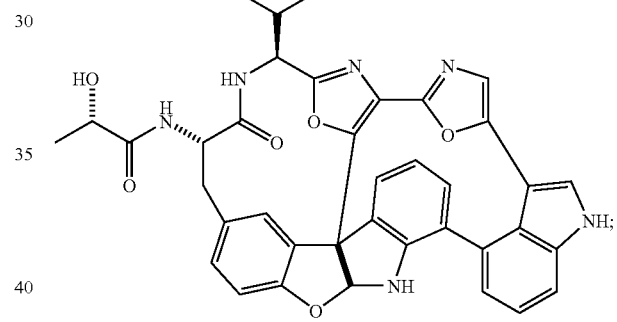

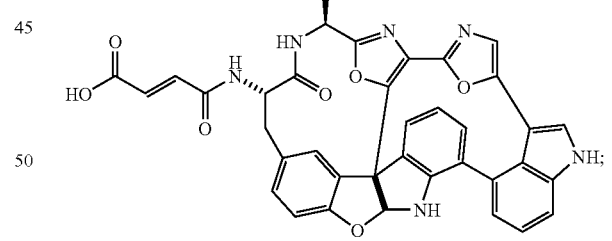

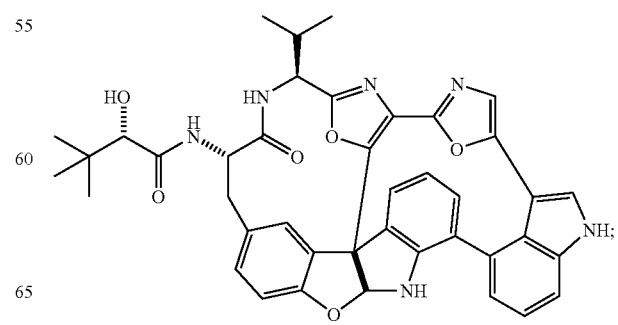

105
-continued
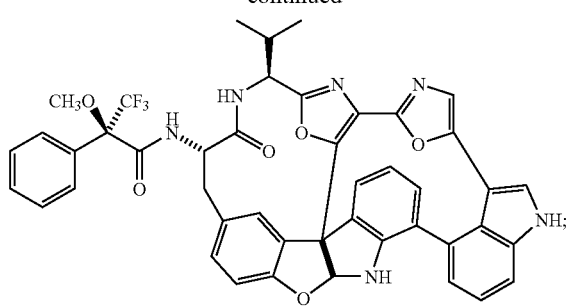
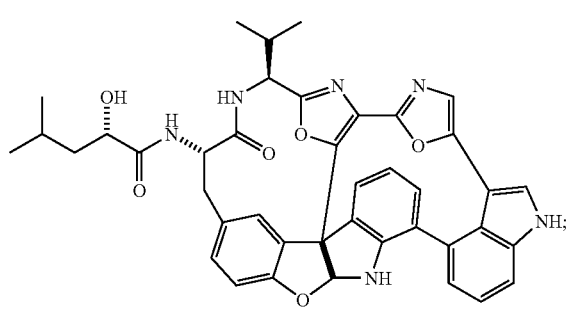
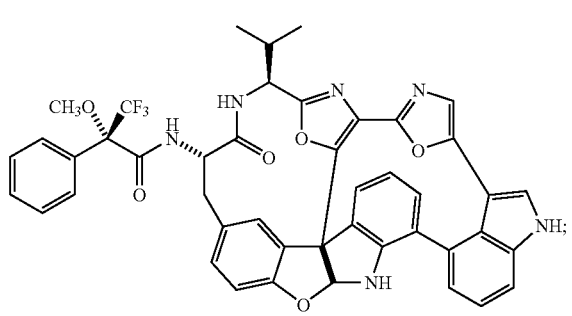
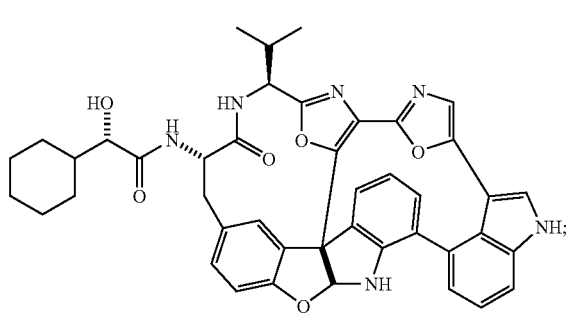
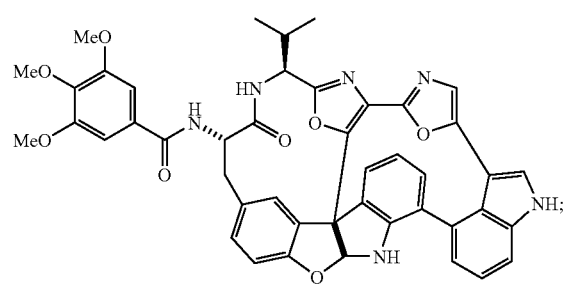
106
-continued
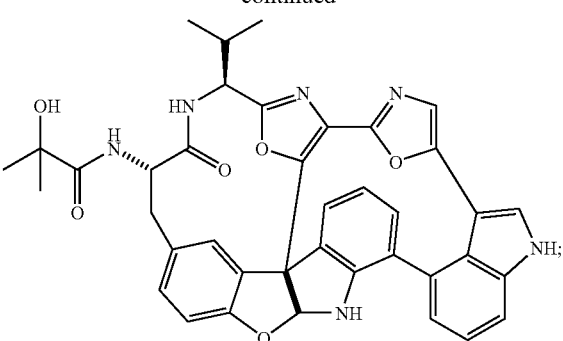
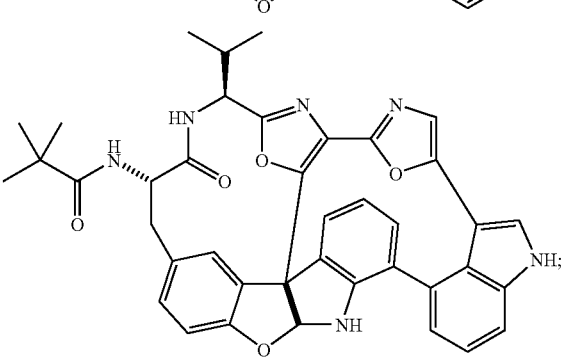
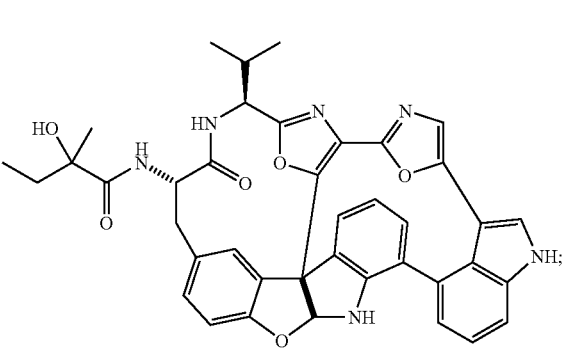
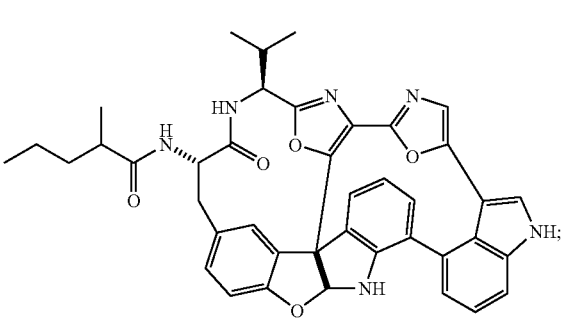
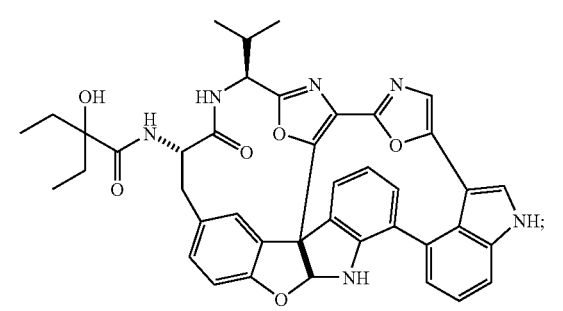

107
-continued
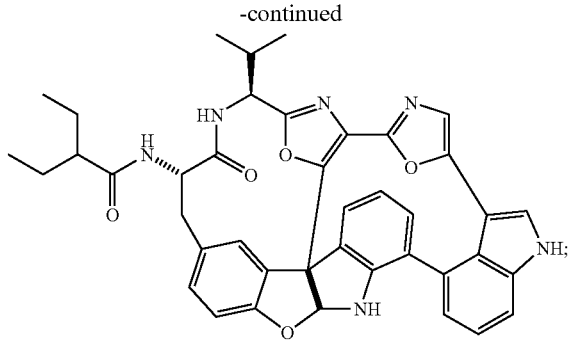
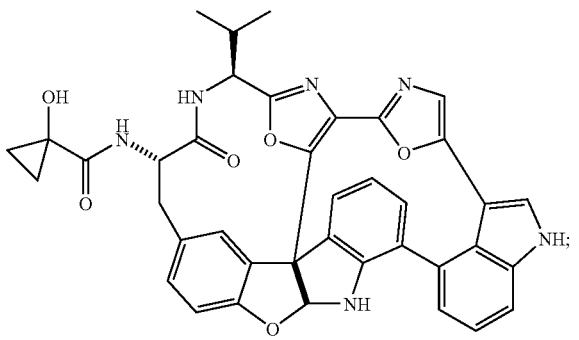
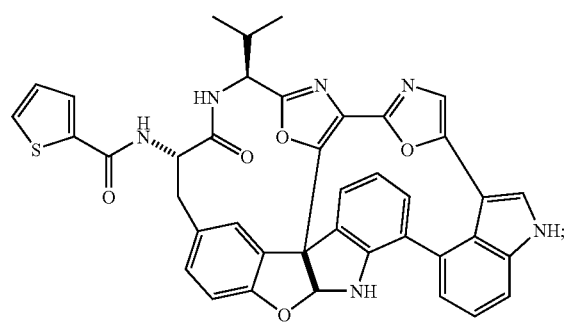
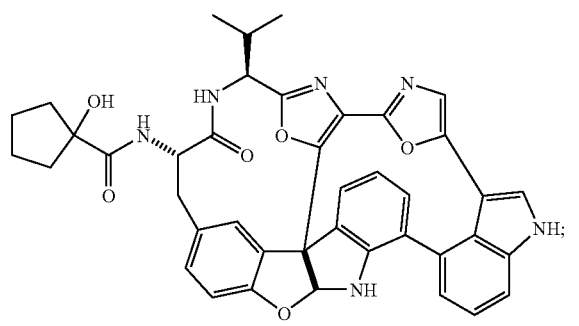
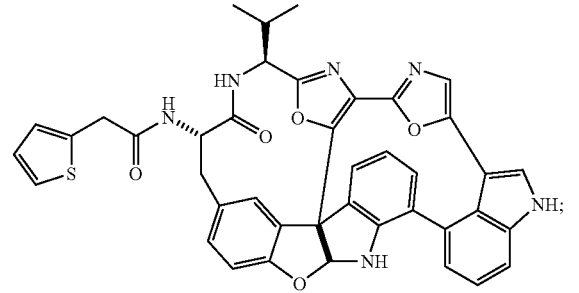
108
-continued
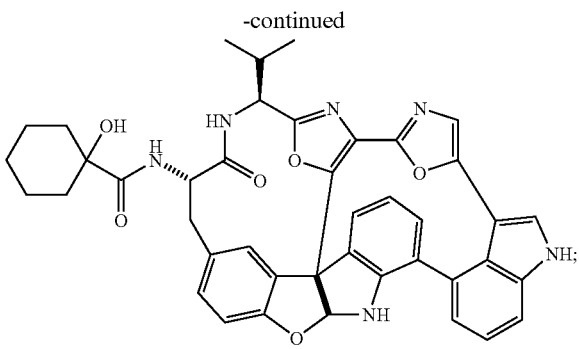
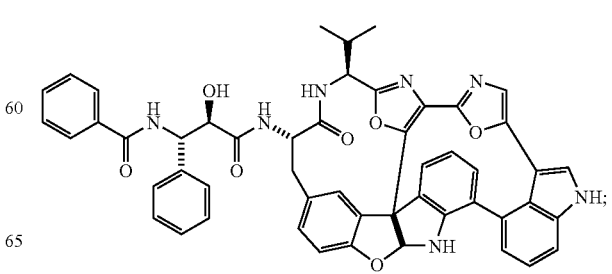

109
-continued
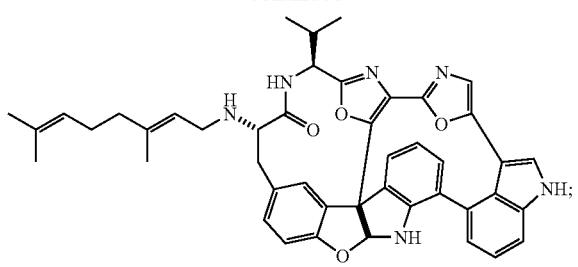
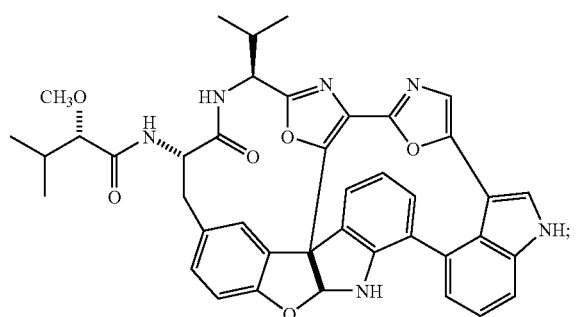
110
-continued
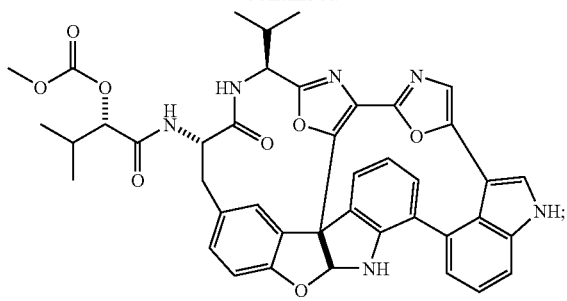
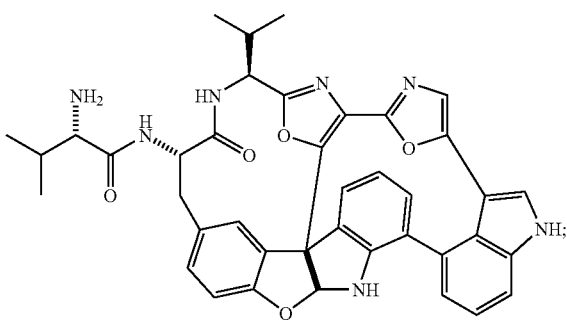
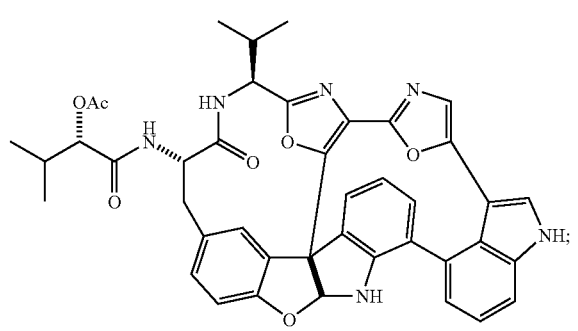
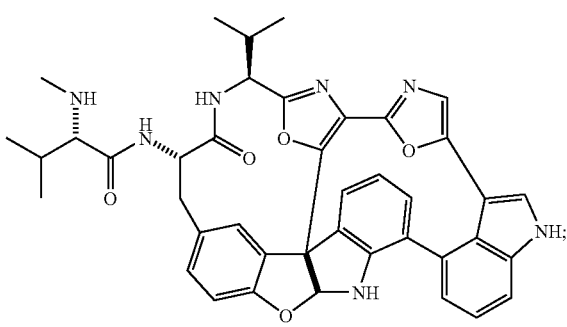

111
-continued

112
-continued

113
-continued
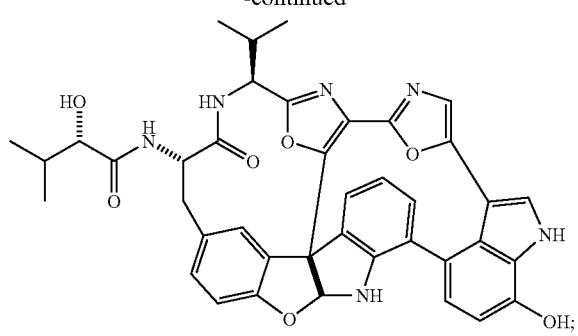
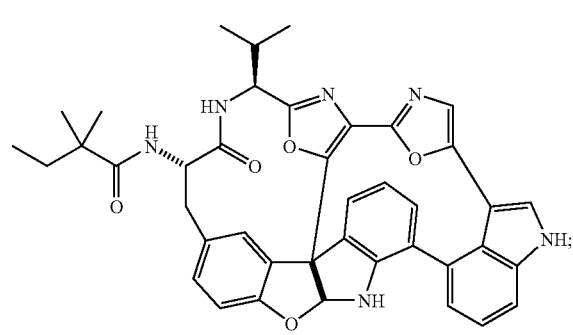
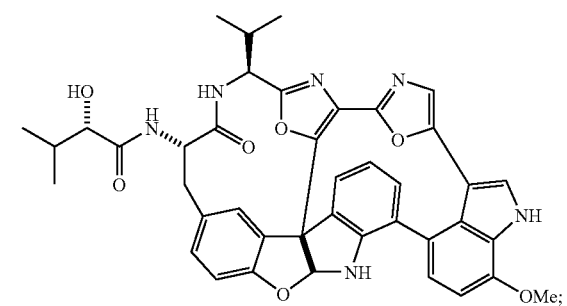
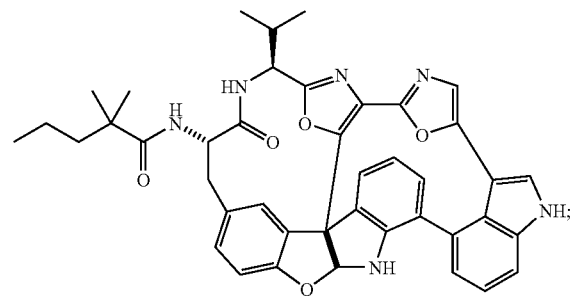
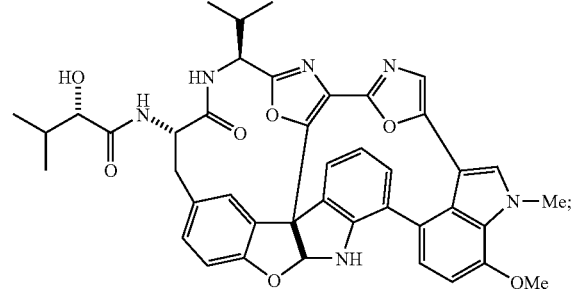
114
-continued
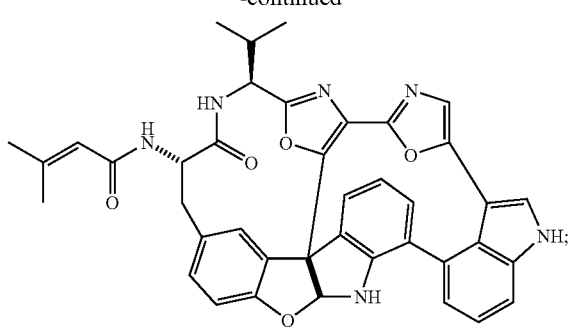
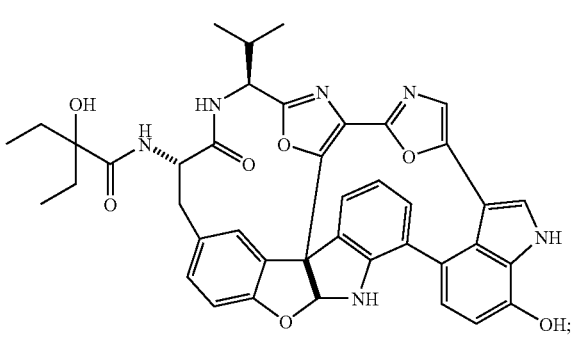
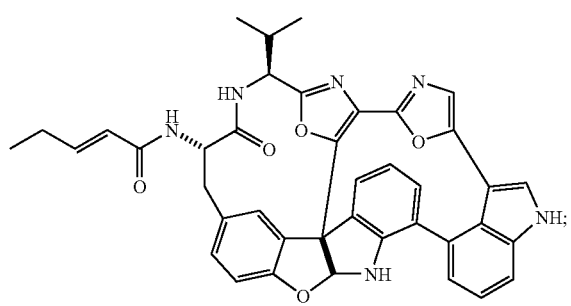
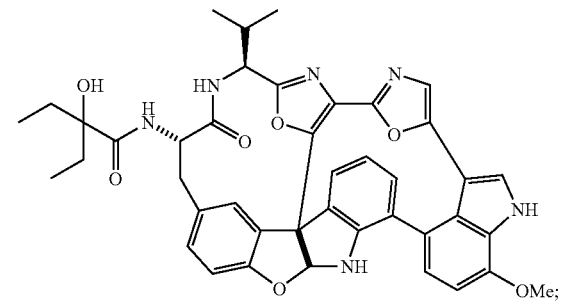
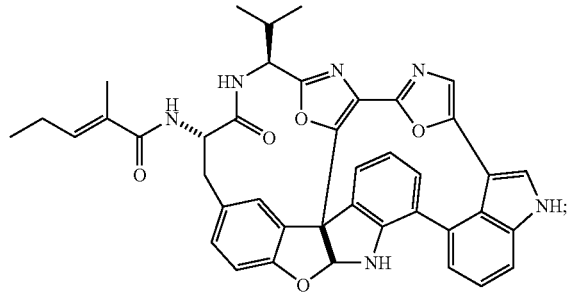

115
-continued
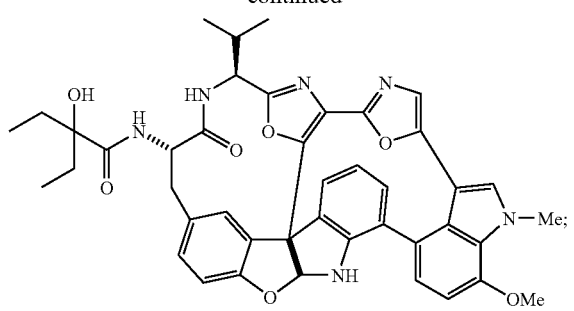
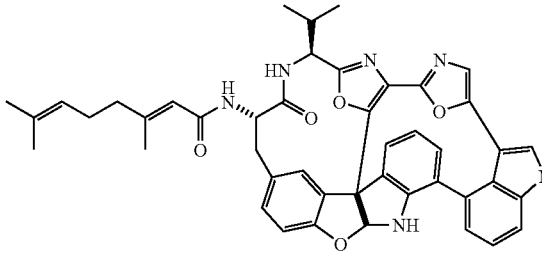
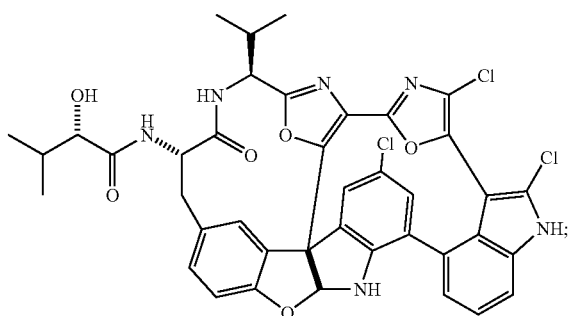
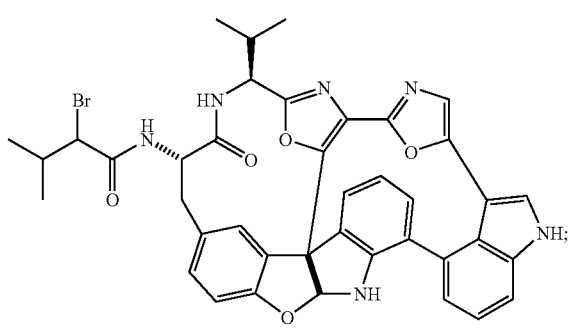
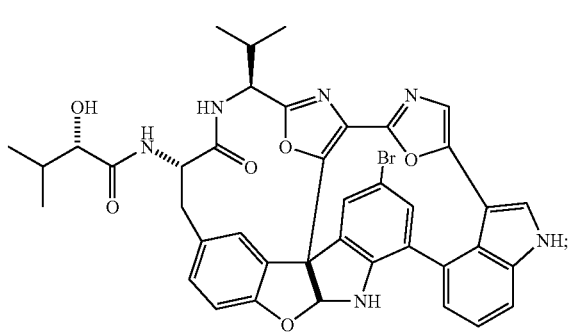
116
-continued
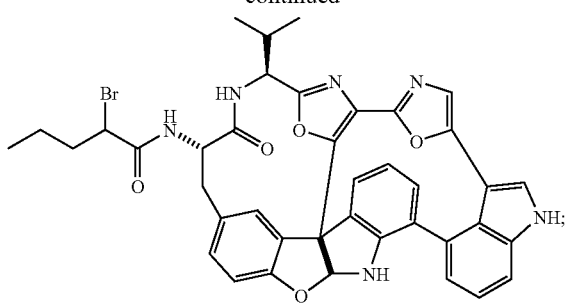
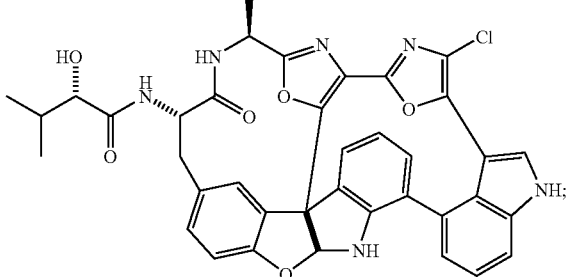
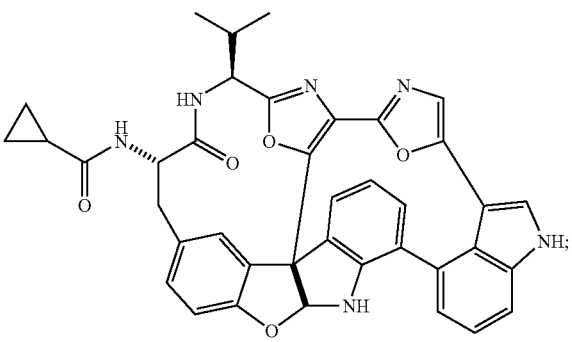
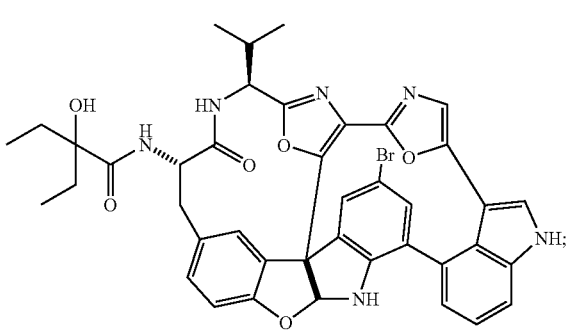
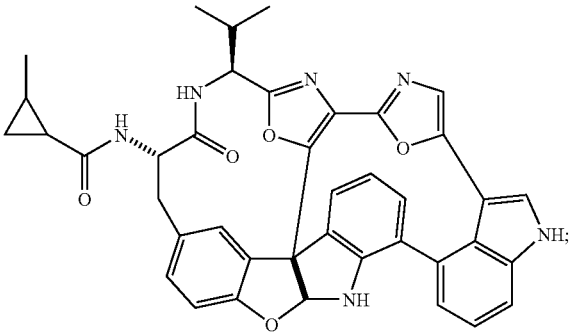

117
-continued
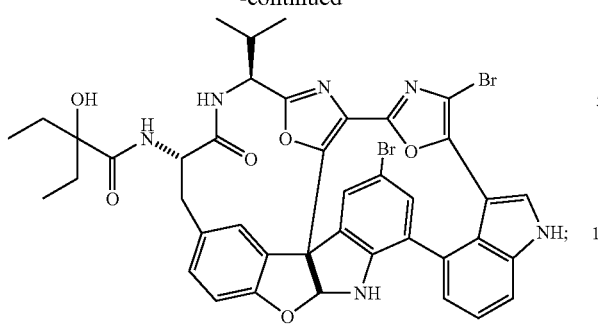
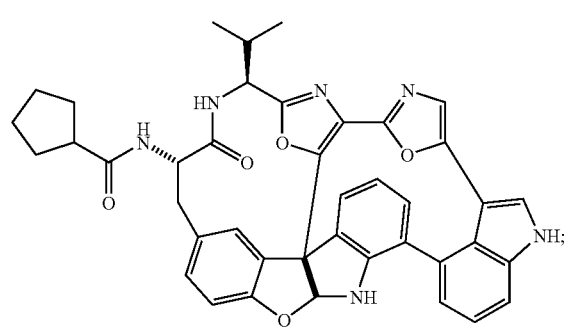
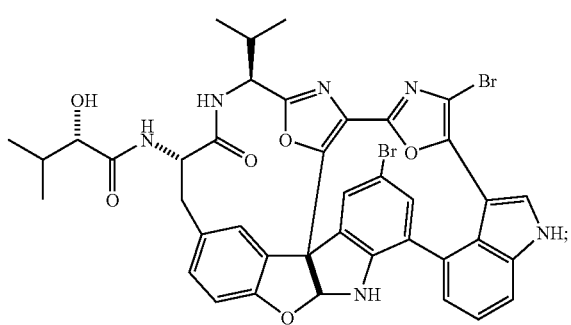
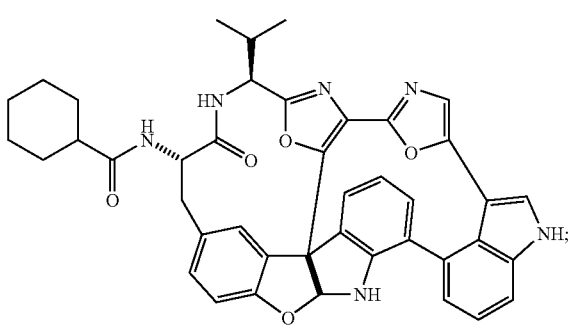
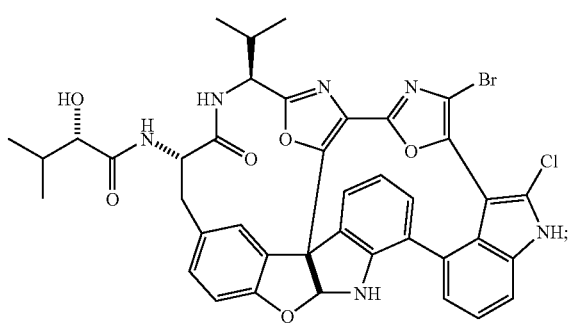
118
-continued
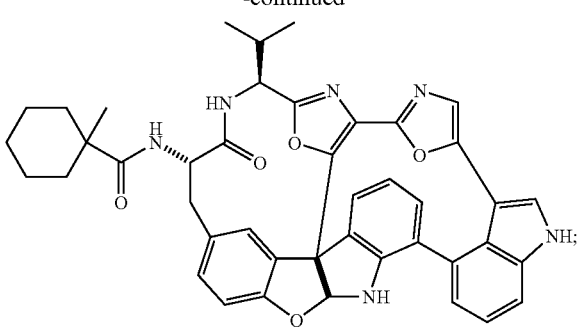
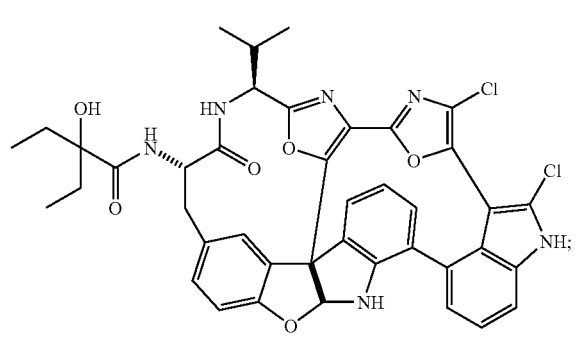
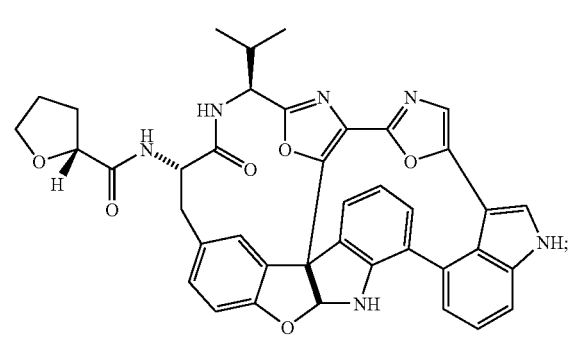
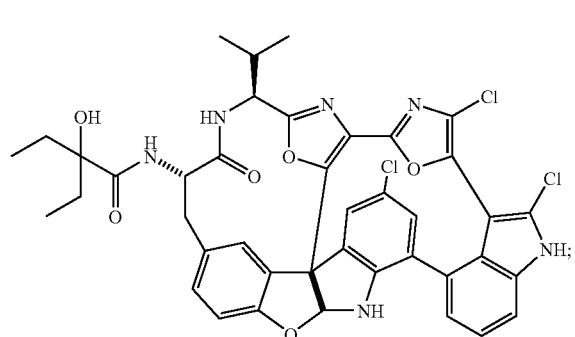
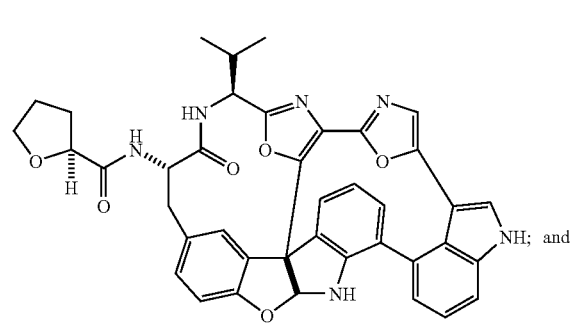

-continued

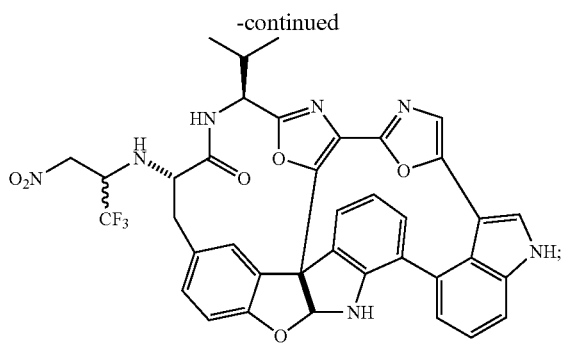

or a pharmaceutically acceptable salt or conjugate thereof.

10. A compound having the structure

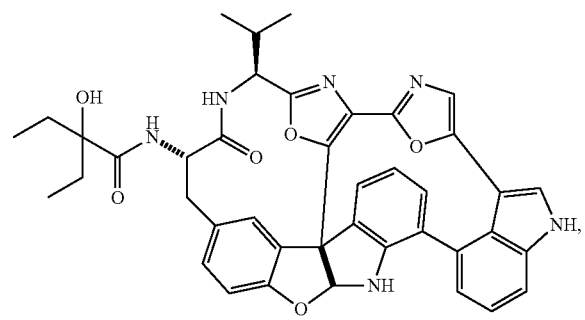

or a pharmaceutically acceptable salt or conjugate thereof.

11. A compound of claim 1 in the form of a pharmaceutically acceptable salt.

12. A compound of claim 1 in the form of a conjugate.

13. The compound of claim 12, wherein the compound is conjugated to an antibody or an immunologically active fragment thereof, or to a polyethylene glycol (PEG) moiety.

14. A pharmaceutical composition comprising a compound of claim 1 and at least one pharmaceutically acceptable excipient.

15. A pharmaceutical composition comprising the compound of claim 10, and at least one pharmaceutically acceptable excipient.

16. A method of lessening, improving ameliorating, alleviating or removing a symptom or pathology of pancreatic cancer, breast cancer, colon cancer, or melanoma, comprising administering to a subject in need thereof a therapeutically effective amount of the compound of claim 1.

17. A method of lessening, improving ameliorating, alleviating or removing a symptom or pathology of pancreatic cancer, breast cancer, colon cancer, or melanoma, comprising administering to a subject in need thereof a therapeutically effective amount of the compound of claim 9.

18. A method of lessening, improving ameliorating, alleviating or removing a symptom or pathology of pancreatic cancer, breast cancer, colon cancer, or melanoma, comprising administering to a subject in need thereof a therapeutically effective amount of the compound of claim 10.

19. A method of lessening, improving ameliorating, alleviating or removing a symptom or pathology of pancreatic cancer, breast cancer, colon cancer, or melanoma, comprising administering to a subject in need thereof a therapeutically effective amount of the compound of claim 8.

20. A compound of claim 7 in the form of a pharmaceutically acceptable salt.

21. A compound of claim 8 in the form of a pharmaceutically acceptable salt.

22. A compound of claim 9 in the form of a pharmaceutically acceptable salt.

23. A compound of claim 10 in the form of a pharmaceutically acceptable salt.

24. A compound of claim 9 selected from the group consisting of:

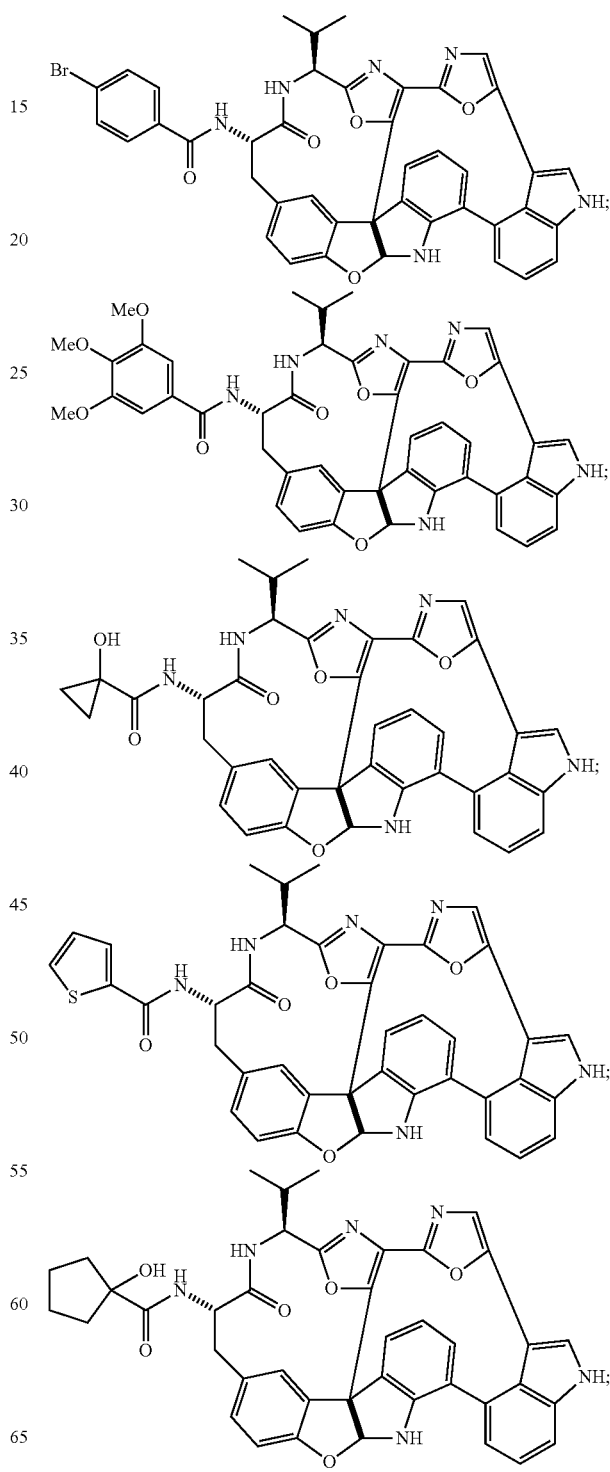

121
-continued
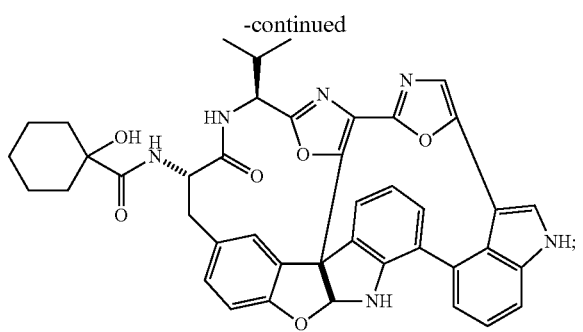
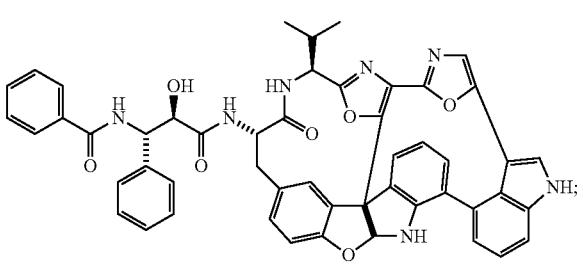
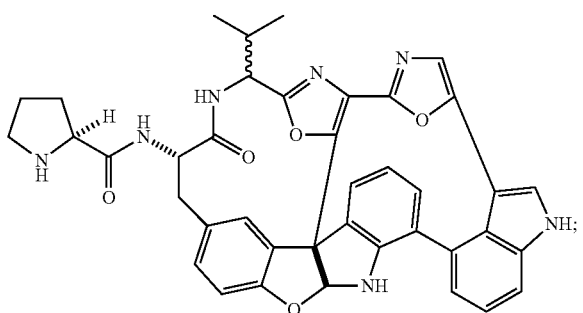
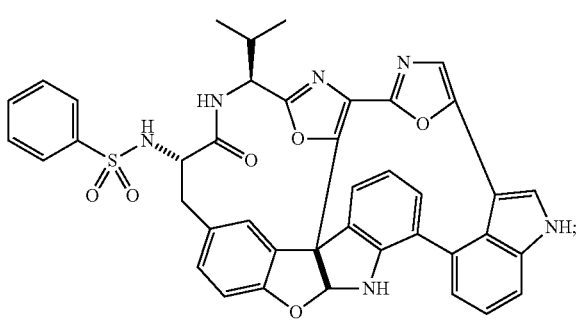
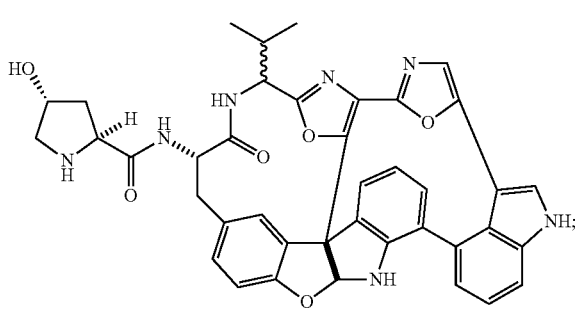
122
-continued
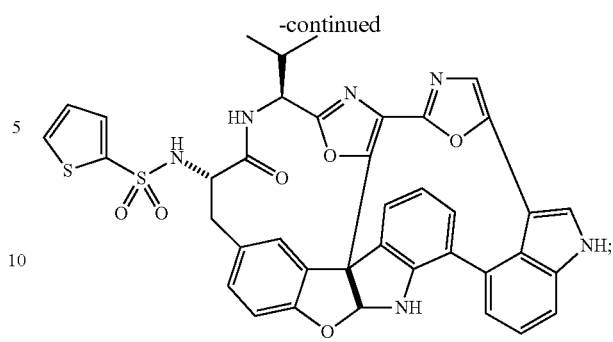
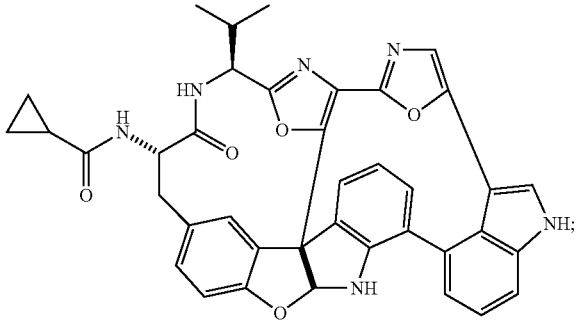
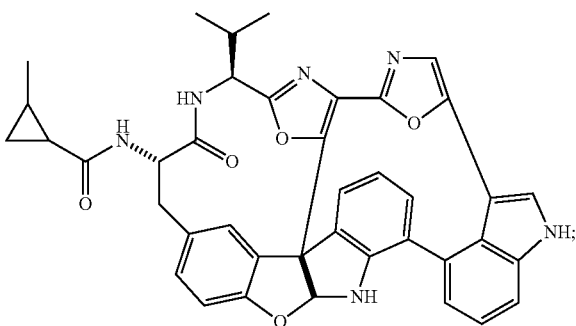
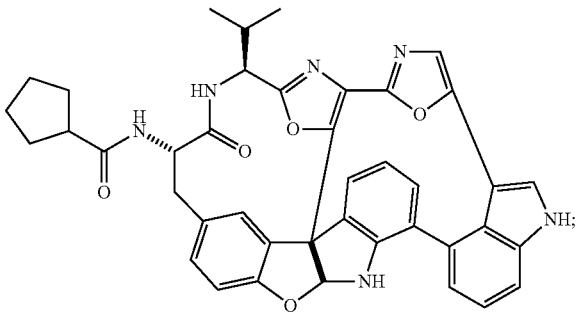
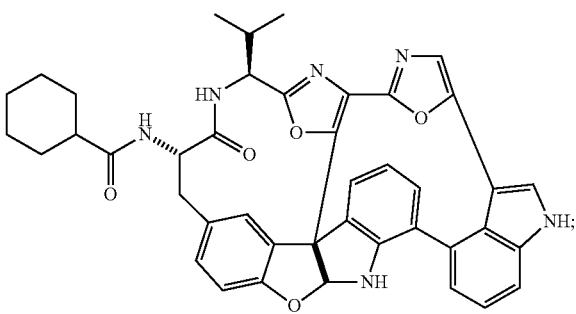

123
-continued
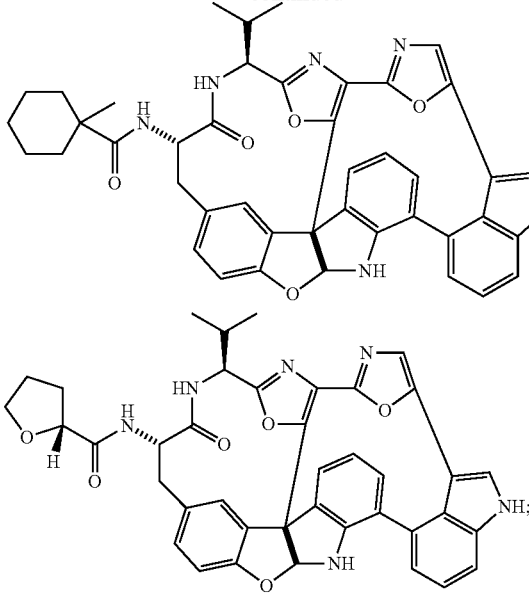
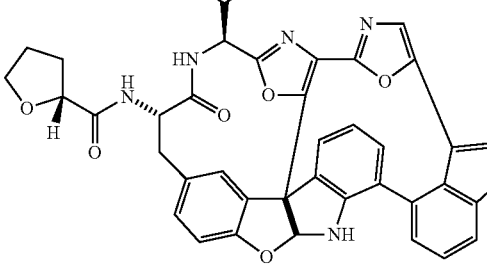
and
124
-continued
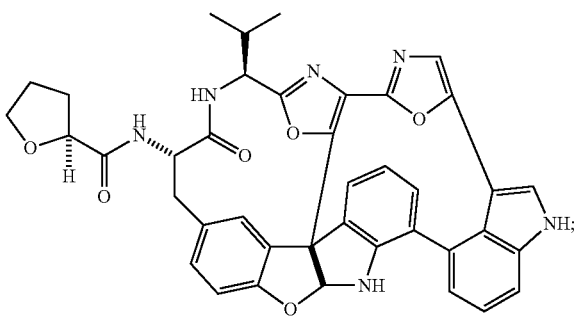
or a pharmaceutically acceptable salt or conjugate thereof.
* * * * *